(12) United States Patent
Rhee et al.

(10) Patent No.: US 10,966,744 B2
(45) Date of Patent: Apr. 6, 2021

(54) ULTRASONIC SURGICAL INSTRUMENT WITH PIEZOELECTRIC CENTRAL LUMEN TRANSDUCER

(71) Applicant: Ethicon LLC, Guaynabo, PR (US)

(72) Inventors: Sora Rhee, Pennsylvania Furnace, PA (US); Jacob S. Gee, Cincinnati, OH (US); Steven P. Smolik, West Chester, OH (US); Stephen J. Balek, Springboro, OH (US); William D. Dannaher, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 9 days.

(21) Appl. No.: 16/170,788

(22) Filed: Oct. 25, 2018

(65) Prior Publication Data
US 2019/0090900 A1 Mar. 28, 2019

Related U.S. Application Data

(62) Division of application No. 15/626,768, filed on Jun. 19, 2017, now Pat. No. 10,245,064.
(Continued)

(51) Int. Cl.
*A61B 17/32* (2006.01)
*B06B 1/06* (2006.01)
(Continued)

(52) U.S. Cl.
CPC ............ *A61B 17/320068* (2013.01); *A61B 17/320092* (2013.01); *B06B 1/0611* (2013.01);
(Continued)

(58) Field of Classification Search
CPC .... A61B 17/320068; A61B 17/320092; A61B 2017/00084; A61B 2017/00402;
(Continued)

(56) References Cited

U.S. PATENT DOCUMENTS

| 969,528 A | 9/1910 | Disbrow |
| 1,570,025 A | 1/1926 | Young |

(Continued)

FOREIGN PATENT DOCUMENTS

| CA | 2535467 A1 | 4/1993 |
| CA | 2214413 A1 | 9/1996 |

(Continued)

OTHER PUBLICATIONS

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
(Continued)

*Primary Examiner* — Bryan P Gordon

(57) ABSTRACT

A surgical instrument includes a transducer assembly with a housing having a conduit section and a base portion. A fluid passageway is defined through the conduit and base portion, an ultrasonic transducer including a plurality of piezoelectric elements and a plurality of electrodes are arranged in a stack configuration, where an electrode is located between each pair of piezoelectric elements. A first borehole is defined through the ultrasonic transducer and an end mass having a second borehole defined therethrough. A surface of the end mass is positioned adjacent a first end of the ultrasonic transducer, the end mass is configured to engage with the housing, and the conduit section of the housing is configured to pass through the second borehole of the end mass. The end mass is configured to compress the ultrasonic transducer against a surface of the housing when the end mass is engaged with the housing.

19 Claims, 24 Drawing Sheets

Related U.S. Application Data

(60) Provisional application No. 62/381,785, filed on Aug. 31, 2016, provisional application No. 62/361,136, filed on Jul. 12, 2016.

(51) Int. Cl.

| | | |
|---|---|---|
| *H01L 41/09* | (2006.01) | |
| *H01L 41/04* | (2006.01) | |
| *B06B 3/00* | (2006.01) | |
| *A61B 17/00* | (2006.01) | |
| *A61B 17/22* | (2006.01) | |

(52) U.S. Cl.
CPC ......... *B06B 3/00* (2013.01); *A61B 2017/0011* (2013.01); *A61B 2017/00084* (2013.01); *A61B 2017/00402* (2013.01); *A61B 2017/00504* (2013.01); *A61B 2017/22027* (2013.01); *A61B 2017/320071* (2017.08); *A61B 2017/320084* (2013.01); *A61B 2017/320094* (2017.08)

(58) Field of Classification Search
CPC ........... A61B 2017/00504; A61B 2017/22027; A61B 2017/320084; B06B 1/0611; B06B 3/00
USPC ..... 310/323.18, 323.19, 328, 348, 349, 354, 310/366
See application file for complete search history.

(56) References Cited

U.S. PATENT DOCUMENTS

| | | | |
|---|---|---|---|
| 1,813,902 | A | 7/1931 | Bovie |
| 2,188,497 | A | 1/1940 | Calva |
| 2,366,274 | A | 1/1945 | Luth et al. |
| 2,425,245 | A | 8/1947 | Johnson |
| 2,442,966 | A | 6/1948 | Wallace |
| 2,458,152 | A | 1/1949 | Eakins |
| 2,510,693 | A | 6/1950 | Green |
| 2,597,564 | A | 5/1952 | Bugg |
| 2,704,333 | A | 3/1955 | Calosi et al. |
| 2,736,960 | A | 3/1956 | Armstrong |
| 2,743,726 | A | 5/1956 | Grieshaber |
| 2,748,967 | A | 6/1956 | Roach |
| 2,845,072 | A | 7/1958 | Shafer |
| 2,849,788 | A | 9/1958 | Creek |
| 2,867,039 | A | 1/1959 | Zach |
| 2,874,470 | A | 2/1959 | Richards |
| 2,990,616 | A | 7/1961 | Balamuth et al. |
| RE25,033 | E | 8/1961 | Balamuth et al. |
| 3,015,961 | A | 1/1962 | Roney |
| 3,033,407 | A | 5/1962 | Alfons |
| 3,053,124 | A | 9/1962 | Balamuth et al. |
| 3,082,805 | A | 3/1963 | Royce |
| 3,166,971 | A | 1/1965 | Stoecker |
| 3,322,403 | A | 5/1967 | Murphy |
| 3,432,691 | A | 3/1969 | Shoh |
| 3,433,226 | A | 3/1969 | Boyd |
| 3,489,930 | A | 1/1970 | Shoh |
| 3,503,396 | A | 3/1970 | Pierie et al. |
| 3,503,397 | A | 3/1970 | Fogarty et al. |
| 3,503,398 | A | 3/1970 | Fogarty et al. |
| 3,513,848 | A | 5/1970 | Winston et al. |
| 3,514,856 | A | 6/1970 | Camp et al. |
| 3,525,912 | A | 8/1970 | Wallin |
| 3,526,219 | A | 9/1970 | Balamuth |
| 3,554,198 | A | 1/1971 | Tatoian et al. |
| 3,580,841 | A | 5/1971 | Cadotte et al. |
| 3,606,682 | A | 9/1971 | Camp et al. |
| 3,614,484 | A | 10/1971 | Shoh |
| 3,616,375 | A | 10/1971 | Inoue |
| 3,629,726 | A | 12/1971 | Popescu |
| 3,636,943 | A | 1/1972 | Balamuth |
| 3,668,486 | A | 6/1972 | Silver |
| 3,702,948 | A | 11/1972 | Balamuth |
| 3,703,651 | A | 11/1972 | Blowers |
| 3,776,238 | A | 12/1973 | Peyman et al. |
| 3,777,760 | A | 12/1973 | Essner |
| 3,792,701 | A | 2/1974 | Kloz et al. |
| 3,805,787 | A | 4/1974 | Banko |
| 3,809,977 | A | 5/1974 | Balamuth et al. |
| 3,830,098 | A | 8/1974 | Antonevich |
| 3,832,776 | A | 9/1974 | Sawyer |
| 3,854,737 | A | 12/1974 | Gilliam, Sr. |
| 3,862,630 | A | 1/1975 | Balamuth |
| 3,875,945 | A | 4/1975 | Friedman |
| 3,885,438 | A | 5/1975 | Harris, Sr. et al. |
| 3,900,823 | A | 8/1975 | Sokal et al. |
| 3,918,442 | A | 11/1975 | Nikolaev et al. |
| 3,924,335 | A | 12/1975 | Balamuth et al. |
| 3,946,738 | A | 3/1976 | Newton et al. |
| 3,955,859 | A | 5/1976 | Stella et al. |
| 3,956,826 | A | 5/1976 | Perdreaux, Jr. |
| 3,989,952 | A | 11/1976 | Hohmann |
| 4,005,714 | A | 2/1977 | Hiltebrandt |
| 4,012,647 | A | 3/1977 | Balamuth et al. |
| 4,034,762 | A | 7/1977 | Cosens et al. |
| 4,058,126 | A | 11/1977 | Leveen |
| 4,074,719 | A | 2/1978 | Semm |
| 4,085,893 | A | 4/1978 | Durley, III |
| 4,156,187 | A | 5/1979 | Murry et al. |
| 4,167,944 | A | 9/1979 | Banko |
| 4,169,984 | A * | 10/1979 | Parisi ..................... A61C 17/20 310/323.18 |
| 4,173,725 | A | 11/1979 | Asai et al. |
| 4,188,927 | A | 2/1980 | Harris |
| 4,193,009 | A | 3/1980 | Durley, III |
| 4,200,106 | A | 4/1980 | Douvas et al. |
| 4,203,430 | A | 5/1980 | Takahashi |
| 4,203,444 | A | 5/1980 | Bonnell et al. |
| 4,220,154 | A | 9/1980 | Semm |
| 4,237,441 | A | 12/1980 | van Konynenburg et al. |
| 4,281,785 | A | 8/1981 | Brooks |
| 4,300,083 | A | 11/1981 | Heiges |
| 4,302,728 | A | 11/1981 | Nakamura |
| 4,304,987 | A | 12/1981 | van Konynenburg |
| 4,306,570 | A | 12/1981 | Matthews |
| 4,314,559 | A | 2/1982 | Allen |
| 4,352,459 | A * | 10/1982 | Berger ................ B05B 17/0623 239/102.2 |
| 4,445,063 | A | 4/1984 | Smith |
| 4,452,473 | A | 6/1984 | Ruschke |
| 4,463,759 | A | 8/1984 | Garito et al. |
| 4,491,132 | A | 1/1985 | Aikins |
| 4,492,231 | A | 1/1985 | Auth |
| 4,494,759 | A | 1/1985 | Kieffer |
| 4,504,264 | A | 3/1985 | Kelman |
| 4,512,344 | A | 4/1985 | Barber |
| 4,526,571 | A | 7/1985 | Wuchinich |
| 4,535,773 | A | 8/1985 | Yoon |
| 4,541,638 | A | 9/1985 | Ogawa et al. |
| 4,545,374 | A | 10/1985 | Jacobson |
| 4,545,926 | A | 10/1985 | Fouts, Jr. et al. |
| 4,550,870 | A | 11/1985 | Krumme et al. |
| 4,553,544 | A | 11/1985 | Nomoto et al. |
| 4,562,838 | A | 1/1986 | Walker |
| 4,574,615 | A | 3/1986 | Bower et al. |
| 4,582,236 | A | 4/1986 | Hirose |
| 4,617,927 | A | 10/1986 | Manes |
| 4,633,119 | A | 12/1986 | Thompson |
| 4,633,874 | A | 1/1987 | Chow et al. |
| 4,634,420 | A | 1/1987 | Spinosa et al. |
| 4,640,279 | A | 2/1987 | Beard |
| 4,641,053 | A | 2/1987 | Takeda |
| 4,646,738 | A | 3/1987 | Trott |
| 4,646,756 | A | 3/1987 | Watmough et al. |
| 4,649,919 | A | 3/1987 | Thimsen et al. |
| 4,662,068 | A | 5/1987 | Polonsky |
| 4,663,677 | A | 5/1987 | Griffith et al. |
| 4,674,502 | A | 6/1987 | Imonti |
| 4,696,667 | A | 9/1987 | Masch |
| 4,708,127 | A | 11/1987 | Abdelghani |
| 4,712,722 | A | 12/1987 | Hood et al. |
| 4,735,603 | A | 4/1988 | Goodson et al. |
| 4,750,488 | A | 6/1988 | Wuchinich et al. |

(56) References Cited

U.S. PATENT DOCUMENTS

| | | |
|---|---|---|
| 4,761,871 A | 8/1988 | O'Connor et al. |
| 4,783,997 A | 11/1988 | Lynnworth |
| 4,808,154 A | 2/1989 | Freeman |
| 4,819,635 A | 4/1989 | Shapiro |
| 4,821,719 A | 4/1989 | Fogarty |
| 4,827,911 A | 5/1989 | Broadwin et al. |
| 4,830,462 A | 5/1989 | Karny et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,849,133 A | 7/1989 | Yoshida et al. |
| 4,850,354 A | 7/1989 | McGurk-Burleson et al. |
| 4,852,578 A | 8/1989 | Companion et al. |
| 4,860,745 A | 8/1989 | Farin et al. |
| 4,862,890 A | 9/1989 | Stasz et al. |
| 4,865,159 A | 9/1989 | Jamison |
| 4,867,157 A | 9/1989 | McGurk-Burleson et al. |
| 4,869,715 A | 9/1989 | Sherburne |
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,936,842 A | 6/1990 | D'Amelio et al. |
| 4,954,960 A | 9/1990 | Lo et al. |
| 4,965,532 A | 10/1990 | Sakurai |
| 4,978,067 A * | 12/1990 | Berger ............... B05B 17/0623 239/102.2 |
| 4,979,952 A | 12/1990 | Kubota et al. |
| 4,981,756 A | 1/1991 | Rhandhawa |
| 4,983,160 A | 1/1991 | Steppe et al. |
| 5,013,956 A | 5/1991 | Kurozumi et al. |
| 5,015,227 A | 5/1991 | Broadwin et al. |
| 5,020,514 A | 6/1991 | Heckele |
| 5,026,370 A | 6/1991 | Lottick |
| 5,026,387 A | 6/1991 | Thomas |
| 5,035,695 A | 7/1991 | Weber, Jr. et al. |
| 5,042,461 A | 8/1991 | Inoue et al. |
| 5,042,707 A | 8/1991 | Taheri |
| 5,047,043 A | 9/1991 | Kubota et al. |
| 5,057,119 A | 10/1991 | Clark et al. |
| 5,058,570 A | 10/1991 | Idemoto et al. |
| 5,059,210 A | 10/1991 | Clark et al. |
| 5,061,269 A | 10/1991 | Muller |
| 5,084,052 A | 1/1992 | Jacobs |
| 5,088,687 A | 2/1992 | Stender |
| 5,096,532 A | 3/1992 | Neuwirth et al. |
| 5,099,840 A | 3/1992 | Goble et al. |
| 5,104,025 A | 4/1992 | Main et al. |
| 5,105,117 A | 4/1992 | Yamaguchi |
| 5,106,538 A | 4/1992 | Barma et al. |
| 5,108,383 A | 4/1992 | White |
| 5,109,819 A | 5/1992 | Custer et al. |
| 5,112,300 A | 5/1992 | Ureche |
| 5,123,903 A | 6/1992 | Quaid et al. |
| 5,126,618 A | 6/1992 | Takahashi et al. |
| D327,872 S | 7/1992 | McMills et al. |
| D330,253 S | 10/1992 | Burek |
| 5,152,762 A | 10/1992 | McElhenney |
| 5,156,613 A | 10/1992 | Sawyer |
| 5,156,633 A | 10/1992 | Smith |
| 5,159,226 A | 10/1992 | Montgomery |
| 5,160,334 A | 11/1992 | Billings et al. |
| 5,162,044 A | 11/1992 | Gahn et al. |
| 5,163,421 A | 11/1992 | Bernstein et al. |
| 5,163,537 A | 11/1992 | Radev |
| 5,167,619 A | 12/1992 | Wuchinich |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,190,518 A | 3/1993 | Takasu |
| 5,190,541 A | 3/1993 | Abele et al. |
| 5,196,007 A | 3/1993 | Ellman et al. |
| 5,205,459 A | 4/1993 | Brinkerhoff et al. |
| 5,205,817 A | 4/1993 | Idemoto et al. |
| 5,209,719 A | 5/1993 | Baruch et al. |
| 5,209,776 A | 5/1993 | Bass et al. |
| 5,213,103 A | 5/1993 | Martin et al. |
| 5,213,569 A | 5/1993 | Davis |
| 5,214,339 A | 5/1993 | Naito |
| 5,217,460 A | 6/1993 | Knoepfler |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,234,428 A | 8/1993 | Kaufman |
| 5,234,436 A | 8/1993 | Eaton et al. |
| 5,241,236 A | 8/1993 | Sasaki et al. |
| 5,241,968 A | 9/1993 | Slater |
| 5,242,385 A | 9/1993 | Strukel |
| 5,242,460 A | 9/1993 | Klein et al. |
| 5,254,129 A | 10/1993 | Alexander |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,264,925 A | 11/1993 | Shipp et al. |
| 5,269,297 A | 12/1993 | Weng et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,285,945 A | 2/1994 | Brinkerhoff et al. |
| 5,289,436 A | 2/1994 | Terhune |
| 5,290,286 A | 3/1994 | Parins |
| 5,293,863 A | 3/1994 | Zhu et al. |
| 5,300,068 A | 4/1994 | Rosar et al. |
| 5,304,115 A | 4/1994 | Pflueger et al. |
| 5,306,280 A | 4/1994 | Bregen et al. |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,327 A | 5/1994 | Bales et al. |
| 5,312,425 A | 5/1994 | Evans et al. |
| 5,318,525 A | 6/1994 | West et al. |
| 5,318,563 A | 6/1994 | Malis et al. |
| 5,318,564 A | 6/1994 | Eggers |
| 5,318,570 A | 6/1994 | Hood et al. |
| 5,318,589 A | 6/1994 | Lichtman |
| 5,322,055 A | 6/1994 | Davison et al. |
| 5,323,055 A | 6/1994 | Yamazaki |
| 5,324,297 A | 6/1994 | Hood et al. |
| 5,324,299 A | 6/1994 | Davison et al. |
| 5,326,013 A | 7/1994 | Green et al. |
| 5,326,342 A | 7/1994 | Pflueger et al. |
| 5,330,471 A | 7/1994 | Eggers |
| 5,330,502 A | 7/1994 | Hassler et al. |
| 5,339,723 A | 8/1994 | Huitema |
| 5,342,292 A | 8/1994 | Nita et al. |
| 5,342,359 A | 8/1994 | Rydell |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,354,265 A | 10/1994 | Mackool |
| 5,357,164 A | 10/1994 | Imabayashi et al. |
| 5,357,423 A | 10/1994 | Weaver et al. |
| 5,358,506 A | 10/1994 | Green et al. |

(56) References Cited

U.S. PATENT DOCUMENTS

| | | |
|---|---|---|
| 5,359,994 A | 11/1994 | Krauter et al. |
| 5,361,583 A | 11/1994 | Huitema |
| 5,366,466 A | 11/1994 | Christian et al. |
| 5,368,557 A | 11/1994 | Nita et al. |
| 5,370,645 A | 12/1994 | Klicek et al. |
| 5,371,429 A * | 12/1994 | Manna ................. B06B 1/0618 310/328 |
| 5,372,585 A | 12/1994 | Tiefenbrun et al. |
| 5,374,813 A | 12/1994 | Shipp |
| D354,564 S | 1/1995 | Medema |
| 5,381,067 A | 1/1995 | Greenstein et al. |
| 5,383,874 A | 1/1995 | Jackson et al. |
| 5,383,883 A | 1/1995 | Wilk et al. |
| 5,387,207 A | 2/1995 | Dyer et al. |
| 5,387,215 A | 2/1995 | Fisher |
| 5,389,098 A | 2/1995 | Tsuruta et al. |
| 5,391,144 A | 2/1995 | Sakurai et al. |
| 5,394,187 A | 2/1995 | Shipp |
| 5,395,033 A | 3/1995 | Byrne et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,397,293 A | 3/1995 | Alliger et al. |
| 5,400,267 A | 3/1995 | Denen et al. |
| 5,403,312 A | 4/1995 | Yates et al. |
| 5,403,334 A | 4/1995 | Evans et al. |
| 5,406,503 A | 4/1995 | Williams, Jr. et al. |
| 5,408,268 A | 4/1995 | Shipp |
| 5,409,453 A | 4/1995 | Lundquist et al. |
| D358,887 S | 5/1995 | Feinberg |
| 5,411,481 A | 5/1995 | Allen et al. |
| 5,413,107 A | 5/1995 | Oakley et al. |
| 5,417,709 A | 5/1995 | Slater |
| 5,419,761 A | 5/1995 | Narayanan et al. |
| 5,421,829 A | 6/1995 | Olichney et al. |
| 5,423,844 A | 6/1995 | Miller |
| 5,428,504 A | 6/1995 | Bhatla |
| 5,429,131 A | 7/1995 | Scheinman et al. |
| 5,438,997 A | 8/1995 | Sieben et al. |
| 5,441,499 A | 8/1995 | Fritzsch |
| 5,443,463 A | 8/1995 | Stern et al. |
| 5,445,638 A | 8/1995 | Rydell et al. |
| 5,445,639 A | 8/1995 | Kuslich et al. |
| 5,447,509 A | 9/1995 | Mills et al. |
| 5,449,370 A | 9/1995 | Vaitekunas |
| 5,451,220 A | 9/1995 | Ciervo |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,471,988 A | 12/1995 | Fujio et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,490,860 A | 2/1996 | Middle et al. |
| 5,496,317 A | 3/1996 | Goble et al. |
| 5,496,411 A | 3/1996 | Candy |
| 5,499,992 A | 3/1996 | Meade et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,507,738 A | 4/1996 | Ciervo |
| 5,509,922 A | 4/1996 | Aranyi et al. |
| 5,511,556 A | 4/1996 | DeSantis |
| 5,520,704 A | 5/1996 | Castro et al. |
| 5,522,832 A | 6/1996 | Kugo et al. |
| 5,522,839 A | 6/1996 | Pilling |
| 5,527,273 A | 6/1996 | Manna et al. |
| 5,527,331 A | 6/1996 | Kresch et al. |
| 5,531,744 A | 7/1996 | Nardella et al. |
| 5,540,681 A | 7/1996 | Strul et al. |
| 5,540,693 A | 7/1996 | Fisher |
| 5,542,916 A | 8/1996 | Hirsch et al. |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,562,703 A | 10/1996 | Desai |
| 5,563,179 A | 10/1996 | Stone et al. |
| 5,569,164 A | 10/1996 | Lurz |
| 5,571,121 A | 11/1996 | Heifetz |
| 5,573,424 A | 11/1996 | Poppe |
| 5,573,534 A | 11/1996 | Stone |
| 5,575,799 A | 11/1996 | Bolanos et al. |
| 5,577,654 A | 11/1996 | Bishop |
| 5,582,618 A | 12/1996 | Chin et al. |
| 5,584,830 A | 12/1996 | Ladd et al. |
| 5,591,187 A | 1/1997 | Dekel |
| 5,593,414 A | 1/1997 | Shipp et al. |
| 5,599,350 A | 2/1997 | Schulze et al. |
| 5,601,601 A | 2/1997 | Tal et al. |
| 5,603,773 A | 2/1997 | Campbell |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,304 A | 4/1997 | Hart et al. |
| 5,618,307 A | 4/1997 | Donlon et al. |
| 5,618,492 A | 4/1997 | Auten et al. |
| 5,620,447 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,760 A | 5/1997 | Knoepfler |
| 5,630,420 A | 5/1997 | Vaitekunas |
| 5,632,432 A | 5/1997 | Schulze et al. |
| 5,632,717 A | 5/1997 | Yoon |
| 5,640,741 A | 6/1997 | Yano |
| D381,077 S | 7/1997 | Hunt |
| 5,643,301 A | 7/1997 | Mollenauer |
| 5,647,851 A | 7/1997 | Pokras |
| 5,647,871 A | 7/1997 | Levine et al. |
| 5,649,937 A | 7/1997 | Bito et al. |
| 5,649,955 A | 7/1997 | Hashimoto et al. |
| 5,651,780 A | 7/1997 | Jackson et al. |
| 5,653,713 A | 8/1997 | Michelson |
| 5,658,281 A | 8/1997 | Heard |
| 5,662,662 A | 9/1997 | Bishop et al. |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,678,568 A | 10/1997 | Uchikubo et al. |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,704,791 A | 1/1998 | Gillio |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,716,366 A | 2/1998 | Yates |
| 5,717,306 A | 2/1998 | Shipp |
| 5,720,742 A | 2/1998 | Zacharias |
| 5,720,744 A | 2/1998 | Eggleston et al. |
| 5,722,980 A | 3/1998 | Schulz et al. |
| 5,728,130 A | 3/1998 | Ishikawa et al. |

(56) References Cited

U.S. PATENT DOCUMENTS

| | | |
|---|---|---|
| 5,730,752 A | 3/1998 | Alden et al. |
| 5,733,074 A | 3/1998 | Stock et al. |
| 5,735,848 A | 4/1998 | Yates et al. |
| 5,735,875 A | 4/1998 | Bonutti et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,766,164 A | 6/1998 | Mueller et al. |
| 5,772,659 A | 6/1998 | Becker et al. |
| 5,776,130 A | 7/1998 | Buysse et al. |
| 5,776,155 A | 7/1998 | Beaupre et al. |
| 5,779,130 A | 7/1998 | Alesi et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,792,165 A | 8/1998 | Klieman et al. |
| 5,796,188 A | 8/1998 | Bays |
| 5,797,941 A | 8/1998 | Schulze et al. |
| 5,797,959 A | 8/1998 | Castro et al. |
| 5,800,432 A | 9/1998 | Swanson |
| 5,800,448 A | 9/1998 | Banko |
| 5,800,449 A | 9/1998 | Wales |
| 5,805,140 A | 9/1998 | Rosenberg et al. |
| 5,807,310 A | 9/1998 | Hood |
| 5,807,393 A | 9/1998 | Williamson, IV et al. |
| 5,808,396 A | 9/1998 | Boukhny |
| 5,810,811 A | 9/1998 | Yates et al. |
| 5,810,828 A | 9/1998 | Lightman et al. |
| 5,810,859 A | 9/1998 | DiMatteo et al. |
| 5,810,869 A | 9/1998 | Kaplan et al. |
| 5,817,033 A | 10/1998 | DeSantis et al. |
| 5,817,084 A | 10/1998 | Jensen |
| 5,817,093 A | 10/1998 | Williamson, IV et al. |
| 5,817,119 A | 10/1998 | Klieman et al. |
| 5,823,197 A | 10/1998 | Edwards |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,290 A | 12/1998 | Winston |
| 5,853,412 A | 12/1998 | Mayenberger |
| 5,858,018 A | 1/1999 | Shipp et al. |
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,363 A | 3/1999 | Urich |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,893,880 A | 4/1999 | Egan et al. |
| 5,895,412 A | 4/1999 | Tucker |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,625 A | 5/1999 | Bito et al. |
| 5,906,627 A | 5/1999 | Spaulding |
| 5,906,628 A | 5/1999 | Miyawaki et al. |
| 5,910,129 A | 6/1999 | Koblish et al. |
| 5,910,150 A | 6/1999 | Saadat |
| 5,911,699 A | 6/1999 | Anis et al. |
| 5,916,229 A | 6/1999 | Evans |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,941,887 A | 8/1999 | Steen et al. |
| 5,944,718 A | 8/1999 | Austin et al. |
| 5,944,737 A | 8/1999 | Tsonton et al. |
| 5,947,984 A | 9/1999 | Whipple |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,971,949 A | 10/1999 | Levin et al. |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,984,938 A | 11/1999 | Yoon |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,001,120 A | 12/1999 | Levin |
| 6,003,517 A | 12/1999 | Sheffield et al. |
| 6,004,335 A | 12/1999 | Vaitekunas et al. |
| 6,007,552 A | 12/1999 | Fogarty et al. |
| 6,013,052 A | 1/2000 | Durman et al. |
| 6,024,741 A | 2/2000 | Williamson, IV et al. |
| 6,024,744 A | 2/2000 | Kese et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,039,734 A | 3/2000 | Goble |
| 6,048,224 A | 4/2000 | Kay |
| 6,050,943 A | 4/2000 | Slayton et al. |
| 6,050,996 A | 4/2000 | Schmaltz et al. |
| 6,051,010 A | 4/2000 | DiMatteo et al. |
| 6,053,906 A | 4/2000 | Honda et al. |
| 6,056,735 A | 5/2000 | Okada et al. |
| 6,063,050 A | 5/2000 | Manna et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,096,033 A | 8/2000 | Tu et al. |
| 6,099,483 A | 8/2000 | Palmer et al. |
| 6,099,542 A | 8/2000 | Cohn et al. |
| 6,099,550 A | 8/2000 | Yoon |
| 6,109,500 A | 8/2000 | Alli et al. |
| 6,110,127 A | 8/2000 | Suzuki |
| 6,113,594 A | 9/2000 | Savage |
| 6,113,598 A | 9/2000 | Baker |
| 6,117,152 A | 9/2000 | Huitema |
| 6,120,519 A | 9/2000 | Weber et al. |
| H1904 H | 10/2000 | Yates et al. |
| 6,126,629 A | 10/2000 | Perkins |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,448 A | 10/2000 | Perez et al. |
| 6,139,320 A | 10/2000 | Hahn |
| 6,139,561 A | 10/2000 | Shibata et al. |

(56) References Cited

U.S. PATENT DOCUMENTS

| | | |
|---|---|---|
| 6,142,615 A | 11/2000 | Qiu et al. |
| 6,142,994 A | 11/2000 | Swanson et al. |
| 6,144,402 A | 11/2000 | Norsworthy et al. |
| 6,147,560 A | 11/2000 | Erhage et al. |
| 6,152,902 A | 11/2000 | Christian et al. |
| 6,152,923 A | 11/2000 | Ryan |
| 6,154,198 A | 11/2000 | Rosenberg |
| 6,156,029 A | 12/2000 | Mueller |
| 6,159,160 A | 12/2000 | Hsei et al. |
| 6,159,175 A | 12/2000 | Strukel et al. |
| 6,162,194 A | 12/2000 | Shipp |
| 6,162,208 A | 12/2000 | Hipps |
| 6,165,150 A | 12/2000 | Banko |
| 6,165,186 A | 12/2000 | Fogarty et al. |
| 6,165,191 A | 12/2000 | Shibata et al. |
| 6,174,309 B1 | 1/2001 | Wrublewski et al. |
| 6,174,310 B1 | 1/2001 | Kirwan, Jr. |
| 6,176,857 B1 | 1/2001 | Ashley |
| 6,179,853 B1 | 1/2001 | Sachse et al. |
| 6,183,426 B1 | 2/2001 | Akisada et al. |
| 6,187,003 B1 | 2/2001 | Buysse et al. |
| 6,190,386 B1 | 2/2001 | Rydell |
| 6,193,709 B1 | 2/2001 | Miyawaki et al. |
| 6,204,592 B1 | 3/2001 | Hur |
| 6,205,855 B1 | 3/2001 | Pfeiffer |
| 6,206,844 B1 | 3/2001 | Reichel et al. |
| 6,206,876 B1 | 3/2001 | Levine et al. |
| 6,206,877 B1 | 3/2001 | Kese et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,217,591 B1 | 4/2001 | Egan et al. |
| 6,228,080 B1 | 5/2001 | Gines |
| 6,228,104 B1 | 5/2001 | Fogarty et al. |
| 6,231,565 B1 | 5/2001 | Tovey et al. |
| 6,233,476 B1 | 5/2001 | Strommer et al. |
| 6,238,366 B1 | 5/2001 | Savage et al. |
| 6,241,724 B1 | 6/2001 | Fleischman et al. |
| 6,245,065 B1 | 6/2001 | Panescu et al. |
| 6,251,110 B1 | 6/2001 | Wampler |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,259,230 B1 | 7/2001 | Chou |
| 6,267,761 B1 | 7/2001 | Ryan |
| 6,270,471 B1 | 8/2001 | Hechel et al. |
| 6,270,831 B2 | 8/2001 | Kumar et al. |
| 6,273,852 B1 | 8/2001 | Lehe et al. |
| 6,273,902 B1 | 8/2001 | Fogarty et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,292,700 B1 | 9/2001 | Morrison et al. |
| 6,293,954 B1 | 9/2001 | Fogarty et al. |
| 6,299,591 B1 | 10/2001 | Banko |
| 6,299,621 B1 | 10/2001 | Fogarty et al. |
| 6,306,131 B1 | 10/2001 | Hareyama et al. |
| 6,306,157 B1 | 10/2001 | Shchervinsky |
| 6,309,400 B2 | 10/2001 | Beaupre |
| 6,311,783 B1 | 11/2001 | Harpell |
| 6,312,445 B1 | 11/2001 | Fogarty et al. |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,333,488 B1 | 12/2001 | Lawrence et al. |
| 6,338,657 B1 | 1/2002 | Harper et al. |
| 6,340,352 B1 | 1/2002 | Okada et al. |
| 6,340,878 B1 | 1/2002 | Oglesbee |
| 6,350,269 B1 | 2/2002 | Shipp et al. |
| 6,352,532 B1 | 3/2002 | Kramer et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,094 B1 | 5/2002 | Eitenmuller |
| 6,387,109 B1 | 5/2002 | Davison et al. |
| 6,387,112 B1 | 5/2002 | Fogarty et al. |
| 6,388,657 B1 | 5/2002 | Natoli |
| 6,391,026 B1 | 5/2002 | Hung et al. |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,733 B1 | 6/2002 | Fogarty et al. |
| 6,409,722 B1 | 6/2002 | Hoey et al. |
| 6,409,743 B1 | 6/2002 | Fenton, Jr. |
| H2037 H | 7/2002 | Yates et al. |
| 6,416,469 B1 | 7/2002 | Phung et al. |
| 6,416,486 B1 | 7/2002 | Wampler |
| 6,416,525 B1 | 7/2002 | Shibata |
| 6,419,675 B1 | 7/2002 | Gallo, Sr. |
| 6,423,073 B2 | 7/2002 | Bowman |
| 6,423,082 B1 | 7/2002 | Houser et al. |
| 6,425,906 B1 | 7/2002 | Young et al. |
| 6,425,907 B1 | 7/2002 | Shibata et al. |
| 6,428,538 B1 | 8/2002 | Blewett et al. |
| 6,428,539 B1 | 8/2002 | Baxter et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,468,286 B2 | 10/2002 | Mastri et al. |
| 6,475,211 B2 | 11/2002 | Chess et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,690 B1 | 12/2002 | Goble et al. |
| 6,491,701 B2 | 12/2002 | Tierney et al. |
| 6,491,708 B2 | 12/2002 | Madan et al. |
| 6,497,715 B2 | 12/2002 | Satou |
| 6,498,421 B1 | 12/2002 | Oh et al. |
| 6,500,112 B1 | 12/2002 | Khouri |
| 6,500,176 B1 | 12/2002 | Truckai et al. |
| 6,500,188 B2 | 12/2002 | Harper et al. |
| 6,500,312 B2 | 12/2002 | Wedekamp |
| 6,503,248 B1 | 1/2003 | Levine |
| 6,506,208 B2 | 1/2003 | Hunt et al. |
| 6,511,478 B1 | 1/2003 | Burnside et al. |
| 6,511,480 B1 | 1/2003 | Tetzlaff et al. |
| 6,511,493 B1 | 1/2003 | Moutafis et al. |
| 6,514,252 B2 | 2/2003 | Nezhat et al. |
| 6,514,267 B2 | 2/2003 | Jewett |
| 6,517,565 B1 | 2/2003 | Whitman et al. |
| 6,524,251 B2 | 2/2003 | Rabiner et al. |
| 6,524,316 B1 | 2/2003 | Nicholson et al. |
| 6,526,976 B1 | 3/2003 | Baran |
| 6,527,736 B1 | 3/2003 | Attinger et al. |

(56) References Cited

U.S. PATENT DOCUMENTS

| | | |
|---|---|---|
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,035 B1 | 5/2003 | Levin |
| 6,562,037 B2 | 5/2003 | Paton et al. |
| 6,562,059 B2 | 5/2003 | Edwards et al. |
| 6,565,558 B1 | 5/2003 | Lindenmeier et al. |
| 6,569,109 B2 | 5/2003 | Sakurai et al. |
| 6,569,178 B1 | 5/2003 | Miyawaki et al. |
| 6,572,563 B2 | 6/2003 | Ouchi |
| 6,572,632 B2 | 6/2003 | Zisterer et al. |
| 6,572,639 B1 | 6/2003 | Ingle et al. |
| 6,575,929 B2 | 6/2003 | Sussman et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| 6,584,360 B2 | 6/2003 | Francischelli et al. |
| D477,408 S | 7/2003 | Bromley |
| 6,585,735 B1 | 7/2003 | Frazier et al. |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,599,288 B2 | 7/2003 | Maguire et al. |
| 6,602,229 B2 | 8/2003 | Coss |
| 6,602,252 B2 | 8/2003 | Mollenauer |
| 6,607,540 B1 | 8/2003 | Shipp |
| 6,610,059 B1 | 8/2003 | West, Jr. |
| 6,610,060 B2 | 8/2003 | Mulier et al. |
| 6,616,450 B2 | 9/2003 | Mossle et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,444 B2 | 9/2003 | Babaev |
| 6,623,482 B2 | 9/2003 | Pendekanti et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,648,839 B2 | 11/2003 | Manna et al. |
| 6,648,883 B2 | 11/2003 | Francischelli et al. |
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,124 B2 | 12/2003 | Flesch et al. |
| 6,656,132 B1 | 12/2003 | Ouchi |
| 6,656,177 B2 | 12/2003 | Truckai et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,696 B2 | 12/2003 | Bacher et al. |
| 6,669,710 B2 | 12/2003 | Moutafis et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,701 B2 | 2/2004 | Orszulak et al. |
| 6,685,703 B2 | 2/2004 | Pearson et al. |
| 6,689,086 B1 | 2/2004 | Nita et al. |
| 6,689,145 B2 | 2/2004 | Lee et al. |
| 6,689,146 B1 | 2/2004 | Himes |
| 6,690,960 B2 | 2/2004 | Chen et al. |
| 6,695,782 B2 | 2/2004 | Ranucci et al. |
| 6,695,840 B2 | 2/2004 | Schulze |
| 6,699,214 B2 | 3/2004 | Gellman |
| 6,702,761 B1 | 3/2004 | Damadian et al. |
| 6,702,821 B2 | 3/2004 | Bonutti |
| 6,712,805 B2 | 3/2004 | Weimann |
| 6,716,215 B1 | 4/2004 | David et al. |
| 6,719,692 B2 | 4/2004 | Kleffner et al. |
| 6,719,765 B2 | 4/2004 | Bonutti |
| 6,719,766 B1 | 4/2004 | Buelna et al. |
| 6,719,776 B2 | 4/2004 | Baxter et al. |
| 6,722,552 B2 | 4/2004 | Fenton, Jr. |
| 6,723,091 B2 | 4/2004 | Goble et al. |
| D490,059 S | 5/2004 | Conway et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,154 B2 | 6/2004 | Fogarty et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 | 9/2004 | Araki et al. |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,811,842 B1 | 11/2004 | Ehrnsperger et al. |
| 6,814,731 B2 | 11/2004 | Swanson |
| 6,821,273 B2 | 11/2004 | Mollenauer |
| 6,827,712 B2 | 12/2004 | Tovey et al. |
| 6,828,712 B2 | 12/2004 | Battaglin et al. |
| 6,832,988 B2 | 12/2004 | Sproul |
| 6,835,082 B2 | 12/2004 | Gonnering |
| 6,835,199 B2 | 12/2004 | McGuckin, Jr. et al. |
| 6,840,938 B1 | 1/2005 | Morley et al. |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,221 B1 | 5/2005 | Baillargeon et al. |
| 6,887,252 B1 | 5/2005 | Okada et al. |

(56) References Cited

U.S. PATENT DOCUMENTS

| | | |
|---|---|---|
| 6,893,435 B2 | 5/2005 | Goble |
| 6,899,685 B2 | 5/2005 | Kermode et al. |
| 6,905,497 B2 | 6/2005 | Truckai et al. |
| 6,908,463 B2 | 6/2005 | Treat et al. |
| 6,908,466 B1 | 6/2005 | Bonutti et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckai et al. |
| 6,932,876 B1 | 8/2005 | Statnikov |
| 6,933,656 B2 | 8/2005 | Matsushita et al. |
| D509,589 S | 9/2005 | Wells |
| 6,942,660 B2 | 9/2005 | Pantera et al. |
| 6,942,676 B2 | 9/2005 | Buelna |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| 6,958,070 B2 | 10/2005 | Witt et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,988,295 B2 | 1/2006 | Tillim |
| 6,989,017 B2 | 1/2006 | Howell et al. |
| 6,994,708 B2 | 2/2006 | Manzo |
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,382 B2 | 2/2006 | Gallo, Sr. |
| 7,002,283 B2 | 2/2006 | Li et al. |
| 7,004,951 B2 | 2/2006 | Gibbens, III |
| 7,011,657 B2 | 3/2006 | Truckai et al. |
| 7,014,638 B2 | 3/2006 | Michelson |
| 7,018,354 B2 | 3/2006 | Tazi |
| 7,018,389 B2 | 3/2006 | Camerlengo |
| 7,033,357 B2 | 4/2006 | Baxter et al. |
| 7,037,306 B2 | 5/2006 | Podany et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,052,494 B2 | 5/2006 | Goble et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,075 B2 | 8/2006 | Swayze et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,119,516 B2 | 10/2006 | Denning |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,131,983 B2 | 11/2006 | Murakami |
| 7,135,018 B2 | 11/2006 | Ryan et al. |
| 7,135,029 B2 | 11/2006 | Makin et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,201 B2 | 1/2007 | Peshkovskiy et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,259 B2 | 1/2007 | Tardy et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,169,144 B2 | 1/2007 | Hoey et al. |
| 7,169,146 B2 | 1/2007 | Truckai et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,182,762 B2 | 2/2007 | Bortkiewicz |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,208,005 B2 | 4/2007 | Frecker et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,667 B2 | 8/2007 | Moses et al. |
| 7,258,688 B1 | 8/2007 | Shah et al. |
| 7,264,618 B2 | 9/2007 | Murakami et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,282,836 B2 | 10/2007 | Kwon et al. |
| 7,285,895 B2 | 10/2007 | Beaupre |
| 7,287,682 B1 | 10/2007 | Ezzat et al. |

(56) References Cited

U.S. PATENT DOCUMENTS

| | | |
|---|---|---|
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,318,832 B2 | 1/2008 | Young et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,338,463 B2 | 3/2008 | Vigil |
| 7,353,068 B2 | 4/2008 | Tanaka et al. |
| 7,354,440 B2 | 4/2008 | Truckal et al. |
| 7,357,287 B2 | 4/2008 | Shelton, IV et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,413,123 B2 | 8/2008 | Ortenzi |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| D578,643 S | 10/2008 | Shumer et al. |
| D578,644 S | 10/2008 | Shumer et al. |
| D578,645 S | 10/2008 | Shumer et al. |
| 7,431,694 B2 | 10/2008 | Stefanchik et al. |
| 7,431,704 B2 | 10/2008 | Babaev |
| 7,435,582 B2 | 10/2008 | Zimmermann et al. |
| 7,441,684 B2 | 10/2008 | Shelton, IV et al. |
| 7,442,168 B2 | 10/2008 | Novak et al. |
| 7,442,193 B2 | 10/2008 | Shields et al. |
| 7,445,621 B2 | 11/2008 | Dumbauld et al. |
| 7,449,004 B2 | 11/2008 | Yamada et al. |
| 7,451,904 B2 | 11/2008 | Shelton, IV |
| 7,455,208 B2 | 11/2008 | Wales et al. |
| 7,455,641 B2 | 11/2008 | Yamada et al. |
| 7,462,181 B2 | 12/2008 | Kraft et al. |
| 7,464,846 B2 | 12/2008 | Shelton, IV et al. |
| 7,472,815 B2 | 1/2009 | Shelton, IV et al. |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |
| 7,491,201 B2 | 2/2009 | Shields et al. |
| 7,491,202 B2 | 2/2009 | Odom et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,520,865 B2 | 4/2009 | Radley Young et al. |
| 7,524,320 B2 | 4/2009 | Tierney et al. |
| 7,530,986 B2 | 5/2009 | Beaupre et al. |
| 7,533,830 B1 | 5/2009 | Rose |
| 7,534,243 B1 | 5/2009 | Chin et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,559,450 B2 | 7/2009 | Wales et al. |
| 7,559,452 B2 | 7/2009 | Wales et al. |
| 7,563,259 B2 | 7/2009 | Takahashi |
| 7,563,269 B2 | 7/2009 | Hashiguchi |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,166 B2 | 8/2009 | Ethridge et al. |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,601,119 B2 | 10/2009 | Shahinian |
| 7,604,150 B2 | 10/2009 | Boudreaux |
| 7,607,557 B2 | 10/2009 | Shelton, IV et al. |
| 7,608,054 B2 | 10/2009 | Soring et al. |
| 7,617,961 B2 | 11/2009 | Viola |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,245 B2 | 1/2010 | Sekino et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,654,431 B2 | 2/2010 | Hueil et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,125 B2 | 3/2010 | Shipp |
| 7,682,366 B2 | 3/2010 | Sakurai et al. |
| 7,686,763 B2 | 3/2010 | Vaezy et al. |
| 7,686,770 B2 | 3/2010 | Cohen |
| 7,686,826 B2 | 3/2010 | Lee et al. |
| 7,688,028 B2 | 3/2010 | Phillips et al. |

(56) References Cited

U.S. PATENT DOCUMENTS

| | | |
|---|---|---|
| 7,691,095 B2 | 4/2010 | Bednarek et al. |
| 7,691,098 B2 | 4/2010 | Wallace et al. |
| 7,699,846 B2 | 4/2010 | Ryan |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,713,202 B2 | 5/2010 | Boukhny et al. |
| 7,713,267 B2 | 5/2010 | Pozzato |
| 7,714,481 B2 | 5/2010 | Sakai |
| 7,717,312 B2 | 5/2010 | Beetel |
| 7,717,914 B2 | 5/2010 | Kimura |
| 7,717,915 B2 | 5/2010 | Miyazawa |
| 7,721,935 B2 | 5/2010 | Racenet et al. |
| 7,722,527 B2 | 5/2010 | Bouchier et al. |
| 7,722,607 B2 | 5/2010 | Dumbauld et al. |
| D618,797 S | 6/2010 | Price et al. |
| 7,726,537 B2 | 6/2010 | Olson et al. |
| 7,727,177 B2 | 6/2010 | Bayat |
| 7,734,476 B2 | 6/2010 | Wildman et al. |
| 7,738,969 B2 | 6/2010 | Bleich |
| 7,740,594 B2 | 6/2010 | Hibner |
| 7,749,240 B2 | 7/2010 | Takahashi et al. |
| 7,749,273 B2 | 7/2010 | Cauthen, III et al. |
| 7,751,115 B2 | 7/2010 | Song |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,762,979 B2 | 7/2010 | Wuchinich |
| D621,503 S | 8/2010 | Otten et al. |
| 7,766,210 B2 | 8/2010 | Shelton, IV et al. |
| 7,766,693 B2 | 8/2010 | Sartor et al. |
| 7,766,910 B2 | 8/2010 | Hixson et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |
| 7,776,037 B2 | 8/2010 | Odom |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,662 B2 | 8/2010 | Wales et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,045 B2 | 9/2010 | Masuda |
| 7,803,152 B2 | 9/2010 | Honda et al. |
| 7,803,156 B2 | 9/2010 | Eder et al. |
| 7,803,168 B2 | 9/2010 | Gifford et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,815,641 B2 | 10/2010 | Dodde et al. |
| 7,815,658 B2 | 10/2010 | Murakami |
| 7,819,298 B2 | 10/2010 | Hall et al. |
| 7,819,299 B2 | 10/2010 | Shelton, IV et al. |
| 7,819,819 B2 | 10/2010 | Quick et al. |
| 7,819,872 B2 | 10/2010 | Johnson et al. |
| 7,821,143 B2 | 10/2010 | Wiener |
| D627,066 S | 11/2010 | Romero |
| 7,824,401 B2 | 11/2010 | Manzo et al. |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,846,160 B2 | 12/2010 | Payne et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,867,228 B2 | 1/2011 | Nobis et al. |
| 7,871,392 B2 | 1/2011 | Sartor |
| 7,871,423 B2 | 1/2011 | Livneh |
| 7,876,030 B2 | 1/2011 | Taki et al. |
| D631,965 S | 2/2011 | Price et al. |
| 7,878,991 B2 | 2/2011 | Babaev |
| 7,879,033 B2 | 2/2011 | Sartor et al. |
| 7,879,035 B2 | 2/2011 | Garrison et al. |
| 7,879,070 B2 | 2/2011 | Ortiz et al. |
| 7,883,465 B2 | 2/2011 | Donofrio et al. |
| 7,883,475 B2 | 2/2011 | Dupont et al. |
| 7,892,606 B2 | 2/2011 | Thies et al. |
| 7,896,875 B2 | 3/2011 | Heim et al. |
| 7,897,792 B2 | 3/2011 | Iikura et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,909,824 B2 | 3/2011 | Masuda et al. |
| 7,918,848 B2 | 4/2011 | Lau et al. |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,922,716 B2 | 4/2011 | Malecki et al. |
| 7,931,611 B2 | 4/2011 | Novak et al. |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,936,203 B2 | 5/2011 | Zimlich |
| 7,951,095 B2 | 5/2011 | Makin et al. |
| 7,951,165 B2 | 5/2011 | Golden et al. |
| 7,955,331 B2 | 6/2011 | Truckai et al. |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,972,329 B2 | 7/2011 | Refior et al. |
| 7,976,544 B2 | 7/2011 | McClurken et al. |
| 7,980,443 B2 | 7/2011 | Scheib et al. |
| 7,981,050 B2 | 7/2011 | Ritchart et al. |
| 7,981,113 B2 | 7/2011 | Truckai et al. |
| 7,997,278 B2 | 8/2011 | Utley et al. |
| 7,998,157 B2 | 8/2011 | Culp et al. |
| 8,002,732 B2 | 8/2011 | Visconti |
| 8,016,843 B2 | 9/2011 | Escaf |
| 8,020,743 B2 | 9/2011 | Shelton, IV |
| 8,025,630 B2 | 9/2011 | Murakami et al. |
| 8,028,885 B2 | 10/2011 | Smith et al. |
| 8,033,173 B2 | 10/2011 | Ehlert et al. |
| 8,038,693 B2 | 10/2011 | Allen |
| 8,048,070 B2 | 11/2011 | O'Brien et al. |
| 8,052,672 B2 | 11/2011 | Laufer et al. |
| 8,056,720 B2 | 11/2011 | Hawkes |
| 8,057,467 B2 | 11/2011 | Faller et al. |
| 8,057,468 B2 | 11/2011 | Konesky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |
| 8,075,555 B2 | 12/2011 | Truckai et al. |
| 8,075,558 B2 | 12/2011 | Truckai et al. |
| 8,089,197 B2 | 1/2012 | Rinner et al. |
| 8,092,475 B2 | 1/2012 | Cotter et al. |
| 8,097,012 B2 | 1/2012 | Kagarise |
| 8,100,894 B2 | 1/2012 | Mucko et al. |

(56) References Cited

U.S. PATENT DOCUMENTS

| | | |
|---|---|---|
| 8,105,230 B2 | 1/2012 | Honda et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,128,624 B2 | 3/2012 | Couture et al. |
| 8,133,218 B2 | 3/2012 | Daw et al. |
| 8,136,712 B2 | 3/2012 | Zingman |
| 8,137,263 B2 | 3/2012 | Marescaux et al. |
| 8,141,762 B2 | 3/2012 | Bedi et al. |
| 8,142,421 B2 | 3/2012 | Cooper et al. |
| 8,142,461 B2 | 3/2012 | Houser et al. |
| 8,147,488 B2 | 4/2012 | Masuda |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,501 B2 | 5/2012 | Houser et al. |
| 8,182,502 B2 | 5/2012 | Stulen et al. |
| 8,186,560 B2 | 5/2012 | Hess et al. |
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,207,651 B2 | 6/2012 | Gilbert |
| 8,210,411 B2 | 7/2012 | Yates et al. |
| 8,221,306 B2 | 7/2012 | Okada et al. |
| 8,221,415 B2 | 7/2012 | Francischelli |
| 8,226,665 B2 | 7/2012 | Cohen |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,618 B2 | 8/2012 | Bucciaglia et al. |
| 8,246,642 B2 | 8/2012 | Houser et al. |
| 8,251,994 B2 | 8/2012 | McKenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |
| 8,267,300 B2 | 9/2012 | Boudreaux |
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,298,223 B2 | 10/2012 | Wham et al. |
| 8,298,225 B2 | 10/2012 | Gilbert |
| 8,298,232 B2 | 10/2012 | Unger |
| 8,298,233 B2 | 10/2012 | Mueller |
| 8,303,576 B2 | 11/2012 | Brock |
| 8,303,580 B2 | 11/2012 | Wham et al. |
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,967 B2 | 1/2013 | Stulen |
| 8,353,297 B2 | 1/2013 | Dacquay et al. |
| 8,357,103 B2 | 1/2013 | Mark et al. |
| 8,357,158 B2 | 1/2013 | McKenna et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,394,096 B2 | 3/2013 | Moses et al. |
| 8,394,115 B2 | 3/2013 | Houser et al. |
| 8,397,971 B2 | 3/2013 | Yates et al. |
| 8,403,926 B2 | 3/2013 | Nobis et al. |
| 8,403,945 B2 | 3/2013 | Whitfield et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,234 B2 | 4/2013 | Stahler et al. |
| 8,414,577 B2 | 4/2013 | Boudreaux et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,423,182 B2 | 4/2013 | Robinson et al. |
| 8,425,161 B2 | 4/2013 | Nagaya et al. |
| 8,425,410 B2 | 4/2013 | Murray et al. |
| 8,425,545 B2 | 4/2013 | Smith et al. |
| 8,430,811 B2 | 4/2013 | Hess et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,435,258 B2 | 5/2013 | Young et al. |
| 8,439,912 B2 | 5/2013 | Cunningham et al. |
| 8,439,939 B2 | 5/2013 | Deville et al. |
| 8,444,637 B2 | 5/2013 | Podmore et al. |
| 8,444,662 B2 | 5/2013 | Palmer et al. |
| 8,444,663 B2 | 5/2013 | Houser et al. |
| 8,444,664 B2 | 5/2013 | Balanev et al. |
| 8,453,906 B2 | 6/2013 | Huang et al. |
| 8,454,599 B2 | 6/2013 | Inagaki et al. |

(56) References Cited

U.S. PATENT DOCUMENTS

| | | | |
|---|---|---|---|
| 8,454,639 B2 | 6/2013 | Du et al. |
| 8,460,288 B2 | 6/2013 | Tamai et al. |
| 8,460,292 B2 | 6/2013 | Truckai et al. |
| 8,460,326 B2 | 6/2013 | Houser et al. |
| 8,461,744 B2 | 6/2013 | Wiener et al. |
| 8,469,981 B2 | 6/2013 | Robertson et al. |
| 8,479,969 B2 | 7/2013 | Shelton, IV |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| 8,491,625 B2 | 7/2013 | Homer |
| 8,496,682 B2 | 7/2013 | Guerra et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,336 B2 | 8/2013 | Couture |
| 8,512,359 B2 | 8/2013 | Whitman et al. |
| 8,512,364 B2 | 8/2013 | Kowalski et al. |
| 8,512,365 B2 | 8/2013 | Wiener et al. |
| 8,518,067 B2 | 8/2013 | Masuda et al. |
| 8,523,889 B2 | 9/2013 | Stulen et al. |
| 8,528,563 B2 | 9/2013 | Gruber |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,546,996 B2 | 10/2013 | Messerly et al. |
| 8,546,999 B2 | 10/2013 | Houser et al. |
| 8,551,077 B2 | 10/2013 | Main et al. |
| 8,551,086 B2 | 10/2013 | Kimura et al. |
| 8,562,592 B2 | 10/2013 | Conlon et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,400 B2 | 10/2013 | Gilbert |
| 8,568,412 B2 | 10/2013 | Brandt et al. |
| 8,569,997 B2 | 10/2013 | Lee |
| 8,573,461 B2 | 11/2013 | Shelton, IV et al. |
| 8,573,465 B2 | 11/2013 | Shelton, IV |
| 8,574,231 B2 | 11/2013 | Boudreaux et al. |
| 8,574,253 B2 | 11/2013 | Gruber et al. |
| 8,579,176 B2 | 11/2013 | Smith et al. |
| 8,579,897 B2 | 11/2013 | Vakharia et al. |
| 8,579,928 B2 | 11/2013 | Robertson et al. |
| 8,579,937 B2 | 11/2013 | Gresham |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,597,193 B2 | 12/2013 | Grunwald et al. |
| 8,602,031 B2 | 12/2013 | Reis et al. |
| 8,602,288 B2 | 12/2013 | Shelton, IV et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,628,534 B2 | 1/2014 | Jones et al. |
| 8,632,461 B2 | 1/2014 | Glossop |
| 8,636,736 B2 | 1/2014 | Yates et al. |
| 8,638,428 B2 | 1/2014 | Brown |
| 8,640,788 B2 | 2/2014 | Dachs, II et al. |
| 8,641,663 B2 | 2/2014 | Kirschenman et al. |
| 8,647,350 B2 | 2/2014 | Mohan et al. |
| 8,650,728 B2 | 2/2014 | Wan et al. |
| 8,651,230 B2 | 2/2014 | Peshkovsky et al. |
| 8,652,120 B2 | 2/2014 | Giordano et al. |
| 8,652,132 B2 | 2/2014 | Tsuchiya et al. |
| 8,652,155 B2 | 2/2014 | Houser et al. |
| 8,659,208 B1 | 2/2014 | Rose et al. |
| 8,663,220 B2 | 3/2014 | Wiener et al. |
| 8,663,222 B2 | 3/2014 | Anderson et al. |
| 8,663,262 B2 | 3/2014 | Smith et al. |
| 8,668,691 B2 | 3/2014 | Heard |
| 8,668,710 B2 | 3/2014 | Slipszenko et al. |
| 8,684,253 B2 | 4/2014 | Giordano et al. |
| 8,685,016 B2 | 4/2014 | Wham et al. |
| 8,685,020 B2 | 4/2014 | Weizman et al. |
| 8,690,582 B2 | 4/2014 | Rohrbach et al. |
| 8,691,268 B2 | 4/2014 | Weimann |
| 8,695,866 B2 | 4/2014 | Leimbach et al. |
| 8,696,366 B2 | 4/2014 | Chen et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,704,425 B2 | 4/2014 | Giordano et al. |
| 8,708,213 B2 | 4/2014 | Shelton, IV et al. |
| 8,709,031 B2 | 4/2014 | Stulen |
| 8,709,035 B2 | 4/2014 | Johnson et al. |
| 8,715,270 B2 | 5/2014 | Weitzner et al. |
| 8,715,277 B2 | 5/2014 | Weizman |
| 8,715,306 B2 | 5/2014 | Faller et al. |
| 8,721,640 B2 | 5/2014 | Taylor et al. |
| 8,721,657 B2 | 5/2014 | Kondoh et al. |
| 8,734,443 B2 | 5/2014 | Hixson et al. |
| 8,734,476 B2 | 5/2014 | Rhee et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,749,116 B2 | 6/2014 | Messerly et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,758,342 B2 | 6/2014 | Bales et al. |
| 8,758,352 B2 | 6/2014 | Cooper et al. |
| 8,764,735 B2 | 7/2014 | Coe et al. |
| 8,764,747 B2 | 7/2014 | Cummings et al. |
| 8,767,970 B2 | 7/2014 | Eppolito |
| 8,770,459 B2 | 7/2014 | Racenet et al. |
| 8,771,269 B2 | 7/2014 | Sherman et al. |
| 8,771,270 B2 | 7/2014 | Burbank |
| 8,773,001 B2 | 7/2014 | Wiener et al. |
| 8,777,944 B2 | 7/2014 | Frankhouser et al. |
| 8,779,648 B2 | 7/2014 | Giordano et al. |
| 8,783,541 B2 | 7/2014 | Shelton, IV et al. |
| 8,784,415 B2 | 7/2014 | Malackowski et al. |
| 8,784,418 B2 | 7/2014 | Romero |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,710 B2 | 8/2014 | Ullrich et al. |
| 8,801,752 B2 | 8/2014 | Fortier et al. |
| 8,808,319 B2 | 8/2014 | Houser et al. |
| 8,814,856 B2 | 8/2014 | Elmouelhi et al. |
| 8,814,870 B2 | 8/2014 | Paraschiv et al. |
| 8,820,605 B2 | 9/2014 | Shelton, IV |
| 8,821,388 B2 | 9/2014 | Naito et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,518 B2 | 9/2014 | Faller et al. |
| 8,844,789 B2 | 9/2014 | Shelton, IV et al. |
| 8,845,537 B2 | 9/2014 | Tanaka et al. |
| 8,845,630 B2 | 9/2014 | Mehta et al. |
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,709 B2 | 10/2014 | Akagane et al. |

(56) References Cited

U.S. PATENT DOCUMENTS

| | | |
|---|---|---|
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,870,867 B2 | 10/2014 | Walberg et al. |
| 8,882,766 B2 | 11/2014 | Couture et al. |
| 8,882,791 B2 | 11/2014 | Stulen |
| 8,882,792 B2 | 11/2014 | Dietz et al. |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,414 B2 | 12/2014 | Stone et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,931,682 B2 | 1/2015 | Timm et al. |
| 8,936,614 B2 | 1/2015 | Allen, IV |
| 8,939,974 B2 | 1/2015 | Boudreaux et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,961,515 B2 | 2/2015 | Twomey et al. |
| 8,961,547 B2 | 2/2015 | Dietz et al. |
| 8,968,283 B2 | 3/2015 | Kharin |
| 8,968,294 B2 | 3/2015 | Maass et al. |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,302 B2 | 3/2015 | Aldridge et al. |
| 8,989,855 B2 | 3/2015 | Murphy et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,526 B2 | 3/2015 | Brodbeck et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,017,355 B2 | 4/2015 | Smith et al. |
| 9,017,372 B2 | 4/2015 | Artale et al. |
| 9,023,071 B2 | 5/2015 | Miller et al. |
| 9,023,072 B2 | 5/2015 | Young et al. |
| 9,028,397 B2 | 5/2015 | Naito |
| 9,028,476 B2 | 5/2015 | Bonn |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,973 B2 | 5/2015 | Krapohl et al. |
| 9,035,741 B2 | 5/2015 | Hamel et al. |
| 9,039,690 B2 | 5/2015 | Kersten et al. |
| 9,039,695 B2 | 5/2015 | Giordano et al. |
| 9,039,705 B2 | 5/2015 | Takashino |
| 9,043,018 B2 | 5/2015 | Mohr |
| 9,044,227 B2 | 6/2015 | Shelton, IV et al. |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 * | 6/2015 | Houser ............ A61B 17/29 |
| 9,050,093 B2 | 6/2015 | Aldridge et al. |
| 9,050,098 B2 | 6/2015 | Deville et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,063,049 B2 | 6/2015 | Beach et al. |
| 9,066,723 B2 | 6/2015 | Beller et al. |
| 9,066,747 B2 | 6/2015 | Robertson |
| 9,072,535 B2 | 7/2015 | Shelton, IV et al. |
| 9,072,536 B2 | 7/2015 | Shelton, IV et al. |
| 9,072,539 B2 | 7/2015 | Messerly et al. |
| 9,084,624 B2 | 7/2015 | Larkin et al. |
| 9,084,878 B2 | 7/2015 | Kawaguchi et al. |
| 9,089,327 B2 | 7/2015 | Worrell et al. |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,101,385 B2 | 8/2015 | Shelton, IV et al. |
| 9,107,684 B2 | 8/2015 | Ma |
| 9,107,689 B2 | 8/2015 | Robertson et al. |
| 9,107,690 B2 | 8/2015 | Bales, Jr. et al. |
| 9,113,900 B2 | 8/2015 | Buysse et al. |
| 9,113,940 B2 | 8/2015 | Twomey |
| 9,114,245 B2 | 8/2015 | Dietz et al. |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,125,722 B2 | 9/2015 | Schwartz |
| 9,147,965 B2 | 9/2015 | Lee |
| 9,149,324 B2 | 10/2015 | Huang et al. |
| 9,149,325 B2 | 10/2015 | Worrell et al. |
| 9,161,803 B2 | 10/2015 | Yates et al. |
| 9,168,054 B2 | 10/2015 | Turner et al. |
| 9,168,055 B2 | 10/2015 | Houser et al. |
| 9,168,085 B2 | 10/2015 | Juzkiw et al. |
| 9,168,089 B2 | 10/2015 | Buysse et al. |
| 9,168,090 B2 | 10/2015 | Strobl et al. |
| 9,173,656 B2 | 11/2015 | Schurr et al. |
| 9,179,912 B2 | 11/2015 | Yates et al. |
| 9,186,199 B2 | 11/2015 | Strauss et al. |
| 9,186,204 B2 | 11/2015 | Nishimura et al. |
| 9,192,380 B2 | 11/2015 | (Tarinelli) Racenet et al. |
| 9,192,431 B2 | 11/2015 | Woodruff et al. |
| 9,198,714 B2 | 12/2015 | Worrell et al. |
| 9,198,715 B2 | 12/2015 | Livneh |
| 9,204,879 B2 | 12/2015 | Shelton, IV |
| 9,204,891 B2 | 12/2015 | Weitzman |
| 9,204,918 B2 | 12/2015 | Germain et al. |
| 9,204,923 B2 | 12/2015 | Manzo et al. |
| 9,216,050 B2 | 12/2015 | Condie et al. |
| 9,216,062 B2 | 12/2015 | Duque et al. |
| 9,220,483 B2 | 12/2015 | Frankhouser et al. |
| 9,220,527 B2 | 12/2015 | Houser et al. |
| 9,220,559 B2 | 12/2015 | Worrell et al. |
| 9,226,750 B2 | 1/2016 | Weir et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,891 B2 | 1/2016 | Shelton, IV |
| 9,237,921 B2 | 1/2016 | Messerly et al. |
| 9,237,923 B2 | 1/2016 | Worrell et al. |
| 9,241,060 B1 | 1/2016 | Fujisaki |
| 9,241,692 B2 | 1/2016 | Gunday et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,241,768 B2 | 1/2016 | Sandhu et al. |
| 9,247,953 B2 | 2/2016 | Palmer et al. |
| 9,254,165 B2 | 2/2016 | Aronow et al. |
| 9,254,171 B2 | 2/2016 | Trees et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,926 B2 | 2/2016 | Strobl et al. |
| 9,265,973 B2 | 2/2016 | Akagane |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |

(56) References Cited

U.S. PATENT DOCUMENTS

| | | |
|---|---|---|
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,301,772 B2 | 4/2016 | Kimball et al. |
| 9,307,388 B2 | 4/2016 | Liang et al. |
| 9,307,986 B2 | 4/2016 | Hall et al. |
| 9,308,009 B2 | 4/2016 | Madan et al. |
| 9,308,014 B2 | 4/2016 | Fischer |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,787 B2 | 5/2016 | Sanai et al. |
| 9,326,788 B2 | 5/2016 | Batross et al. |
| 9,333,025 B2 | 5/2016 | Monson et al. |
| 9,339,289 B2 | 5/2016 | Robertson |
| 9,339,323 B2 | 5/2016 | Eder et al. |
| 9,339,326 B2 | 5/2016 | McCullagh et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,351,754 B2 | 5/2016 | Vakharia et al. |
| 9,352,173 B2 | 5/2016 | Yamada et al. |
| 9,358,065 B2 | 6/2016 | Ladtkow et al. |
| 9,358,407 B2 | 6/2016 | Akagane |
| 9,364,230 B2 | 6/2016 | Shelton, IV et al. |
| 9,370,400 B2 | 6/2016 | Parihar |
| 9,370,611 B2 | 6/2016 | Ross et al. |
| 9,375,230 B2 | 6/2016 | Ross et al. |
| 9,375,232 B2 | 6/2016 | Hunt et al. |
| 9,375,267 B2 | 6/2016 | Kerr et al. |
| 9,381,058 B2 | 7/2016 | Houser et al. |
| 9,386,983 B2 | 7/2016 | Swensgard et al. |
| 9,393,037 B2 | 7/2016 | Olson et al. |
| D763,442 S | 8/2016 | Price et al. |
| 9,402,680 B2 | 8/2016 | Ginnebaugh et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,060 B2 | 8/2016 | Monson et al. |
| 9,427,249 B2 | 8/2016 | Robertson et al. |
| 9,439,668 B2 | 9/2016 | Timm et al. |
| 9,439,669 B2 | 9/2016 | Wiener et al. |
| 9,439,671 B2 | 9/2016 | Akagane |
| 9,445,784 B2 | 9/2016 | O'Keeffe |
| 9,445,832 B2 | 9/2016 | Wiener et al. |
| 9,445,833 B2 | 9/2016 | Akagane |
| 9,451,967 B2 | 9/2016 | Jordan et al. |
| 9,456,863 B2 | 10/2016 | Moua |
| 9,456,864 B2 | 10/2016 | Witt et al. |
| 9,468,498 B2 | 10/2016 | Sigmon, Jr. |
| 9,474,542 B2 | 10/2016 | Slipszenko et al. |
| 9,486,235 B2 | 11/2016 | Harrington et al. |
| 9,486,236 B2 | 11/2016 | Price et al. |
| 9,492,187 B2 | 11/2016 | Ravikumar et al. |
| 9,492,224 B2 | 11/2016 | Boudreaux et al. |
| 9,498,245 B2 | 11/2016 | Voegele et al. |
| 9,504,483 B2 | 11/2016 | Houser et al. |
| 9,504,524 B2 | 11/2016 | Behnke, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,526,564 B2 | 12/2016 | Rusin |
| 9,526,565 B2 | 12/2016 | Strobl |
| 9,545,253 B2 | 1/2017 | Worrell et al. |
| 9,545,497 B2 | 1/2017 | Wenderow et al. |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,574,644 B2 | 2/2017 | Parihar |
| 9,592,072 B2 | 3/2017 | Akagane |
| 9,597,143 B2 | 3/2017 | Madan et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,622,729 B2 | 4/2017 | Dewaele et al. |
| 9,623,237 B2 | 4/2017 | Turner et al. |
| 9,636,135 B2 | 5/2017 | Stulen |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,111 B2 | 5/2017 | Shelton, IV et al. |
| 9,649,126 B2 | 5/2017 | Robertson et al. |
| 9,662,131 B2 | 5/2017 | Omori et al. |
| 9,668,806 B2 | 6/2017 | Unger et al. |
| 9,671,860 B2 | 6/2017 | Ogawa et al. |
| 9,675,374 B2 | 6/2017 | Stulen et al. |
| 9,675,375 B2 | 6/2017 | Houser et al. |
| 9,687,290 B2 | 6/2017 | Keller |
| 9,700,339 B2 | 7/2017 | Nield |
| 9,700,343 B2 | 7/2017 | Messerly et al. |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,724,118 B2 | 8/2017 | Schulte et al. |
| 9,724,152 B2 | 8/2017 | Horlle et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,737,735 B2 | 8/2017 | Dietz et al. |
| 9,743,947 B2 | 8/2017 | Price et al. |
| 9,757,142 B2 | 9/2017 | Shimizu |
| 9,757,186 B2 | 9/2017 | Boudreaux et al. |
| 9,764,164 B2 | 9/2017 | Wiener et al. |
| 9,782,214 B2 | 10/2017 | Houser et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,648 B2 | 10/2017 | Houser et al. |
| 9,801,675 B2 | 10/2017 | Sanai et al. |
| 9,808,308 B2 | 11/2017 | Faller et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,826,976 B2 | 11/2017 | Parihar et al. |
| 9,839,443 B2 | 12/2017 | Brockman et al. |
| 9,839,796 B2 | 12/2017 | Sawada |
| 9,848,901 B2 | 12/2017 | Robertson et al. |
| 9,848,902 B2 | 12/2017 | Price et al. |
| 9,848,937 B2 | 12/2017 | Trees et al. |
| 9,861,428 B2 | 1/2018 | Trees et al. |
| 9,872,725 B2 | 1/2018 | Worrell et al. |
| 9,877,720 B2 | 1/2018 | Worrell et al. |
| 9,877,776 B2 | 1/2018 | Boudreaux |
| 9,883,884 B2 | 2/2018 | Neurohr et al. |
| 9,888,958 B2 | 2/2018 | Evans et al. |
| 9,901,339 B2 | 2/2018 | Farascioni |
| 9,901,359 B2 | 2/2018 | Faller et al. |
| 9,907,563 B2 | 3/2018 | Germain et al. |
| 9,913,655 B2 | 3/2018 | Scheib et al. |
| 9,913,656 B2 | 3/2018 | Stulen |
| 9,913,680 B2 | 3/2018 | Voegele et al. |
| 9,918,736 B2 | 3/2018 | Van Tol et al. |
| 9,925,003 B2 | 3/2018 | Parihar et al. |
| 9,943,325 B2 | 4/2018 | Faller et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,987,033 B2 | 6/2018 | Neurohr et al. |
| 10,010,339 B2 | 7/2018 | Witt et al. |
| 10,010,341 B2 | 7/2018 | Houser et al. |
| 10,016,207 B2 | 7/2018 | Suzuki et al. |
| 10,022,142 B2 | 7/2018 | Aranyi et al. |
| 10,022,567 B2 | 7/2018 | Messerly et al. |
| 10,022,568 B2 | 7/2018 | Messerly et al. |
| 10,028,765 B2 | 7/2018 | Hibner et al. |
| 10,028,786 B2 | 7/2018 | Mucilli et al. |

(56) References Cited

U.S. PATENT DOCUMENTS

| | | |
|---|---|---|
| 10,034,684 B2 | 7/2018 | Weisenburgh, II et al. |
| 10,034,685 B2 | 7/2018 | Boudreaux et al. |
| 10,034,704 B2 | 7/2018 | Asher et al. |
| 10,039,588 B2 | 8/2018 | Harper et al. |
| 10,045,794 B2 | 8/2018 | Witt et al. |
| 10,045,819 B2 | 8/2018 | Jensen et al. |
| 10,070,916 B2 | 9/2018 | Artale |
| 10,085,762 B2 | 10/2018 | Timm et al. |
| 10,092,310 B2 | 10/2018 | Boudreaux et al. |
| 10,092,344 B2 | 10/2018 | Mohr et al. |
| 10,092,348 B2 | 10/2018 | Boudreaux |
| 10,092,350 B2 | 10/2018 | Rothweiler et al. |
| 10,111,699 B2 | 10/2018 | Boudreaux |
| 10,117,667 B2 | 11/2018 | Robertson et al. |
| 10,117,702 B2 | 11/2018 | Danziger et al. |
| 10,130,410 B2 | 11/2018 | Strobl et al. |
| 10,154,852 B2 | 12/2018 | Conlon et al. |
| 10,159,524 B2 | 12/2018 | Yates et al. |
| 10,166,060 B2 | 1/2019 | Johnson et al. |
| 10,172,669 B2 | 1/2019 | Felder et al. |
| 10,179,022 B2 | 1/2019 | Yates et al. |
| 10,182,837 B2 | 1/2019 | Isola et al. |
| 10,188,385 B2 | 1/2019 | Kerr et al. |
| 10,194,972 B2 | 2/2019 | Yates et al. |
| 10,194,973 B2 | 2/2019 | Wiener et al. |
| 10,194,976 B2 | 2/2019 | Boudreaux |
| 10,194,977 B2 | 2/2019 | Yang |
| 10,201,365 B2 | 2/2019 | Boudreaux et al. |
| 10,201,382 B2 | 2/2019 | Wiener et al. |
| 10,226,273 B2 | 3/2019 | Messerly et al. |
| 10,231,747 B2 | 3/2019 | Stulen et al. |
| 10,245,065 B2 | 4/2019 | Witt et al. |
| 10,245,095 B2 | 4/2019 | Boudreaux |
| 10,251,664 B2 | 4/2019 | Shelton, IV et al. |
| 10,263,171 B2 | 4/2019 | Wiener et al. |
| 10,265,094 B2 | 4/2019 | Witt et al. |
| 10,265,117 B2 | 4/2019 | Wiener et al. |
| 10,265,118 B2 | 4/2019 | Gerhardt |
| D847,990 S | 5/2019 | Kimball |
| 10,278,721 B2 | 5/2019 | Dietz et al. |
| 10,285,723 B2 | 5/2019 | Conlon et al. |
| 10,285,724 B2 | 5/2019 | Faller et al. |
| 10,299,810 B2 | 5/2019 | Robertson et al. |
| 10,299,821 B2 | 5/2019 | Shelton, IV et al. |
| 10,314,638 B2 | 6/2019 | Gee et al. |
| 10,321,950 B2 | 6/2019 | Yates et al. |
| 10,335,182 B2 | 7/2019 | Stulen et al. |
| 10,335,614 B2 | 7/2019 | Messerly et al. |
| 10,342,602 B2 | 7/2019 | Strobl et al. |
| 10,357,303 B2 | 7/2019 | Conlon et al. |
| 10,363,058 B2 | 7/2019 | Roberson et al. |
| 10,368,892 B2 | 8/2019 | Stulen et al. |
| 10,368,894 B2 | 8/2019 | Madan et al. |
| 10,368,957 B2 | 8/2019 | Denzinger et al. |
| 10,398,466 B2 | 9/2019 | Stulen et al. |
| 10,398,497 B2 | 9/2019 | Batross et al. |
| 10,413,352 B2 | 9/2019 | Thomas et al. |
| 10,420,579 B2 | 9/2019 | Wiener et al. |
| 10,420,580 B2 | 9/2019 | Messerly et al. |
| 10,420,607 B2 | 9/2019 | Woloszko et al. |
| 10,426,507 B2 | 10/2019 | Wiener et al. |
| 10,426,978 B2 | 10/2019 | Akagane |
| 10,433,865 B2 | 10/2019 | Witt et al. |
| 10,433,866 B2 | 10/2019 | Witt et al. |
| 10,433,900 B2 | 10/2019 | Harris et al. |
| 10,441,308 B2 | 10/2019 | Robertson |
| 10,441,310 B2 | 10/2019 | Olson et al. |
| 10,441,345 B2 | 10/2019 | Aldridge et al. |
| 10,463,421 B2 | 11/2019 | Boudreaux et al. |
| 10,463,887 B2 | 11/2019 | Witt et al. |
| 10,470,788 B2 | 11/2019 | Sinelnikov |
| 10,512,795 B2 | 12/2019 | Voegele et al. |
| 10,517,627 B2 | 12/2019 | Timm et al. |
| 10,524,854 B2 | 1/2020 | Woodruff et al. |
| 10,531,910 B2 | 1/2020 | Houser et al. |
| 10,537,351 B2 | 1/2020 | Shelton, IV et al. |
| 10,537,352 B2 | 1/2020 | Faller et al. |
| 10,537,667 B2 | 1/2020 | Anim |
| 10,543,008 B2 | 1/2020 | Vakharia et al. |
| 10,555,750 B2 | 2/2020 | Conlon et al. |
| 10,555,769 B2 | 2/2020 | Worrell et al. |
| 10,561,436 B2 | 2/2020 | Asher et al. |
| 10,575,892 B2 | 3/2020 | Danziger et al. |
| 10,595,929 B2 | 3/2020 | Boudreaux et al. |
| 10,595,930 B2 | 3/2020 | Scheib et al. |
| 10,603,064 B2 | 3/2020 | Zhang |
| 10,610,286 B2 | 4/2020 | Wiener et al. |
| 10,624,665 B2 | 4/2020 | Noui et al. |
| 10,624,691 B2 | 4/2020 | Wiener et al. |
| 10,639,092 B2 | 5/2020 | Corbett et al. |
| 10,677,764 B2 | 6/2020 | Ross et al. |
| 10,687,884 B2 | 6/2020 | Wiener et al. |
| 10,709,469 B2 | 7/2020 | Shelton, IV et al. |
| 10,709,906 B2 | 7/2020 | Nield |
| 10,716,615 B2 | 7/2020 | Shelton, IV et al. |
| 10,722,261 B2 | 7/2020 | Houser et al. |
| 10,729,458 B2 | 8/2020 | Stoddard et al. |
| 10,736,649 B2 | 8/2020 | Messerly et al. |
| 10,736,685 B2 | 8/2020 | Wiener et al. |
| 10,751,108 B2 | 8/2020 | Yates et al. |
| 10,758,294 B2 | 9/2020 | Jones |
| 10,779,845 B2 | 9/2020 | Timm et al. |
| 10,779,847 B2 | 9/2020 | Messerly et al. |
| 10,779,848 B2 | 9/2020 | Houser |
| 10,779,849 B2 | 9/2020 | Shelton, IV et al. |
| 10,779,879 B2 | 9/2020 | Yates et al. |
| 10,820,920 B2 | 11/2020 | Scoggins et al. |
| 10,820,938 B2 | 11/2020 | Fischer et al. |
| 10,828,056 B2 | 11/2020 | Messerly et al. |
| 10,828,057 B2 | 11/2020 | Neurohr et al. |
| 10,828,058 B2 | 11/2020 | Shelton, IV et al. |
| 10,828,059 B2 | 11/2020 | Price et al. |
| 10,835,307 B2 | 11/2020 | Shelton, IV et al. |
| 10,835,768 B2 | 11/2020 | Robertson et al. |
| 2001/0011176 A1 | 8/2001 | Boukhny |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0002378 A1 | 1/2002 | Messerly |
| 2002/0016603 A1 | 2/2002 | Wells |
| 2002/0019649 A1 | 2/2002 | Sikora et al. |
| 2002/0022836 A1 | 2/2002 | Goble et al. |
| 2002/0029055 A1 | 3/2002 | Bonutti |
| 2002/0049551 A1 | 4/2002 | Friedman et al. |
| 2002/0052595 A1 | 5/2002 | Witt et al. |
| 2002/0052617 A1 | 5/2002 | Anis et al. |
| 2002/0077550 A1 | 6/2002 | Rabiner et al. |
| 2002/0107517 A1 | 8/2002 | Witt et al. |
| 2002/0107538 A1* | 8/2002 | Shibata .......... A61B 17/320068 606/169 |
| 2002/0156466 A1 | 10/2002 | Sakurai et al. |
| 2002/0156493 A1 | 10/2002 | Houser et al. |
| 2002/0165577 A1 | 11/2002 | Witt et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0040758 A1 | 2/2003 | Wang et al. |
| 2003/0050572 A1 | 3/2003 | Brautigam et al. |
| 2003/0055443 A1 | 3/2003 | Spotnitz |
| 2003/0093113 A1 | 5/2003 | Fogarty et al. |
| 2003/0109875 A1 | 6/2003 | Tetzlaff et al. |
| 2003/0114851 A1 | 6/2003 | Truckai et al. |
| 2003/0114874 A1 | 6/2003 | Craig et al. |
| 2003/0120306 A1 | 6/2003 | Burbank et al. |
| 2003/0130693 A1 | 7/2003 | Levin et al. |
| 2003/0139741 A1 | 7/2003 | Goble et al. |
| 2003/0144680 A1 | 7/2003 | Kellogg et al. |
| 2003/0158548 A1 | 8/2003 | Phan et al. |
| 2003/0160698 A1 | 8/2003 | Andreasson et al. |
| 2003/0171747 A1 | 9/2003 | Kanehira et al. |
| 2003/0199794 A1 | 10/2003 | Sakurai et al. |

(56) References Cited

U.S. PATENT DOCUMENTS

| | | |
|---|---|---|
| 2003/0204199 A1 | 10/2003 | Novak et al. |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0039242 A1 | 2/2004 | Tolkoff et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0092921 A1 | 5/2004 | Kadziauskas et al. |
| 2004/0092992 A1 | 5/2004 | Adams et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0121159 A1 | 6/2004 | Cloud et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0147934 A1 | 7/2004 | Kiester |
| 2004/0147945 A1 | 7/2004 | Fritzsch |
| 2004/0147946 A1 | 7/2004 | Mastri et al. |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0193150 A1 | 9/2004 | Sharkey et al. |
| 2004/0199193 A1 | 10/2004 | Hayashi et al. |
| 2004/0199194 A1 | 10/2004 | Witt et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267298 A1 | 12/2004 | Cimino |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033337 A1 | 2/2005 | Muir et al. |
| 2005/0070800 A1 | 3/2005 | Takahashi |
| 2005/0085728 A1 | 4/2005 | Fukuda |
| 2005/0085803 A1* | 4/2005 | Okabe .............. A61B 17/320068 606/28 |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0131390 A1 | 6/2005 | Heinrich et al. |
| 2005/0143759 A1 | 6/2005 | Kelly |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0192611 A1 | 9/2005 | Houser |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261588 A1 | 11/2005 | Makin et al. |
| 2005/0267464 A1 | 12/2005 | Truckai et al. |
| 2005/0273090 A1 | 12/2005 | Nieman et al. |
| 2005/0288659 A1 | 12/2005 | Kimura et al. |
| 2006/0030797 A1 | 2/2006 | Zhou et al. |
| 2006/0030848 A1 | 2/2006 | Craig et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0095046 A1 | 5/2006 | Trieu et al. |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0224160 A1 | 10/2006 | Trieu et al. |
| 2006/0247558 A1 | 11/2006 | Yamada |
| 2006/0253050 A1 | 11/2006 | Yoshimine et al. |
| 2006/0257819 A1 | 11/2006 | Johnson |
| 2006/0264809 A1 | 11/2006 | Hansmann et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0032704 A1 | 2/2007 | Gandini et al. |
| 2007/0055228 A1 | 3/2007 | Berg et al. |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0130771 A1 | 6/2007 | Ehlert et al. |
| 2007/0149881 A1 | 6/2007 | Rabin |
| 2007/0156163 A1 | 7/2007 | Davison et al. |
| 2007/0166663 A1 | 7/2007 | Telles et al. |
| 2007/0170820 A1* | 7/2007 | Bromfield ............. H01L 41/313 310/364 |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0203483 A1 | 8/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239101 A1 | 10/2007 | Kellogg |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0275348 A1 | 11/2007 | Lemon |
| 2007/0282333 A1 | 12/2007 | Fortson et al. |
| 2007/0287933 A1 | 12/2007 | Phan et al. |
| 2007/0288055 A1 | 12/2007 | Lee |
| 2008/0013809 A1 | 1/2008 | Zhu et al. |
| 2008/0015575 A1 | 1/2008 | Odom et al. |
| 2008/0033465 A1 | 2/2008 | Schmitz et al. |
| 2008/0039746 A1 | 2/2008 | Hissong et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097281 A1 | 4/2008 | Zusman et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0125768 A1 | 5/2008 | Tahara et al. |
| 2008/0147058 A1 | 6/2008 | Horrell et al. |

(56) References Cited

U.S. PATENT DOCUMENTS

| | | |
|---|---|---|
| 2008/0147062 A1 | 6/2008 | Truckai et al. |
| 2008/0147092 A1 | 6/2008 | Rogge et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243162 A1 | 10/2008 | Shibata et al. |
| 2008/0281200 A1 | 11/2008 | Voic et al. |
| 2008/0281315 A1 | 11/2008 | Gines |
| 2008/0287948 A1 | 11/2008 | Newton et al. |
| 2008/0296346 A1 | 12/2008 | Shelton, IV et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0036912 A1* | 2/2009 | Wiener ............ A61B 17/2202 606/169 |
| 2009/0043228 A1 | 2/2009 | Northrop et al. |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0069830 A1 | 3/2009 | Mulvihill et al. |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088785 A1 | 4/2009 | Masuda |
| 2009/0118751 A1 | 5/2009 | Wiener et al. |
| 2009/0143678 A1 | 6/2009 | Keast et al. |
| 2009/0143799 A1 | 6/2009 | Smith et al. |
| 2009/0143800 A1 | 6/2009 | Deville et al. |
| 2009/0163807 A1 | 6/2009 | Sliwa |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0216157 A1 | 8/2009 | Yamada |
| 2009/0223033 A1 | 9/2009 | Houser |
| 2009/0248021 A1 | 10/2009 | McKenna |
| 2009/0254077 A1 | 10/2009 | Craig |
| 2009/0254080 A1 | 10/2009 | Honda |
| 2009/0259149 A1 | 10/2009 | Tahara et al. |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0299141 A1 | 12/2009 | Downey et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0034605 A1 | 2/2010 | Huckins et al. |
| 2010/0036370 A1 | 2/2010 | Mirel et al. |
| 2010/0042126 A1 | 2/2010 | Houser et al. |
| 2010/0049180 A1 | 2/2010 | Wells et al. |
| 2010/0057118 A1 | 3/2010 | Dietz et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0109480 A1 | 5/2010 | Forslund et al. |
| 2010/0158307 A1 | 6/2010 | Kubota et al. |
| 2010/0168741 A1 | 7/2010 | Sanai et al. |
| 2010/0181966 A1 | 7/2010 | Sakakibara |
| 2010/0187283 A1 | 7/2010 | Crainich et al. |
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0228191 A1 | 9/2010 | Alvarez et al. |
| 2010/0234906 A1 | 9/2010 | Koh |
| 2010/0274160 A1 | 10/2010 | Yachi et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2010/0312186 A1 | 12/2010 | Suchdev et al. |
| 2010/0331742 A1 | 12/2010 | Masuda |
| 2010/0331873 A1 | 12/2010 | Dannaher et al. |
| 2011/0004233 A1 | 1/2011 | Muir et al. |
| 2011/0028964 A1 | 2/2011 | Edwards |
| 2011/0106141 A1 | 5/2011 | Nakamura |
| 2011/0125151 A1 | 5/2011 | Strauss et al. |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0291526 A1 | 12/2011 | Abramovich et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022583 A1 | 1/2012 | Sugalski et al. |
| 2012/0041358 A1 | 2/2012 | Mann et al. |
| 2012/0059289 A1 | 3/2012 | Nield et al. |
| 2012/0071863 A1 | 3/2012 | Lee et al. |
| 2012/0078244 A1 | 3/2012 | Worrell et al. |
| 2012/0078249 A1 | 3/2012 | Eichmann et al. |
| 2012/0101495 A1 | 4/2012 | Young et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0136279 A1 | 5/2012 | Tanaka et al. |
| 2012/0143211 A1 | 6/2012 | Kishi |
| 2012/0172904 A1 | 7/2012 | Muir et al. |
| 2012/0265241 A1 | 10/2012 | Hart et al. |
| 2012/0296371 A1 | 11/2012 | Kappus et al. |
| 2013/0023925 A1 | 1/2013 | Mueller |
| 2013/0090576 A1 | 4/2013 | Stulen et al. |
| 2013/0116717 A1 | 5/2013 | Balek et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0231691 A1 | 9/2013 | Houser |
| 2013/0253256 A1 | 9/2013 | Griffith et al. |
| 2013/0277410 A1 | 10/2013 | Fernandez et al. |
| 2013/0296843 A1 | 11/2013 | Boudreaux et al. |
| 2013/0331873 A1 | 12/2013 | Ross et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0081299 A1 | 3/2014 | Dietz et al. |
| 2014/0121569 A1 | 5/2014 | Schafer et al. |
| 2014/0135663 A1 | 5/2014 | Funakubo et al. |
| 2014/0135804 A1 | 5/2014 | Weisenburgh, II et al. |
| 2014/0194874 A1 | 7/2014 | Dietz et al. |
| 2014/0194875 A1 | 7/2014 | Reschke et al. |
| 2014/0207135 A1 | 7/2014 | Winter |
| 2014/0207163 A1 | 7/2014 | Eichmann et al. |
| 2014/0323926 A1 | 10/2014 | Akagane |
| 2014/0371735 A1 | 12/2014 | Long |
| 2015/0011889 A1 | 1/2015 | Lee |
| 2015/0080876 A1 | 3/2015 | Worrell et al. |
| 2015/0112335 A1 | 4/2015 | Boudreaux et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |

(56) References Cited

U.S. PATENT DOCUMENTS

| | | | |
|---|---|---|---|
| 2015/0164537 A1 | 6/2015 | Cagle et al. |
| 2015/0164538 A1 | 6/2015 | Aldridge et al. |
| 2015/0257780 A1 | 9/2015 | Houser |
| 2015/0272659 A1 | 10/2015 | Boudreaux et al. |
| 2015/0289854 A1 | 10/2015 | Cho et al. |
| 2016/0045248 A1 | 2/2016 | Unger et al. |
| 2016/0051316 A1 | 2/2016 | Boudreaux |
| 2016/0114355 A1 | 4/2016 | Sakai et al. |
| 2016/0121143 A1 | 5/2016 | Mumaw et al. |
| 2016/0128769 A1 | 5/2016 | Rontal et al. |
| 2016/0175029 A1 | 6/2016 | Witt et al. |
| 2016/0206342 A1 | 7/2016 | Robertson et al. |
| 2016/0240768 A1 | 8/2016 | Fujii et al. |
| 2016/0262786 A1 | 9/2016 | Madan et al. |
| 2016/0270842 A1 | 9/2016 | Strobl et al. |
| 2016/0270843 A1 | 9/2016 | Boudreaux et al. |
| 2016/0296251 A1 | 10/2016 | Olson et al. |
| 2016/0296252 A1 | 10/2016 | Olson et al. |
| 2016/0296270 A1 | 10/2016 | Strobl et al. |
| 2016/0367281 A1 | 12/2016 | Gee et al. |
| 2017/0000541 A1 | 1/2017 | Yates et al. |
| 2017/0027624 A1 | 2/2017 | Wilson et al. |
| 2017/0036044 A1 | 2/2017 | Ito |
| 2017/0086876 A1 | 3/2017 | Wiener et al. |
| 2017/0086908 A1 | 3/2017 | Wiener et al. |
| 2017/0086909 A1 | 3/2017 | Yates et al. |
| 2017/0105757 A1 | 4/2017 | Weir et al. |
| 2017/0119426 A1 | 5/2017 | Akagane |
| 2017/0135751 A1 | 5/2017 | Rothweiler et al. |
| 2017/0164972 A1 | 6/2017 | Johnson et al. |
| 2017/0189095 A1 | 7/2017 | Danziger et al. |
| 2017/0196586 A1 | 7/2017 | Witt et al. |
| 2017/0202571 A1 | 7/2017 | Shelton, IV et al. |
| 2017/0202572 A1 | 7/2017 | Shelton, IV et al. |
| 2017/0202591 A1 | 7/2017 | Shelton, IV et al. |
| 2017/0202595 A1 | 7/2017 | Shelton, IV |
| 2017/0202597 A1 | 7/2017 | Shelton, IV et al. |
| 2017/0202598 A1 | 7/2017 | Shelton, IV et al. |
| 2017/0202599 A1 | 7/2017 | Shelton, IV et al. |
| 2017/0202605 A1 | 7/2017 | Shelton, IV et al. |
| 2017/0202607 A1 | 7/2017 | Shelton, IV et al. |
| 2017/0360468 A1 | 12/2017 | Eichmann et al. |
| 2018/0014845 A1 | 1/2018 | Dannaher |
| 2018/0014846 A1* | 1/2018 | Rhee ............... B06B 3/00 |
| 2018/0014848 A1 | 1/2018 | Messerly et al. |
| 2018/0049767 A1 | 2/2018 | Gee et al. |
| 2018/0055529 A1 | 3/2018 | Messerly et al. |
| 2018/0078268 A1 | 3/2018 | Messerly et al. |
| 2018/0125523 A1 | 5/2018 | Johnson |
| 2018/0177521 A1 | 6/2018 | Faller et al. |
| 2018/0177545 A1 | 6/2018 | Boudreaux et al. |
| 2018/0296239 A1 | 10/2018 | Houser et al. |
| 2018/0310983 A1 | 11/2018 | Worrell et al. |
| 2019/0053822 A1 | 2/2019 | Robertson et al. |
| 2019/0239919 A1 | 8/2019 | Witt et al. |
| 2019/0262029 A1 | 8/2019 | Messerly et al. |
| 2019/0350615 A1 | 11/2019 | Messerly et al. |
| 2019/0380733 A1 | 12/2019 | Stulen et al. |
| 2019/0381339 A1 | 12/2019 | Voegele et al. |
| 2019/0381340 A1 | 12/2019 | Voegele et al. |
| 2020/0008857 A1 | 1/2020 | Conlon et al. |
| 2020/0015798 A1 | 1/2020 | Wiener et al. |
| 2020/0015838 A1 | 1/2020 | Robertson |
| 2020/0046401 A1 | 2/2020 | Witt et al. |
| 2020/0054386 A1 | 2/2020 | Houser et al. |
| 2020/0054899 A1 | 2/2020 | Wiener et al. |
| 2020/0085462 A1 | 3/2020 | Robertson |
| 2020/0085466 A1 | 3/2020 | Faller et al. |

FOREIGN PATENT DOCUMENTS

| | | |
|---|---|---|
| CN | 2460047 Y | 11/2001 |
| CN | 1634601 A | 7/2005 |
| CN | 1775323 A | 5/2006 |
| CN | 1922563 A | 2/2007 |
| CN | 2868227 Y | 2/2007 |
| CN | 202027624 U | 11/2011 |
| CN | 102335778 A | 2/2012 |
| CN | 103668171 A | 3/2014 |
| CN | 103921215 A | 7/2014 |
| CN | 106077718 A | 11/2016 |
| DE | 2065681 A1 | 3/1975 |
| DE | 3904558 A1 | 8/1990 |
| DE | 9210327 U1 | 11/1992 |
| DE | 4300307 A1 | 7/1994 |
| DE | 4434938 C1 | 2/1996 |
| DE | 29623113 U1 | 10/1997 |
| DE | 20004812 U1 | 9/2000 |
| DE | 20021619 U1 | 3/2001 |
| DE | 10042606 A1 | 8/2001 |
| DE | 10201569 A1 | 7/2003 |
| EP | 0171967 A2 | 2/1986 |
| EP | 0336742 A2 | 10/1989 |
| EP | 0136855 B1 | 11/1989 |
| EP | 0705571 A1 | 4/1996 |
| EP | 1543854 A1 | 6/2005 |
| EP | 1698289 A2 | 9/2006 |
| EP | 1862133 A1 | 12/2007 |
| EP | 1972264 A1 | 9/2008 |
| EP | 2060238 A1 | 5/2009 |
| EP | 1747761 B1 | 10/2009 |
| EP | 2131760 A1 | 12/2009 |
| EP | 1214913 B1 | 7/2010 |
| EP | 1946708 B1 | 6/2011 |
| EP | 1767164 B1 | 1/2013 |
| EP | 2578172 A2 | 4/2013 |
| EP | 2510891 B1 | 6/2016 |
| FR | 2454351 A1 | 11/1980 |
| FR | 2964554 A1 | 3/2012 |
| GB | 2032221 A | 4/1980 |
| GB | 2317566 A | 4/1998 |
| GB | 2318298 A | 4/1998 |
| GB | 2425480 A | 11/2006 |
| JP | S50100891 A | 8/1975 |
| JP | S5968513 U | 5/1984 |
| JP | S59141938 A | 8/1984 |
| JP | S62221343 A | 9/1987 |
| JP | S62227343 A | 10/1987 |
| JP | S62292153 A | 12/1987 |
| JP | S62292154 A | 12/1987 |
| JP | S63109386 A | 5/1988 |
| JP | S63315049 A | 12/1988 |
| JP | H01151452 A | 6/1989 |
| JP | H01198540 A | 8/1989 |
| JP | H0271510 U | 5/1990 |
| JP | H02286149 A | 11/1990 |
| JP | H02292193 A | 12/1990 |
| JP | H0337061 A | 2/1991 |
| JP | H0425707 U | 2/1992 |
| JP | H0464351 A | 2/1992 |
| JP | H0430508 U | 3/1992 |
| JP | H04152942 A | 5/1992 |
| JP | H04161078 A | 6/1992 |
| JP | H0595955 A | 4/1993 |
| JP | H05115490 A | 5/1993 |
| JP | H0647048 A | 2/1994 |
| JP | H0670938 A | 3/1994 |
| JP | H06104503 A | 4/1994 |
| JP | H07185457 A | 7/1995 |
| JP | H0824266 A | 1/1996 |
| JP | H08229050 A | 9/1996 |
| JP | H08275950 A | 10/1996 |
| JP | H08275951 A | 10/1996 |
| JP | H08299351 A | 11/1996 |
| JP | H08336545 A | 12/1996 |
| JP | H09135553 A | 5/1997 |
| JP | H09140722 A | 6/1997 |
| JP | H105236 A | 1/1998 |
| JP | H105237 A | 1/1998 |
| JP | H10295700 A | 11/1998 |
| JP | H11128238 A | 5/1999 |
| JP | 2000139943 A | 5/2000 |
| JP | 2000210296 A | 8/2000 |
| JP | 2000210299 A | 8/2000 |

(56) References Cited

FOREIGN PATENT DOCUMENTS

| | | |
|---|---|---|
| JP | 2000271145 A | 10/2000 |
| JP | 2000287987 A | 10/2000 |
| JP | 2000312682 A | 11/2000 |
| JP | 2001029353 A | 2/2001 |
| JP | 2001057985 A | 3/2001 |
| JP | 2001170066 A | 6/2001 |
| JP | 2001198137 A | 7/2001 |
| JP | 2002186901 A | 7/2002 |
| JP | 2002233533 A | 8/2002 |
| JP | 2002263579 A | 9/2002 |
| JP | 2002330977 A | 11/2002 |
| JP | 2003000612 A | 1/2003 |
| JP | 2003010201 A | 1/2003 |
| JP | 2003116870 A | 4/2003 |
| JP | 2003126104 A | 5/2003 |
| JP | 2003126110 A | 5/2003 |
| JP | 2003153919 A | 5/2003 |
| JP | 2003230567 A | 8/2003 |
| JP | 2003339730 A | 12/2003 |
| JP | 2004129871 A | 4/2004 |
| JP | 2004147701 A | 5/2004 |
| JP | 2004209043 A | 7/2004 |
| JP | 2005027026 A | 1/2005 |
| JP | 2005074088 A | 3/2005 |
| JP | 2005094552 A | 4/2005 |
| JP | 2005253674 A | 9/2005 |
| JP | 2006217716 A | 8/2006 |
| JP | 2006288431 A | 10/2006 |
| JP | 3841627 B2 | 11/2006 |
| JP | D1339835 S | 8/2008 |
| JP | 2009297352 A | 12/2009 |
| JP | 2010009686 A | 1/2010 |
| JP | 2010121865 A | 6/2010 |
| JP | 2011160586 A | 8/2011 |
| JP | 2012235658 A | 11/2012 |
| KR | 100789356 B1 | 12/2007 |
| RU | 2154437 C1 | 8/2000 |
| RU | 22035 U1 | 3/2002 |
| RU | 2201169 C2 | 3/2003 |
| RU | 2405603 C1 | 12/2010 |
| SU | 850068 A1 | 7/1981 |
| WO | WO-8103272 A1 | 11/1981 |
| WO | WO-9308757 A1 | 5/1993 |
| WO | WO-9314708 A1 | 8/1993 |
| WO | WO-9421183 A1 | 9/1994 |
| WO | WO-9424949 A1 | 11/1994 |
| WO | WO-9639086 A1 | 12/1996 |
| WO | WO-9800069 A1 | 1/1998 |
| WO | WO-9805437 A1 | 2/1998 |
| WO | WO-9816157 A1 | 4/1998 |
| WO | WO-9920213 A1 | 4/1999 |
| WO | WO-9923960 A1 | 5/1999 |
| WO | WO-0024322 A1 | 5/2000 |
| WO | WO-0024330 A1 | 5/2000 |
| WO | WO-0064358 A2 | 11/2000 |
| WO | WO-0128444 A1 | 4/2001 |
| WO | WO-0132087 A1 | 5/2001 |
| WO | WO-0167970 A1 | 9/2001 |
| WO | WO-0195810 A2 | 12/2001 |
| WO | WO-02076685 A1 | 10/2002 |
| WO | WO-02080799 A1 | 10/2002 |
| WO | WO-2004037095 A2 | 5/2004 |
| WO | WO-2004078051 A2 | 9/2004 |
| WO | WO-2004098426 A2 | 11/2004 |
| WO | WO-2005084250 A2 | 9/2005 |
| WO | WO-2007008710 A2 | 1/2007 |
| WO | WO-2008118709 A1 | 10/2008 |
| WO | WO-2008130793 A1 | 10/2008 |
| WO | WO-2010104755 A1 | 9/2010 |
| WO | WO-2011008672 A2 | 1/2011 |
| WO | WO-2011052939 A2 | 5/2011 |
| WO | WO-2011060031 A1 | 5/2011 |
| WO | WO-2012044606 A2 | 4/2012 |
| WO | WO-2012066983 A1 | 5/2012 |
| WO | WO-2013048963 A2 | 4/2013 |

OTHER PUBLICATIONS

AST Products, Inc., "Principles of Video Contact Angle Analysis," 20 pages, (2006).
Campbell et al, "Thermal Imaging in Surgery," p. 19-3, in Medical Infrared Imaging, N. A. Diakides and J. D. Bronzino, Eds. (2008).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Heat-induced changes in the mechanics of a collagenous tissue: pseudoelastic behavior at 37° C," Journal of Biomechanics, 31, pp. 211-216 (1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Covidien 501(k) Summary Sonicision, dated Feb. 24, 2011 (7 pages).
Covidien Brochure, [Value Analysis Brief], LigaSure Advance™ Pistol Grip, dated Rev. Apr. 2010 (7 pages).
Covidien Brochure, LigaSure Atlas™ Hand Switching Instruments, dated Dec. 2008 (2 pages).
Covidien Brochure, LigaSure Impact™ Instrument LF4318, dated Feb. 2013 (3 pages).
Covidien Brochure, The LigaSure Precise™Instrument, dated Mar. 2011 (2 pages).
Covidien Brochure, the LigaSure™ 5 mm Blunt Tip Sealer/Divider Family, dated Apr. 2013 (2 pages).
Douglas, S.C. "Introduction to Adaptive Filter". Digital Signal Processing Handbook. Ed. Vijay K. Madisetti and Douglas B. Williams. Boca Raton: CRC Press LLC, 1999.
Emam, Tarek A. et al., "How Safe is High-Power Ultrasonic Dissection?," Annals of Surgery, (2003), pp. 186-191, vol. 237, No. 2, Lippincott Williams & Wilkins, Inc., Philadelphia, PA.
Erbe Electrosurgery VIO® 200 S, (2012), p. 7, 12 pages, dated Mar. 31, 2014 at http://www.erbe-med. com/erbe/media/Marketing materialien/85140170 ERBE EN VIO 200 S D027541.
F. A. Duck, "Optical Properties of Tissue Including Ultraviolet and Infrared Radiation," pp. 43-71 in Physical Properties of Tissue (1990).
Feil, Wolfgang, M.D., et al., "Ultrasonic Energy for Cutting, Coagulating, and Dissecting," (2005), pp. IV, 17, 21, and 23; ISBN 3-13-127521-9 (New York, NY, Thieme, New York).
Fowler, K.R., "A Programmable, Arbitrary Waveform Electrosurgical Device," IEEE Engineering in Medicine and Biology Society 10th Annual International Conference, pp. 1324, 1325 (1988).
Gerhard, Glen C., "Surgical Electrotechnology: Quo Vadis?," IEEE Transactions on Biomedical Engineering, vol. BME-31, No. 12, pp. 787-792, Dec. 1984.
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Glaser and Subak-Sharpe,lntegrated Circuit Engineering, Addison-Wesley Publishing, Reading, MA (1979). (book—not attached).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Graff, K.F., "Elastic Wave Propagation in a Curved Sonic Transmission Line," IEEE Transactions on Sonics and Ultrasonics, SU-17(1), 1-6 (1970).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Hayashi et al., "The Effect of Thermal Heating on the Length and Histologic Properties of the Glenohumeral Joint Capsule," Ameri-

(56) References Cited

OTHER PUBLICATIONS can Journal of Sports Medicine, vol. 25, Issue 1, 11 pages (Jan. 1997), URL: http://www.mdconsult.com/das/article/body/156183648-2/jorg=journal&source=MI&sp=1 . . ., dated Aug. 25, 2009.
Henriques. F.C., "Studies in thermal injury V. The predictability and the significance of thermally induced rate processes leading to irreversible epidermal injury." Archives of Pathology, 434, pp. 489-502 (1947).
http://www.4-traders.com/Johnson-Johnson-4832/news/Johnson-Johnson-Ethicon-E. . .
http://www.apicalinstr.com/generators.htm.
http://www.dotmed.com/listing/electrosurical-unit/ethicon/ultracision-g110-/1466724.
http://www.medicalexpo.com/medical-manufacturer/electrosurgical-generator-6951.html.
http://www.megadyne.com/es_generator.php.
http://www.valleylab.com/product/es/generators/index.html.
http://www.ethicon.com/gb-en/healthcare-professionals/products/energy-devices/capital//ge. . . .
https://www.kjmagnetics.com/fieldcalculator.asp, dated Jul. 11, 2016, backdated to Nov. 11, 2011 via https://web.archive.org/web/20111116164447/http://www.kjmagnetics.com/fieldcalculator.asp.
Humphrey, J.D., "Continuum Thermomechanics and the Clinical Treatment of Disease and Injury," Appl. Mech. Rev., vol. 56, No. 2 pp. 231-260 (Mar. 2003).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Incropera et al., Fundamentals of Heat and Mass Transfer, Wiley, New York (1990). (Book—not attached).
Jang, J. et al. "Neuro-fuzzy and Soft Computing." Prentice Hall, 1997, pp. 13-89, 199-293, 335-393, 453-496, 535-549.
Kurt Gieck & Reiner Gieck, *Engineering Formulas* § Z.7 (7th ed. 1997).
LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.
Lee et al., "A multi-sample denaturation temperature tester for collagenous biomaterials," Med. Eng. Phy., vol. 17, No. 2, pp. 115-121 (Mar. 1995).
Leonard I. Malis, M.D., "The Value of Irrigation During Bipolar Coagulation," 1989.
Lim et al., "A Review of Mechanism Used in Laparoscopic Surgical Instruments," Mechanism and Machine Theory, vol. 38, pp. 1133-1147, (2003).
Makarov, S. N., Ochmann, M., Desinger, K., "The longitudinal vibration response of a curved fiber used for laser ultrasound surgical therapy," Journal of the Acoustical Society of America 102, 1191-1199 (1997).

McCarus, Steven D. M.D., "Physiologic Mechanism of the Ultrasonically Activated Scalpel," The Journal of the American Association of Gynecologic Laparoscopists; (Aug. 1996), vol. 3, No. 4., pp. 601-606 and 608.
Mitsui Chemicals Names DuPont™ Vespel® Business as Exclusive U.S., European Distributor of AUTUM® Thermoplastic Polyimide Resin, Feb. 24, 2003; http://www2.dupont.com/Vespel/en_US/news_events/article20030224.html.
Moran et al., "Thermally Induced Shrinkage of Joint Capsule," Clinical Orthopaedics and Related Research, No. 281, pp. 248-255 (Dec. 2000).
Morley, L. S. D., "Elastic Waves in a Naturally Curved Rod," Quarterly Journal of Mechanics and Applied Mathematics, 14: 155-172 (1961).
National Semiconductors Temperature Sensor Handbook—http://www.national.com/appinfo/tempsensors/files/temphb.pdf; accessed online: Apr. 1, 2011.
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Sadiq Muhammad et al: "High-performance planar ultrasonic tool based on d31-mode piezocrystal", IEEE Transactions on Ultrasonics, Ferroelectrics and Frequency Control, IEEE, US, vol. 62, No. 3, Mar. 30, 2015 (Mar. 30, 2015), pp. 428-438, XP011574640, ISSN: 0885-3010, DOI: 10.1109/TUFFC.2014.006437.
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
Technology Overview, printed from www.harmonicscalpel.com, Internet site, website accessed on Jun. 13, 2007, (3 pages).
Wall et al., "Thermal modification of collagen," J Shoulder Elbow Surg, No. 8, pp. 339-344 (Jul./Aug. 1999).
Walsh, S. J., White, R. G., "Vibrational Power Transmission in Curved Beams," Journal of Sound and Vibration, 233(3), 455-488 (2000).
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Wright, et al., "Time-Temperature Equivalence of Heat-Induced Changes in Cells and Proteins," Feb., 1998. ASME Journal of Biomechanical Engineering, vol. 120, pp. 22-26.

\* cited by examiner

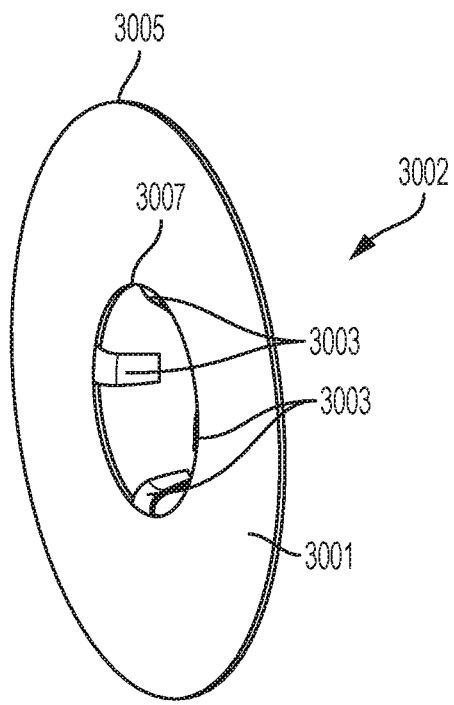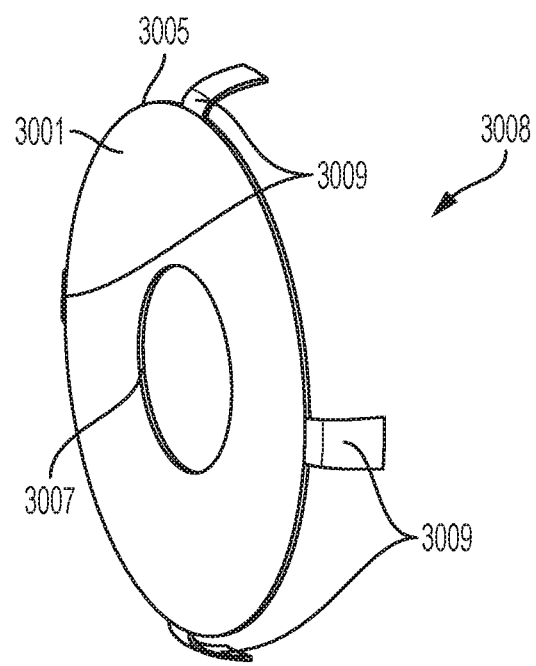
FIG. 30  FIG. 31
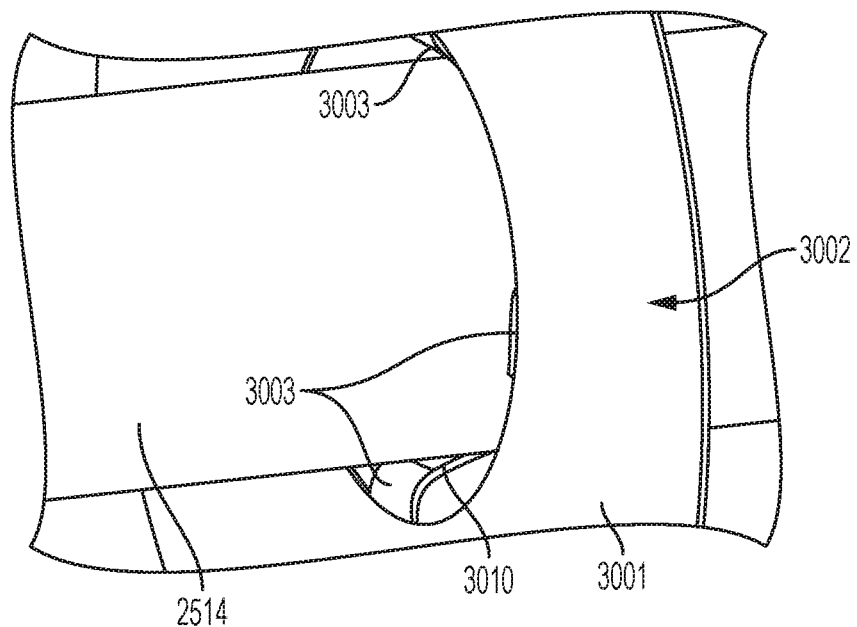
FIG. 32

ULTRASONIC SURGICAL INSTRUMENT WITH PIEZOELECTRIC CENTRAL LUMEN TRANSDUCER

PRIORITY

This application is a divisional application claiming priority under 35 U.S.C. § 121 to U.S. patent application Ser. No. 15/626,768, entitled ULTRASONIC SURGICAL INSTRUMENT WITH PIEZOELECTRIC CENTRAL LUMEN TRANSDUCER, filed Jun. 19, 2017, which issued on Apr. 2, 2019 as U.S. Pat. No. 10,245,064, which claims the benefit of U.S. Provisional Patent Application Ser. No. 62/381,785, entitled ULTRASONIC SURGICAL INSTRUMENT WITH PIEZOELECTRIC CENTRAL LUMEN TRANSDUCER, and filed on Aug. 31, 2016, and U.S. Provisional Patent Application Ser. No. 62/361,136, entitled ULTRASONIC SURGICAL INSTRUMENT WITH PIEZOELECTRIC TRANSDUCER, and filed on Jul. 12, 2016, each of which is herein entirely incorporated by reference.

TECHNICAL FIELD

The present disclosure generally relates to ultrasonic surgical systems and, more particularly, to ultrasonic systems that allows surgeons to perform cutting and coagulation and adapt and customize techniques for performing such procedures.

BACKGROUND

Ultrasonic surgical instruments are finding increasingly widespread applications in surgical procedures by virtue of the unique performance characteristics of such instruments. Depending upon specific instrument configurations and operational parameters, ultrasonic surgical instruments can provide substantially simultaneous cutting of tissue and hemostasis by coagulation, desirably minimizing patient trauma. The cutting action is typically realized by an-end effector, or blade tip, at the distal end of the instrument, which transmits ultrasonic energy to tissue brought into contact with the end effector. Ultrasonic instruments of this nature can be configured for open surgical use, laparoscopic, or endoscopic surgical procedures including robotic-assisted procedures.

Some surgical instruments utilize ultrasonic energy for both precise cutting and controlled coagulation. Ultrasonic energy cuts and coagulates by vibrating a blade in contact with tissue. Vibrating at high frequencies (e.g., 55,500 times per second), the ultrasonic blade denatures protein in the tissue to form a sticky coagulum. Pressure exerted on tissue with the blade surface collapses blood vessels and allows the coagulum to form a hemostatic seal. The precision of cutting and coagulation is controlled by the surgeon's technique and adjusting the power level, blade edge, tissue traction, and blade pressure.

Some areas of improvement for ultrasonic surgical instruments exist. The cost of such instruments remains a barrier for wider applicability. For example, the cost of the transducer has to be lowered substantially to allow for the integration of a transducer into a single patient use device. One of the cost drivers for transducers is the complexity of the piezoelectric element(s) or combination of elements being used. It would be desirable to provide a surgical instrument that overcomes some of the deficiencies of current instruments. The surgical system described herein overcomes those deficiencies.

SUMMARY

According to aspects of the present disclosure, a cost-effective geometry for a piezoelectric transducer production is a round plate or disk. The usage of paired parallel plates in combination with wet assembly, the geometric tolerances of the individual plate surfaces and parallelism may also be used to improve the performance of and lower the cost of ultrasonic surgical instruments. Additionally, aspects of the present disclosure include a combination of an externally compressed piezoelectric stack and a central fluid lumen that combine to form a package enabling an ultrasonic surgical instrument to be used in procedures that require introduction or removal of fluid.

Aspects of the present disclosure also provide improved efficiency relative to a distal flange style half wave transducer because a piezoelectric transducer may be located at the node. Additionally or alternatively, aspects of the present disclosure may provide improved efficiency based on providing a compact form factor (in one aspect, there is a savings of approximately 0.250" on an outer diameter of a transducer assembly), comparative cost savings through elimination of components (e.g. a housing and end cap), robust sealing due to reduction in leak paths, and elimination or reduction of elastomeric components used for sealing. Welded and sealed transducers could be exposed directly to the body, tissues, blood, etc. with a minimal risk of exposure to the moisture-sensitive electrode elements and metallization of the ceramic disks. Accordingly, these aspects may improve longevity of a transducer, which would enable more procedures. An increase in the number of procedures performed can reduce the cost of goods sold further since the costs would be amortized over more procedures.

Aspects of the present disclosure provide a central lumen that can be implemented axisymmetrically about the centerline of an ultrasonic transducer in a transducer assembly for use in an ultrasonic surgical instrument. In many instances, it is desirable to deliver fluid to or remove fluid from the tissue effecting region of an ultrasonic based energy device. A central lumen may act as a conduit for fluid transport. In order to create a spatially economic package, the component reacting to the compression force of the piezoelectric elements of the ultrasonic transducer may be located radially external to the disks. According to aspects, the architecture of a piezoelectric transducer disclosed herein simplifies the implementation of the central lumen. Additionally, external threads (or other fastening mechanism) on the component defining the lumen allow for the constant distribution of material spanning the entire length of the lumen within the transducer. This constant distribution may also negate the need for sealing (based on an O-ring, a interference or press fit, etc.), which may encumber cleaning, sanitizing, or sterilization processes for a surgical instrument. Benefits of the present disclosure may include reduction in the size of radial packages, especially when compared to a centrally located compression mechanism, (e.g. a bolt). Benefits may also include cooler operating temperatures that allow for higher available tissue power, elimination of the necessity of lumen sealing within an ultrasonic transducer region, facilitation of simple electrical connections, and alignment of electrodes for construction of the transducer assembly.

In one aspect, an apparatus is provided for dissecting and coagulating tissue. The apparatus comprises: a surgical instrument having an end effector configured to interact with a tissue at a distal end thereof, a generator electrically coupled to the surgical instrument and configured to deliver ultrasonic energy to the end effector to allow the end effector to interact with the tissue. The surgical instrument comprises a transducer assembly comprising a housing and an ultrasonic transducer, where the ultrasonic transducer comprises a plurality of piezoelectric elements and a plurality of electrodes arranged in a stack configuration Each of the plurality of electrodes is located between each pair of solid piezoelectric elements, with an end mass positioned adjacent a first end of the ultrasonic transducer. The end mass is configured to engage with the housing and the end mass is configured to compress the ultrasonic transducer against an interior surface of the housing when the end mass is engaged with the housing.

In another aspect, the surgical instrument comprises a transducer assembly comprising a housing; an ultrasonic transducer comprising a plurality of solid piezoelectric elements and a plurality of electrodes arranged in a stack configuration having a longitudinal axis, a first end, and a second end, wherein each of a plurality of electrodes is located between each pair of solid piezoelectric elements such that an electrode is located at the first end of the stack configuration, and an electrode is located at the second end of the stack configuration; an end mass positioned along the longitudinal axis adjacent a first end of the ultrasonic transducer and coupled to the ultrasonic transducer, where the end mass is configured to engage with the housing, where the end mass is configured to compress the ultrasonic transducer against an interior surface of the housing when the end mass is engaged with the housing, and where a first solid piezoelectric element of the plurality of solid piezoelectric elements and a second solid piezoelectric element of the plurality of solid piezoelectric elements are electrically connected in parallel.

In another aspect, a surgical instrument comprises a transducer assembly comprising a housing, an ultrasonic transducer, and an end mass having a first end, a second end, and an aperture therethrough. The ultrasonic transducer comprises a plurality of piezoelectric elements and a plurality of electrodes arranged in a stack configuration having a first end and a second end, wherein a first electrode is located between a first pair of piezoelectric elements, a second electrode is located between a second pair of piezoelectric elements, a third electrode is located at the first end of the stack configuration, and a fourth electrode is located at the second end of the stack configuration, a first spacer element positioned in contact with the third electrode, and a second spacer element positioned in contact with the fourth electrode. The end mass is positioned adjacent a first end of the ultrasonic transducer, wherein the end mass is configured to engage with the housing and the end mass is configured to compress the ultrasonic transducer against an interior surface of the housing when the end mass is engaged with the housing. In addition, the first end of the end mass contacts the first spacer element when the end mass compresses the ultrasonic transducer and the second spacer element contacts the interior surface of the housing when the end mass compresses the ultrasonic transducer.

In another aspect, a surgical instrument for coagulating and dissecting tissue comprises a transducer assembly that comprises a housing, an ultrasonic transducer, and an end mass. The housing comprises a conduit section and a base portion, where a fluid passageway is defined through the conduit section and the base portion. The ultrasonic transducer comprises a plurality of piezoelectric elements and a plurality of electrodes arranged in a stack configuration, where each of the plurality of electrodes is located between each pair of piezoelectric elements and a first borehole is defined through the ultrasonic transducer. The end mass comprises a second borehole defined therethrough, a surface of the end mass is positioned adjacent a first end of the ultrasonic transducer, and the end mass is configured to engage with the housing. Further, the conduit section of the housing is configured to pass through the first borehole of the ultrasonic transducer and the second borehole of the end mass and the end mass is configured to compress the ultrasonic transducer against an interior surface of the housing when the end mass is engaged with the housing.

In another aspect, a surgical instrument for coagulating and dissecting tissue comprises a transducer assembly that comprises a housing, an ultrasonic transducer, and an end mass. The housing comprises a conduit section and a base portion, where a fluid passageway is defined through the conduit section and the base portion. The ultrasonic transducer comprises a plurality of piezoelectric elements and a plurality of electrodes arranged in a stack configuration, and the ultrasonic transducer has a longitudinal axis, a first end, and a second end. A first borehole is defined through the ultrasonic transducer, where each of the plurality of electrodes is located between each pair of piezoelectric elements, a second electrode is located at the first end of the ultrasonic transducer, and a third electrode is located at the second end of the ultrasonic transducer. The end mass comprises a second borehole defined therethrough and the end mass positioned along the longitudinal axis and adjacent a first end of the ultrasonic transducer, where the end mass is configured to engage with the housing. The conduit section of the housing is configured to pass through the first borehole of the ultrasonic transducer and the second borehole of the end mass, and the end mass is configured to compress the ultrasonic transducer against a surface of the housing when the end mass is engaged with the housing, and a first piezoelectric element of the plurality of piezoelectric elements and a second piezoelectric element of the plurality of piezoelectric elements are electrically connected in parallel.

In another aspect, a transducer assembly comprises a housing, a conductive element, an insulator, and an ultrasonic transducer. The housing comprises a conduit section and a base portion, where a fluid passageway is defined through the conduit section and the base portion. The conductive element at least partially surrounds the conduit section of the housing and the insulator is positioned between the conductive element and the conduit section so that the insulator electrically isolates the conductive element from the conduit section. The ultrasonic transducer comprises a plurality of piezoelectric elements and a plurality of electrodes arranged in a stack configuration. The ultrasonic transducer has a longitudinal axis, a first end, and a second end, where a first borehole is defined through the ultrasonic transducer, each of the plurality of electrodes is located between each pair of piezoelectric elements, a second electrode is located at the first end of the ultrasonic transducer, and a third electrode is located at the second end of the ultrasonic transducer. Further, each of the plurality of electrodes is electrically coupled to the conductive element. The end mass comprises a second borehole defined therethrough and the end mass is positioned along the longitudinal axis and adjacent a first end of the ultrasonic transducer. The end mass is configured to engage with the housing, the conduit section of the housing is configured to pass through the first borehole of the ultrasonic transducer and the second borehole of the end mass, the end mass is configured to compress the ultrasonic transducer against a surface of the housing when the end mass is engaged with the housing, and a first piezoelectric element of the plurality of piezoelectric elements and a second piezoelectric element of the plurality of piezoelectric elements are electrically connected in parallel.

In addition to the foregoing, various other method and/or system and/or program product aspects are set forth and described in the teachings such as text (e.g., claims and/or detailed description) and/or drawings of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

In one or more various aspects, related systems include but are not limited to circuitry and/or programming for effecting herein-referenced method aspects; the circuitry and/or programming can be virtually any combination of hardware, software, and/or firmware configured to affect the herein-referenced method aspects depending upon the design choices of the system designer. In addition to the foregoing, various other method and/or system aspects are set forth and described in the teachings such as text (e.g., claims and/or detailed description) and/or drawings of the present disclosure.

Further, it is understood that any one or more of the following-described aspects, expressions of aspects, examples, can be combined with any one or more of the other following-described aspects, expressions of aspects, and examples.

The foregoing summary is illustrative only and is not intended to be in any way limiting. In addition to the illustrative aspects, forms, and features described above, further aspects, forms, and features will become apparent by reference to the drawings and the following detailed description.

FIGURES

The novel features of the described aspects are set forth with particularity in the appended claims. The described aspects, however, both as to organization and methods of operation, may be best understood by reference to the following description, taken in conjunction with the accompanying drawings in which:

FIG. 30 is a perspective view of an aspect of an electrode of the ultrasonic transducer assembly shown in FIG. 25;

FIG. 31 is a perspective view of an aspect of an electrode of the ultrasonic transducer assembly shown in FIG. 25;

FIG. 32 is a close up view of an aspect of an electrode and conductive element of the ultrasonic transducer assembly shown in FIG. 25; and

DESCRIPTION

Figure 1:
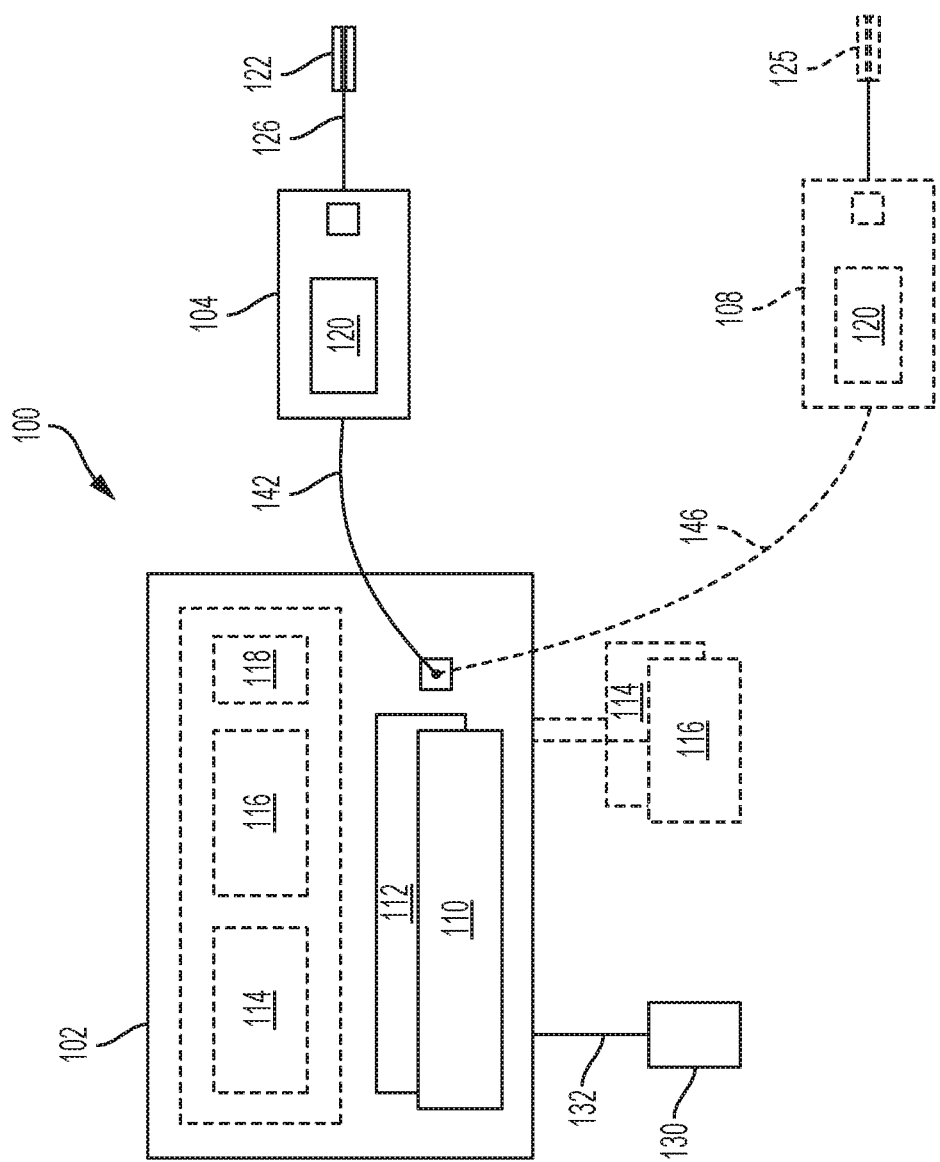
FIG. 1 is a diagram of one aspect of a surgical system comprising a generator and various surgical instruments usable therewith.

Before explaining various aspects of surgical instruments in detail, it should be noted that the illustrative aspects are not limited in application or use to the details of construction and arrangement of parts illustrated in the accompanying drawings and description. The illustrative aspects may be implemented or incorporated in other aspects, variations and modifications, and may be practiced or carried out in various ways. Further, unless otherwise indicated, the terms and expressions utilized herein have been chosen for the purpose of describing the illustrative aspects for the convenience of the reader and are not for the purpose of limitation thereof.

Further, it is understood that any one or more of the following-described aspects, expressions of aspects, examples, can be combined with any one or more of the other following-described aspects, expressions of aspects, and examples.

Various aspects are directed to improved ultrasonic and/or combination electrosurgical (RF) and ultrasonic instruments configured for effecting tissue dissecting, cutting, and/or coagulation during surgical procedures. In one aspect, a combined ultrasonic and electrosurgical instrument may be configured for use in open surgical procedures, but has applications in other types of surgery, such as laparoscopic, endoscopic, and robotic-assisted procedures. Versatile use is facilitated by selective use of ultrasonic and/or ultrasonic and RF energy.

The various aspects will be described in association with an ultrasonic instrument as described herein. Such description is provided by way of example, and not limitation, and is not intended to limit the scope and applications thereof. For example, any one of the described aspects is useful in combination with a multitude of ultrasonic instruments including those described in, for example, U.S. Pat. Nos. 5,322,055; 5,449,370; 5,630,420; 5,935,144; 5,938,633; 5,944,737; 5,954,736; 6,278,218; 6,283,981; 6,309,400; 6,325,811; 6,387,109; 6,491,708; 7,821,143; 8,147,508; 8,152,825; 8,277,471; 8,430,898; 8,512,364; 8,882,792; and 9,114,245; and U.S. Patent Application Publication Nos. US20050192612; US2011/0040212; US2011/0040213; US20120215244; 20130090576; 20130197550; and US20130253558, each of which are incorporated by reference herein in its entirety.

As will become apparent from the following description, it is contemplated that aspects of the surgical instruments described herein may be used in association with an oscillator unit of a surgical system, whereby ultrasonic energy from the oscillator unit provides the desired ultrasonic actuation for the present surgical instrument. It is also contemplated that aspects of the surgical instrument described herein may be used in association with a signal generator unit of a surgical system, whereby electrical energy in the form of radio frequencies (RF), for example, is used to provide feedback to the user regarding the surgical instrument. The ultrasonic oscillator and/or the signal generator unit may be non-detachably integrated with the surgical instrument or may be provided as separate components, which can be electrically attachable to the surgical instrument.

One aspect of the present surgical apparatus is particularly configured for disposable use by virtue of its straightforward construction. However, it is also contemplated that other aspects of the present surgical instrument can be configured for non-disposable or multiple uses. Detachable connection of the present surgical instrument with an associated oscillator and signal generator unit is presently disclosed for single-patient use for illustrative purposes only. However, non-detachable integrated connection of the present surgical instrument with an associated oscillator and/or signal generator unit is also contemplated. Accordingly, various aspects of the presently described surgical instruments may be configured for single use and/or multiple use with either detachable and/or non-detachable integral oscillator and/or signal generator unit, without limitation, and all combinations of such configurations are contemplated to be within the scope of the present disclosure.

Figure 2:
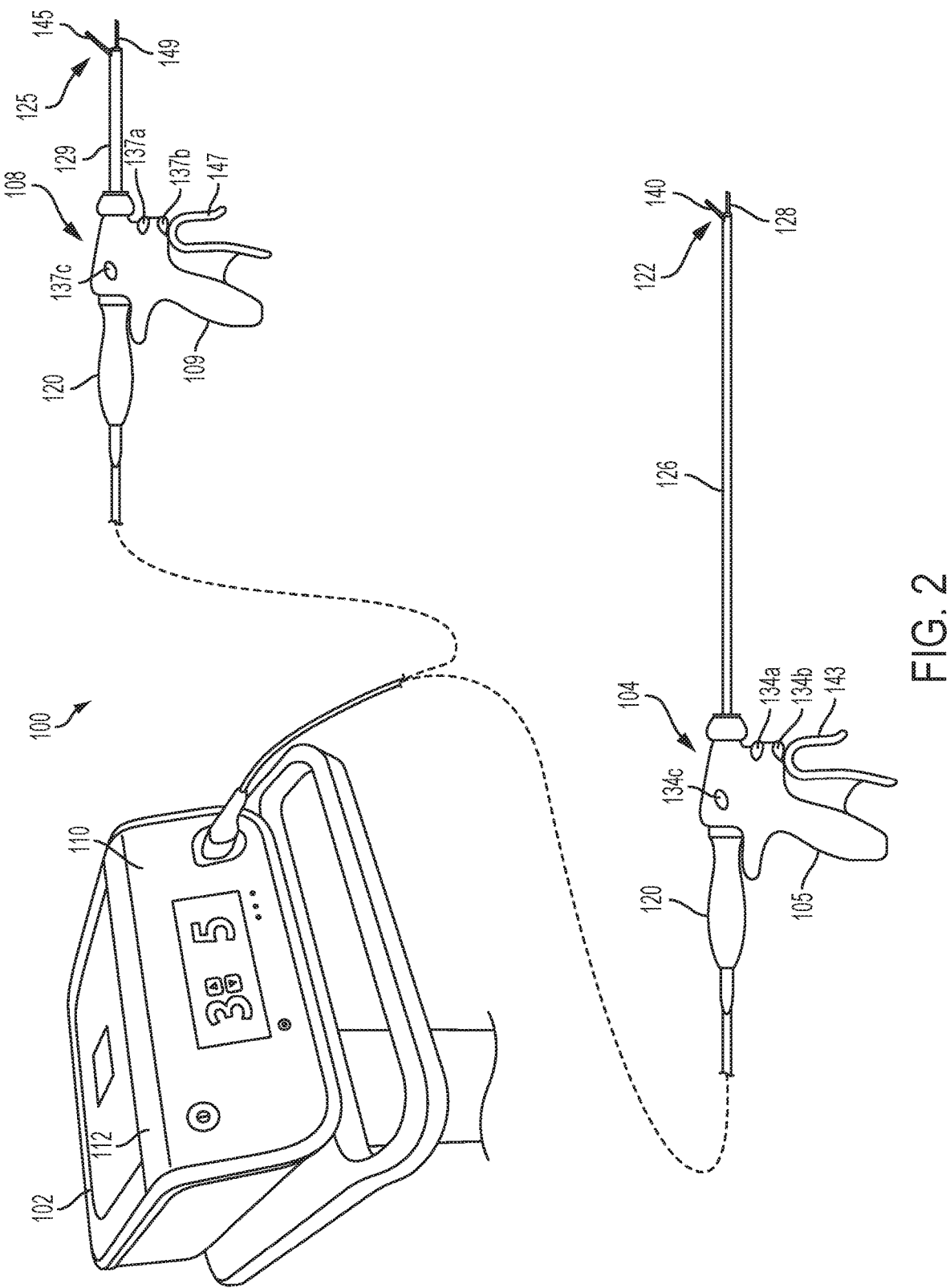
FIG. 2 is a diagram of various aspects of the surgical system shown in FIG. 1.
Figure 3:
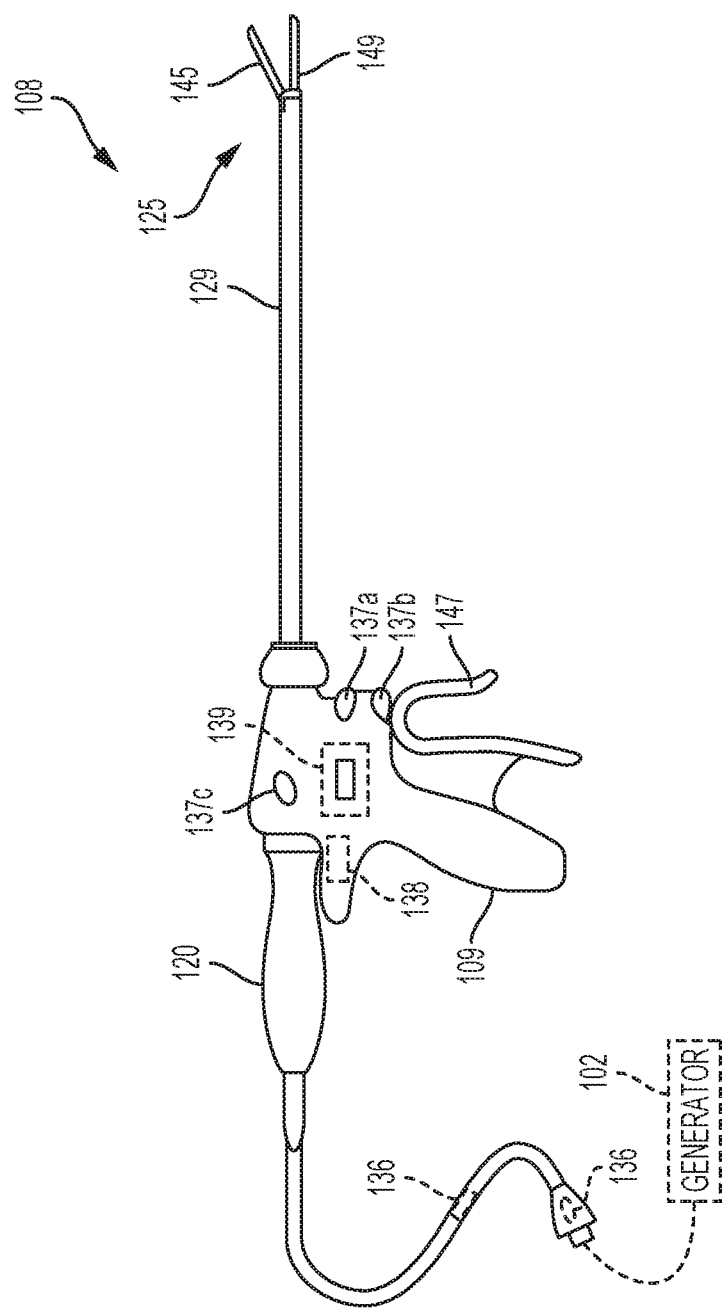
FIG. 3 is a diagram of one aspect of the combination ultrasonic and electrosurgical instrument of FIGS. 1 and 2.

With reference to FIGS. 1-3, one aspect of a surgical system 100 including an ultrasonic surgical instrument is described. FIGS. 1 and 2 illustrate one aspect of a surgical system 100 comprising a generator 102 and various surgical instruments 104, 108 usable with the surgical system 100. FIG. 3 is a diagram of the ultrasonic surgical instrument 104 of FIGS. 1 and 2.

In various aspects, the generator 102 may comprise several separate functional elements, such as modules and/or blocks. Different functional elements or modules may be configured for driving the different kinds of surgical instruments 104, 108. For example, an ultrasonic generator drive circuit 114 may drive ultrasonic devices such as the ultrasonic surgical instrument 104 via a cable 142. An electrosurgery/RF generator drive circuit 116 may drive the electrosurgical instrument (not shown) via a cable (not shown). For example, the respective drive circuits 114, 116 may generate respective drive signals for driving an appropriate surgical instrument 104, 108. In various aspects, the ultrasonic generator drive circuit 114 (e.g., ultrasonic drive circuit) and/or the electrosurgery/RF generator drive circuit 116 (e.g., RF drive circuit) each may be formed integrally with the generator 102. Alternatively, one or more of the drive circuits 114, 116 may be provided as a separate circuit module electrically coupled to the generator 102. (The drive circuits 114 and 116 are shown in phantom to illustrate this option.) Also, in some aspects, the electrosurgery/RF generator drive circuit 116 may be formed integrally with the ultrasonic generator drive circuit 114, or vice versa. Also, in some aspects, the generator 102 may be omitted entirely and the drive circuits 114, 116 may be executed by processors or other hardware within the respective surgical instruments 104, 108.

In other aspects, the electrical outputs of the ultrasonic generator drive circuit 114 and the electrosurgery/RF generator drive circuit 116 may be combined into a single drive circuit to provide a single electrical signal capable of driving the multifunction surgical instrument 108 simultaneously with electrosurgical RF and ultrasonic energies via a cable 146. The multifunction surgical instrument 108 comprises an ultrasonic transducer component 120 coupled to an ultrasonic blade 149 and one or more electrodes in the end effector 124 to receive electrosurgical RF energy. In such implementations, the combined RF/ultrasonic signal is coupled to the multifunction surgical instrument 108. The multifunction surgical instrument 108 comprises signal processing components to split the combined RF/ultrasonic signal such that the RF signal can be delivered to the electrodes in the end effector 125 and the ultrasonic signal can be delivered to the ultrasonic transducer component 120.

In accordance with the described aspects, the ultrasonic generator drive circuit 114 may produce a drive signal or signals of particular voltages, currents, and frequencies, e.g., 55,500 cycles per second (Hz). The drive signal or signals may be provided to the ultrasonic surgical instrument 104, and specifically to the transducer component 120, which may operate, for example, as described herein. The transducer component 120 and a waveguide extending through the shaft 126 (waveguide not shown in FIG. 1) may collectively form an ultrasonic drive system driving an ultrasonic blade 128 of an end effector 122. In one aspect, the generator 102 may be configured to produce a drive signal of a particular voltage, current, and/or frequency output signal that can be modified with high resolution, accuracy, and repeatability.

The generator 102 may be activated to provide the drive signal to the transducer component 120 in any suitable manner. For example, the generator 102 may comprise a foot switch 130 coupled to the generator 102 via a foot switch cable 132. A clinician may activate the transducer component 120 by depressing the foot switch 130. In addition, or instead of the foot switch 130 some aspects of the ultrasonic surgical instrument 104 may utilize one or more switches positioned on the hand piece that, when activated, may cause the generator 102 to activate the transducer component 120. In one aspect, for example, the one or more switches may comprise a pair of toggle buttons 134a, 134b (FIG. 2), for example, to determine an operating mode of the surgical instrument 104. When the toggle button 134a is depressed, for example, the ultrasonic generator 102 may provide a maximum drive signal to the transducer component 120, causing it to produce maximum ultrasonic energy output. Depressing toggle button 134b may cause the ultrasonic generator 102 to provide a user-selectable drive signal to the transducer component 120, causing it to produce less than the maximum ultrasonic energy output. The surgical instrument 104 additionally or alternatively may comprise a second switch (not shown) to, for example, indicate a position of a jaw closure trigger for operating jaws of the end effector 122. Also, in some aspects, the ultrasonic generator 102 may be activated based on the position of the jaw closure trigger, (e.g., as the clinician depresses the jaw closure trigger to close the jaws, ultrasonic energy may be applied). Additionally or alternatively, the one or more switches may comprise a toggle button 134c that, when depressed, causes the generator 102 to provide a pulsed output. The pulses may be provided at any suitable frequency and grouping, for example. In certain aspects, the power levels of the pulses may be the same as the power levels associated with toggle buttons 134a, 134b (maximum, less than maximum), for example.

In accordance with the described aspects, the electrosurgery/RF generator drive circuit 116 may generate a drive signal or signals with output power sufficient to perform bipolar electrosurgery using radio frequency (RF) energy. In bipolar electrosurgery applications, the drive signal may be provided, for example, to electrodes of an electrosurgical instrument (not shown), for example. Accordingly, the generator 102 may be configured for therapeutic purposes by applying electrical energy to the tissue sufficient for treating the tissue (e.g., coagulation, cauterization, tissue welding).

The generator 102 may comprise an input device 110 located, for example, on a front panel of the generator 102 console. The input device 110 may comprise any suitable device that generates signals suitable for programming the operation of the generator 102. In operation, the user can program or otherwise control operation of the generator 102 using the input device 110. The input device 110 may comprise any suitable device that generates signals that can be used by the generator (e.g., by one or more processors contained in the generator) to control the operation of the generator 102 (e.g., operation of the ultrasonic generator drive circuit 114 and/or electrosurgery/RF generator drive circuit 116). In various aspects, the input device 110 includes one or more of buttons, switches, thumbwheels, keyboard, keypad, touch screen monitor, pointing device, remote connection to a general purpose or dedicated computer. In other aspects, the input device 110 may comprise a suitable user interface, such as one or more user interface screens displayed on a touch screen monitor, for example. Accordingly, by way of the input device 110, the user can set or program various operating parameters of the generator, such as, for example, current (I), voltage (V), frequency (f), and/or period (T) of a drive signal or signals generated by the ultrasonic generator drive circuit 114 and/or electrosurgery/RF generator drive circuit 116.

The generator 102 also may comprise an output device 112 (FIGS. 1, 2), such as an output indicator, located, for example, on a front panel of the generator 102 console. The output device 112 includes one or more devices for providing a sensory feedback to a user. Such devices may comprise, for example, visual feedback devices (e.g., a visual feedback device may comprise incandescent lamps, light emitting diodes (LEDs), graphical user interfaces (GUIs), displays, analog indicators, digital indicators, bar graph displays, digital alphanumeric displays, light crystal display (LCD) display screens, LED indicators), audio feedback devices (e.g., an audio feedback device may comprise speakers, buzzers, audible devices, computer generated tones, computerized speechs, voice user interfaces (VUIs) to interact with computers through a voice/speech platform), or tactile feedback devices (e.g., a tactile feedback device comprises any type of vibratory feedback, haptic actuator).

In one aspect, the ultrasonic generator drive circuit 114 and electrosurgery/RF drive circuit 116 may comprise one or more embedded applications implemented as firmware, software, hardware, or any combination thereof. The drive circuits 114, 116 may comprise various executable modules such as software, programs, data, drivers, application program interfaces (APIs), and so forth. The firmware may be stored in nonvolatile memory (NVM), such as in bit-masked read-only memory (ROM) or flash memory. In various implementations, storing the firmware in ROM may preserve flash memory. The NVM may comprise other types of memory including, for example, programmable ROM (PROM), erasable programmable ROM (EPROM), electrically erasable programmable ROM (EEPROM), or battery backed random-access memory (RAM) such as dynamic RAM (DRAM), Double-Data-Rate DRAM (DDRAM), and/or synchronous DRAM (SDRAM).

In one aspect, the drive circuits 114, 116 comprise a hardware component implemented as a processor for executing program instructions for monitoring various measurable characteristics of the surgical instruments 104, 108 and generating a corresponding output control signals for operating the surgical instruments 104, 108. In aspects in which the generator 102 is used in conjunction with the surgical instrument 104, the output control signal may drive the ultrasonic transducer component 120 in cutting and/or coagulation operating modes. Electrical characteristics of the surgical instrument 104 and/or tissue may be measured and used to control operational aspects of the generator 102 and/or provided as feedback to the user. In aspects in which the generator 102 is used in conjunction with an electrosurgical instrument, the output control signal may supply electrical energy (e.g., RF energy) to the end effector of the electrosurgical instrument in cutting, coagulation and/or desiccation modes. Electrical characteristics of the electrosurgical instrument and/or tissue may be measured and used to control operational aspects of the generator 102 and/or provide feedback to the user. In various aspects, as previously discussed, the hardware component may be implemented as a digital signal processor (DSP), programmable logic device (PLD), application-specific integrated circuit (ASIC), other circuit, and/or register. In one aspect, the processor may be configured to store and execute computer software program instructions to generate the output signal functions for driving various components of the surgical instruments 104, 108, such as the ultrasonic transducer component 120 and the end effectors 122, 125.

Although certain modules, circuits, and/or blocks of the generator 102 may be described by way of example, it can be appreciated that a greater or lesser number of modules, circuits, and/or blocks may be used and still fall within the scope of the aspects. Further, although various aspects may be described in terms of modules, circuits, and/or blocks to facilitate description, such modules, circuits, and/or blocks may be implemented by one or more hardware components, e.g., processors, DSPs, PLDs, ASICs, circuits, registers and/or software components, e.g., programs, subroutines, logic and/or combinations of hardware and software components. Also, in some aspects, the various modules described herein may be implemented utilizing similar hardware positioned within the surgical instruments 104, 108 (i.e., the generator 102 may be omitted).

FIG. 2 illustrates generator 102 configured to drive multiple surgical instruments 104, 108. The first surgical instrument 104 comprises a handpiece 105, an ultrasonic transducer component 120, a shaft 126, and an end effector 122. The end effector 122 comprises an ultrasonic blade 128 acoustically coupled to the transducer component 120 and a clamp arm 140. The handpiece 105 comprises a trigger 143 to operate the clamp arm 140 and a combination of the toggle buttons 134a, 134b, 134c to energize and drive the ultrasonic blade 128 or other function. The toggle buttons 134a, 134b, 134c can be configured to energize the ultrasonic transducer component 120 with the generator 102. Still with reference to FIG. 2, the generator 102 also is configured to drive a combination electrosurgical and ultrasonic instrument 108. The combination electrosurgical and ultrasonic multifunction surgical instrument 108 comprises a handpiece 109, a shaft 129, and an end effector 125. The end effector comprises an ultrasonic blade 149 and a clamp arm 145. The ultrasonic blade 149 is acoustically coupled to the ultrasonic transducer component 120. The handpiece 109 comprises a trigger 147 to operate the clamp arm 145 and a combination of the toggle buttons 137a, 137b, 137c to energize and drive the ultrasonic blade 149 or other function. The toggle buttons 137a, 137b, 137c can be configured to energize the ultrasonic transducer component 120 with the generator 102 and energize the ultrasonic blade 149 with a bipolar energy source also contained within the generator 102. The generator 102 is coupled to an ultrasonic transducer component 120 of the combination electrosurgical and ultrasonic instrument 108 via a cable 142.

The generator 102 also is configured to drive a surgical instrument 104. The generator 102 is coupled to an ultrasonic transducer component 120 of the surgical instrument 104 via a cable 146 (See FIG. 1). The ultrasonic transducer component 120 of the surgical instrument 104 and a waveguide extending through a shaft 126 (waveguide not shown in FIG. 2) may collectively form an ultrasonic drive system driving an ultrasonic blade 128 of an end effector 122. The end effector 122 further may comprise a clamp arm 140 to clamp tissue between the clamp arm 140 and the ultrasonic blade 128. In one aspect, the generator 102 may be configured to produce a drive signal of a particular voltage, current, and/or frequency output signal that can be stepped or otherwise modified with high resolution, accuracy, and repeatability.

It will be appreciated that the surgical instrument 104 may comprise any combination of the toggle buttons 134a, 134b, 134c. For example, the surgical instrument 104 could be configured to have only two toggle buttons: a toggle button 134a for producing maximum ultrasonic energy output and a toggle button 134c for producing a pulsed output at either the maximum or less than maximum power level. In this way, the drive signal output configuration of the generator 102 could be 5 continuous signals and or a suitable number of (e.g. between 1 to 5) pulsed signals. In certain aspects, the specific drive signal configuration may be controlled based upon, for example, EEPROM settings in the generator 102 and/or user power level selection(s). In certain aspects, a two-position switch may be provided as an alternative to a toggle button 134c. For example, a surgical instrument 104 may include a toggle button 134a for producing a continuous output at a maximum power level and a two-position toggle button 134b. In a first position, toggle button 134b may produce a continuous output at a less than maximum power level, and in a second position the toggle button 134b may produce a pulsed output (e.g., at either a maximum or less than maximum power level, depending upon the EEPROM settings).

With reference to FIG. 3, aspects of the generator 102 may enable communication with instrument-based data circuits. For example, the generator 102 may be configured to communicate with a first data circuit 136 and/or a second data circuit 138. For example, the first data circuit 136 may indicate a burn-in frequency slope, as described herein. Additionally or alternatively, any type of information may be communicated to second data circuit 138 for storage therein via a data circuit interface (e.g., using a logic device). Such information may comprise, for example, an updated number of operations in which the instrument has been used and/or dates and/or times of its usage. In certain aspects, the second data circuit may transmit data acquired by one or more sensors (e.g., an instrument-based temperature sensor). In certain aspects, the second data circuit 138 may receive data from the generator 102 and provide an indication to a user (e.g., an LED indication or other visible indication) based on the received data. The second data circuit 138 may be contained in the multifunction surgical instrument 108. In some aspects, the second data circuit 138 may be implemented in a manner similar to that of the first data circuit 136 described herein.

An instrument interface circuit may comprise a second data circuit 138 interface to enable this communication. In one aspect, the second data circuit interface may comprise a tri-state digital interface, although other interfaces also may be used. In certain aspects, the second data circuit 138 may generally be any circuit for transmitting and/or receiving data. In one aspect, for example, the second data circuit 138 may store information pertaining to the particular surgical instrument with which it is associated. Such information may include, for example, a model number, a serial number, a number of operations in which the surgical instrument has been used, and/or any other type of information. In some aspects, the second data circuit 138 may store information about the electrical and/or ultrasonic properties of an associated transducer component 120, end effector 122, or ultrasonic drive system. Various processes and techniques described herein may be executed by a generator. It will be appreciated, however, that in certain aspects, all or a part of these processes and techniques may be performed by internal logic 139 of the multifunction surgical instrument 108.

Furthermore, the generator 102 may be configured to functionally operate in a manner similar to the GEN300 sold by Ethicon Endo-Surgery, Inc. of Cincinnati, Ohio as is disclosed in one or more of the following U.S. patents, all of which are incorporated by reference herein: U.S. Pat. No. 6,480,796 (Method for Improving the Start Up of an Ultrasonic System Under Zero Load Conditions); U.S. Pat. No. 6,537,291 (Method for Detecting a Loose Blade in a Hand Piece Connected to an Ultrasonic Surgical System); U.S.

Pat. No. 6,662,127 (Method for Detecting Presence of a Blade in an Ultrasonic System); U.S. Pat. No. 6,679,899 (Method for Detecting Transverse Vibrations in an Ultrasonic Hand Piece); U.S. Pat. No. 6,977,495 (Detection Circuitry for Surgical Handpiece System); U.S. Pat. No. 7,077,853 (Method for Calculating Transducer Capacitance to Determine Transducer Temperature); U.S. Pat. No. 7,179,271 (Method for Driving an Ultrasonic System to Improve Acquisition of Blade Resonance Frequency at Startup); and U.S. Pat. No. 7,273,483 (Apparatus and Method for Alerting Generator Functions in an Ultrasonic Surgical System).

Figure 4:
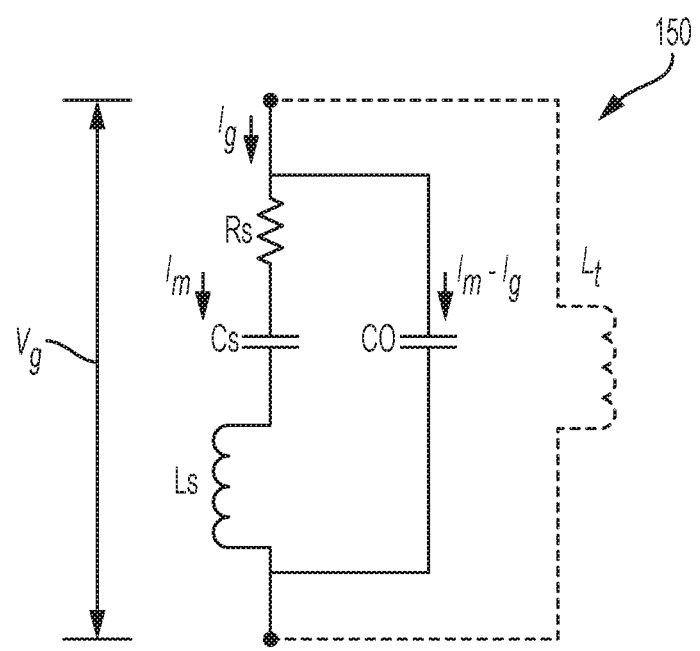
FIG. 4 is a model of one aspect of an equivalent circuit of an ultrasonic transducer illustrating a motional branch current.

FIG. 4 illustrates an equivalent circuit 150 of an ultrasonic transducer, such as the ultrasonic transducer component 120 shown in FIGS. 1-3, according to one aspect. The circuit 150 comprises a first "motional" branch having a serially connected inductance $L_s$, resistance $R_s$ and capacitance $C_s$ that define the electromechanical properties of the resonator, and a second capacitive branch having a static capacitance $C_o$. Drive current $I_g$ may be received from a generator at a drive voltage $V_g$, with motional current $I_m$ flowing through the first branch and current $I_g$-$I_m$ flowing through the capacitive branch. Control of the electromechanical properties of the ultrasonic transducer may be achieved by suitably controlling $I_g$ and $V_g$. As explained above, conventional generator architectures may include a tuning inductor $L_t$ (shown in phantom in FIG. 4) for tuning out in a parallel resonance circuit the static capacitance Co at a resonant frequency so that substantially all of generator's current output $I_g$ flows through the motional branch. In this way, control of the motional branch current $I_m$ is achieved by controlling the generator current output $I_g$. The tuning inductor $L_t$ is specific to the static capacitance $C_o$ of an ultrasonic transducer, however, and a different ultrasonic transducer having a different static capacitance requires a different tuning inductor $L_t$. Moreover, because the tuning inductor $L_t$ is matched to the nominal value of the static capacitance $C_o$ at a particular resonant frequency, accurate control of the motional branch current $I_m$ is assured only at that particular frequency, and as frequency shifts down with transducer temperature, accurate control of the motional branch current is compromised.

Aspects of the generator 102 shown in FIGS. 1-3 may be configured such that they do not rely on a tuning inductor $L_t$ to monitor the motional branch current $I_m$. Instead, the generator 102 may use the measured value of the static capacitance $C_o$ in between applications of power for a specific ultrasonic surgical instrument 104 (along with drive signal voltage and current feedback data) to determine values of the motional branch current $I_m$ on a dynamic and ongoing basis (e.g., in real-time). Such aspects of the generator 102 are therefore able to provide virtual tuning to simulate a system that is tuned or resonant with any value of static capacitance $C_o$ at any frequency, and not just at the resonant frequency dictated by a nominal value of the static capacitance $C_o$.

It is noted, for the purpose of describing the various aspects of the present disclosure, that an ultrasound transducer assembly is a transducer assembly which ultrasonically vibrates an ultrasonically-vibratable medical-treatment instrument (such as, without limitation, an ultrasonic scalpel or an ultrasonic clamp), when attached to the transducer assembly, in a mode of vibration at a fundamental frequency (i.e., a fundamental resonant frequency), that a node is a node of vibration (i.e., a location of zero magnitude of vibration), and that an antinode is a location of maximum magnitude of vibration. Examples of modes of vibration include, without limitation, a longitudinal mode of vibration, a torsional mode of vibration, a bending mode of vibration, and a swelling mode of vibration, wherein the transducer assembly is not limited to operating in a single mode of vibration as is known to those skilled in the art. Also, the terminology "gain stage" means a positive gain stage and is a longitudinally-extending portion of the transducer assembly which results in increased magnitude of vibration. Gain stages may be provided by a portion of the transducer assembly having at least one of a reduced diameter (as identified in some of the figures), a (constant or non-constant) taper, or being of a different material, as is known to those skilled in the art. It is pointed out that piezoelectric transducer disks are not limited to those with an outer perimeter having a circular shape and may include those with an outer perimeter having another shape such as, without limitation, an elliptical shape.

In one aspect, the present disclosure describes a surgical instrument that includes a transducer assembly comprising a housing, an ultrasonic transducer comprising a plurality of piezoelectric elements in a stack configuration, and an end mass where the end mass is configured to engage the housing and hold the ultrasonic transducer in a particular relationship within the housing. According to aspects, the end mass compresses the ultrasonic transducer within a horn shaped portion of the housing. A first surface of the end mass contacts a first surface of the ultrasonic transducer and when the end mass engages with the housing, a second surface of the ultrasonic transducer is compressed against an interior surface of the horn shaped portion of the housing. The compression of the ultrasonic transducer is caused due to the engagement between the end mass and the housing. Such compression is independent of a bolt or screw that might otherwise be passed through the piezoelectric elements and torqued into the housing. The transducer assembly may be acoustically coupled to an ultrasonic blade of an end effector at a distal end of the surgical instrument and the surgical instrument may be an ultrasonic surgical instrument or a combination ultrasonic and electrosurgical instrument similar to that shown in FIGS. 1-3. The transducer assembly, and hence the ultrasonic transducer, is configured to receive a drive signal from a generator to cause ultrasonic motion of the ultrasonic blade. Further, the terms "proximal" and "distal" may used with reference the proximity or location of components of the transducer assembly based on where a clinician may grip a surgical instrument that comprises the transducer assembly.

Figure 5:
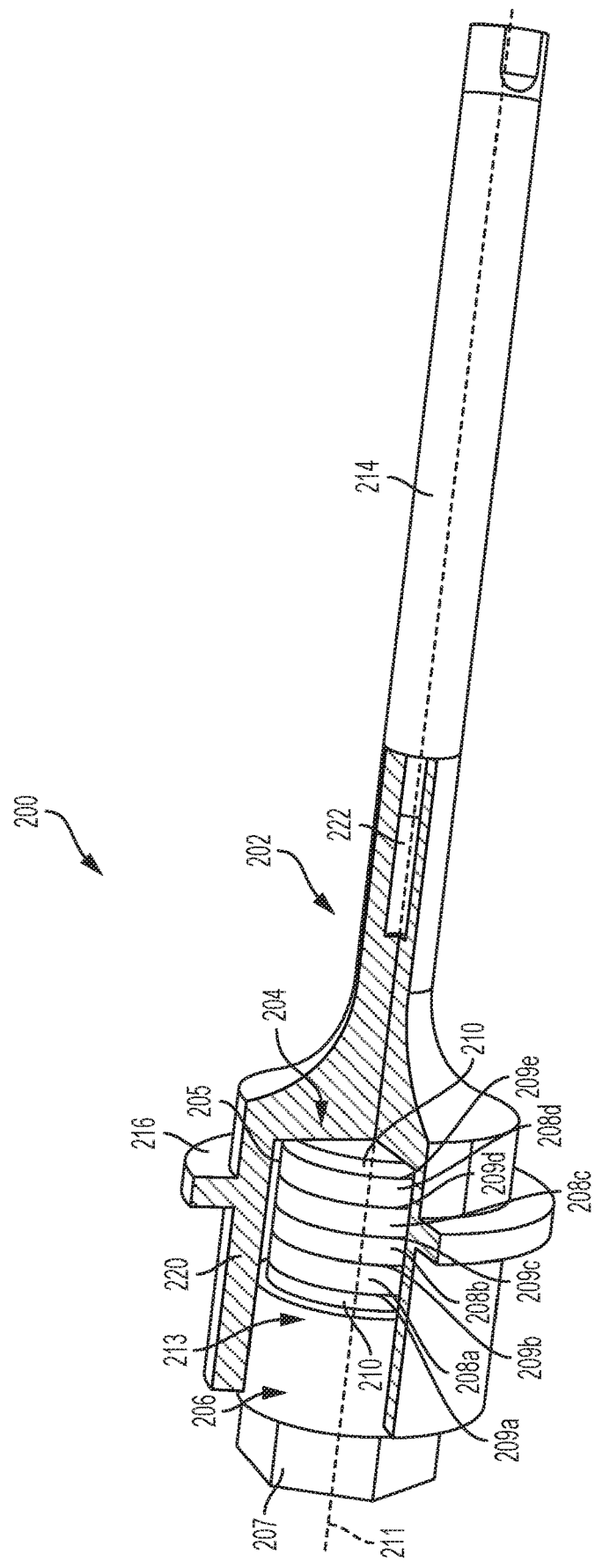
FIG. 5 is a partial sectional view of one aspect of an ultrasonic transducer assembly.
Figure 6:
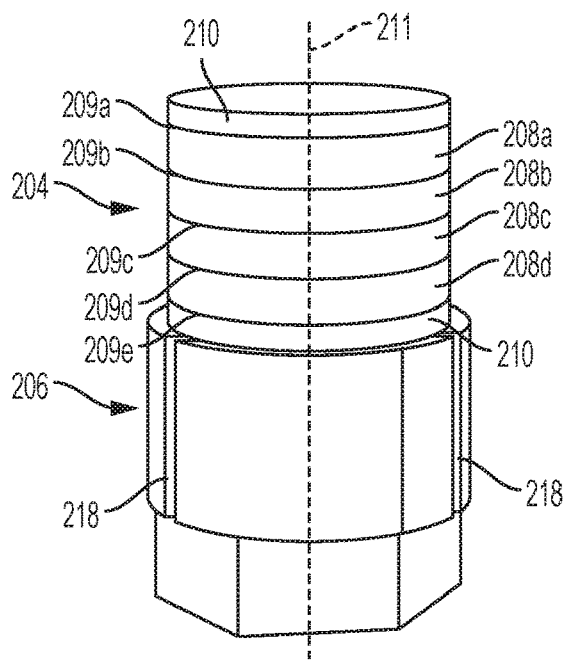
FIG. 6 is a perspective view of an ultrasonic transducer component of the ultrasonic transducer assembly shown in FIG. 5.
Figure 7:
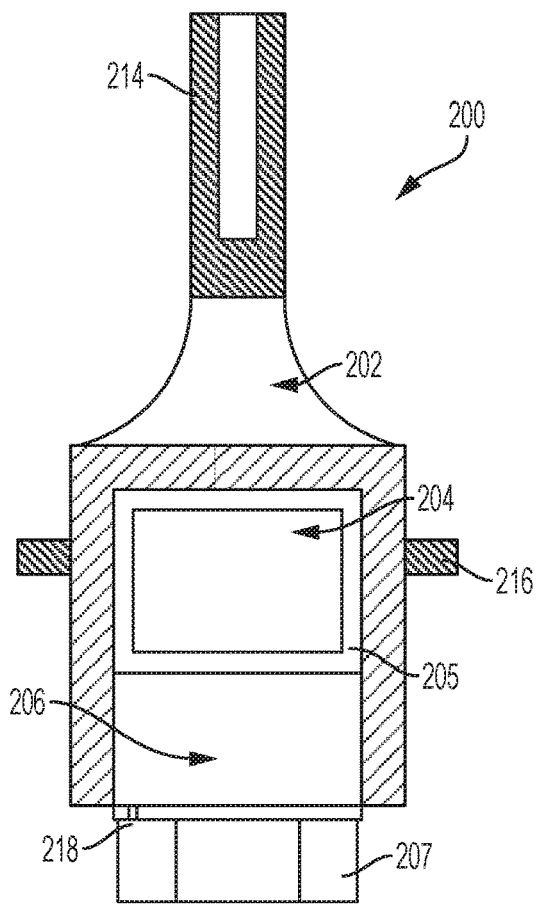
FIG. 7 is a partial sectional view of the transducer assembly shown in FIG. 5 showing an opening defined by a housing portion of the transducer assembly.

FIGS. 5-8 illustrate one aspect of a transducer assembly 200 comprising a housing 202 and an ultrasonic transducer 204, where the ultrasonic transducer 204 comprises a plurality of piezoelectric elements 208a, 208b, 208c, 208d arranged in a stack configuration, which may be referred to as a "Langevin stack", and having a longitudinal axis 211 along the centerline of the piezoelectric elements 208a-208d, and an end mass 206 positioned along the longitudinal axis 211 adjacent a first end of the ultrasonic transducer 204. In one aspect, the stack of piezoelectric elements 208a-208d comprises four solid disks as shown in FIGS. 5-7 made of a lead zirconate titanate (PZT) material contained in a compression housing. In other aspects, the ultrasonic transducer 204 piezoelectric stack may comprise an even multiple (n×2) of piezoelectric elements 208a-208d. The piezoelectric stack may be assembled wet (glue bonded) directly onto the threaded end mass 206 and equipped with electrically conducive elements such as wires or cables, for example, to connect the piezoelectric stack to an active energy source and ground at the generator 102 (FIGS. 1-3). Accordingly, the end mass 206 and ultrasonic transducer 204 may be separate components that are then bonded together to allow for assembly of the transducer assembly 200.

The piezoelectric elements 208a-208d are electrically connected in parallel and are paired in opposite directions. A first electrode 209b is disposed between adjacent piezoelectric elements 208a-208b, a second electrode 209c is disposed between adjacent piezoelectric elements 208b-208c, and a third electrode 209d is disposed between adjacent piezoelectric elements 208c-208d. A fourth electrode 209a is disposed and at the proximal end of the piezoelectric element 208a and a fifth electrode 209e is disposed at the end of the piezoelectric element 208d. In one configuration, the electrodes 209a-209e are formed of an electrically conductive material in thin disk configuration. The electrodes 209a-209e are configured to electrically couple to the generator 102 (shown in FIGS. 1-3) to energize the piezoelectric elements 208a-208d. In one configuration, the electrodes 209a, 209c, 209e are configured to electrically couple to the negative polarity or return (−) of the generator 102 output port and the electrodes 209b, 209d are configured to couple to the positive polarity (+) of the generator 102 output port. In operation, the generator 102 applies an alternating voltage potential to the electrodes 209a-209e to energize the piezoelectric elements 208a-208d and cause them to mechanically expand and contract in the longitudinal direction in response to the alternating voltage potential. When the alternating voltage potential is in a frequency range of approximately 30-100 kHz the alternating voltage potential causes the piezoelectric elements 208a-208d to vibrate at ultrasonic frequencies. One suitable frequency value of the alternating voltage potential may be 55.5 kHz, for example.

Furthermore, the ultrasonic transducer 204 comprises compression elements 210 located at the ends of the piezoelectric elements 208a and 208d. In accordance with the present disclosure, the compression elements 210 provide the points of contact between the end mass 206 and the ultrasonic transducer 204 at the first end of the transducer 204 and between the housing 202 and the ultrasonic transducer 204 at a second end of the ultrasonic transducer 204. The compression element 210 may comprise a metal compression plate or spacer that has a size and form factor that corresponds to the piezoelectric elements 208a-208d. The compression element 210 may help to avoid damage to the stack of piezoelectric elements 208a-d as the end mass 206 is threaded into and engaged with the housing 202. Compression may prevent the individual piezoelectric elements 208a-208d from being subjected to tension, which may cause mechanical failure. The compression elements 210 may each be manufactured from a type of material that is appropriate for application in the ultrasonic transducer 204, including metals for example, such as aluminum, stainless steel, titanium, and/or alloys thereof, or other materials, such as carbon fiber, fiberglass, plastics, etc.

As shown in the example illustrated in FIGS. 5-7, the housing 202 comprises a horn shaped portion 220. The horn shaped portion 220 defines an open proximal end for receiving the ultrasonic transducer 204 and a wall that surrounds and houses the ultrasonic transducer 204 when it is inserted into an opening 213 defined by the horn shaped portion 220 of the housing 202. The horn shaped portion 220 may include internal threads on the inner wall surface allowing for the end mass 206 to be torqued into place. The horn shaped portion 220 also serves the function of amplifying the displacement of the ultrasonic transducer 204, and the horn shaped portion 220 compresses the piezoelectric elements 208a-208d of the ultrasonic transducer 204. According to various aspects, the diameter of the ultrasonic transducer 204 may be smaller that the inner diameter of the horn shaped portion 220 of the housing 202. Accordingly, a gap 205 is defined between the ultrasonic transducer 204 and the interior of the horn shaped portion 220 of the housing 202. This gap 205 allows for insertion of the ultrasonic transducer 204 and prevents the piezoelectric elements 208a-208d from coming into unwanted contact with a side wall of the interior surface of the horn shaped portion 220 of the housing 202.

The housing 202 also comprises a flange 216. The flange 216 is shown as an annular ring around the perimeter of the horn shaped portion 220. However, in some aspects, the flange 216 may instead be positioned in sections located about the perimeter instead of being arranged as a continuous ring. In other aspects, there may be additional flanges similar to and in addition to the flange 216 located at predetermined locations on the housing 202. Further, the flange 216 may be located at other locations along the housing 202, for example, the flange 216 may be located along the housing 202 closer to a distal end of the housing 202. According to various aspects, the flange 216 may include an O-ring or other elastomeric material member (not shown) that may provide sealing as well as damping of vibrations within the flange 216 and the housing 202 overall. An O-ring may be mounted within a groove or other feature (not shown) of the flange 216. Also, according to various aspects, the flange 216 may be replaced with a mass having radial dimensions similar to those of the stack 204 and the mass 206. A hand piece housing, or other frame member, of a surgical instrument may include corresponding shapes for receiving the flange 216.

The horn shaped portion 220 of the housing 202 allows for easy assembly of the transducer assembly 200 and provides advantages in heat dissipation and potential sealing of the ultrasonic transducer 204 and the stack of piezoelectric elements 208a-208d. In another aspect, the horn shaped portion 220 may be threaded on an outside surface that matches the threads on the end mass 206. Thus, the end mass 206 may be fit over the horn shaped portion 220 while compressing the ultrasonic transducer 204 when within the horn shaped portion 220 of the housing 202. In addition, the housing 202 may comprise a channel 222 for attaching a waveguide section or other instrument section 214. The channel 222 may be threaded or may include a quick connect and/or a locking feature for attachment of other components thereto. In various aspects, the housing 202 and the end mass 206 each may be made as a unitary piece or in sections. Further, the housing 202 and the end mass 206 each may be made from a type of metal that is appropriate for the application of the transducer assembly, for example, such as aluminum, stainless steel, titanium, and/or alloys thereof. In other aspects, the housing 202 may be made from other materials, such as carbon fiber, fiberglass, plastic, etc. as appropriate.

The end mass 206 may be coupled to the ultrasonic transducer 204 and the end mass 206 may be fixedly or removably attached with the housing 202. In one aspect, the ultrasonic transducer 204 is coupled to the end mass 206 via a suitable bonding mechanism. The ultrasonic transducer 204 and the end mass 206 may be bonded together via an adhesive, a weld, or other suitable bonding mechanism. In the aspect shown in FIGS. 5-7, the end mass 206 is configured to compress the plurality of piezoelectric elements 208a-208d when the end mass 206 is engaged with the housing 202. The end mass 206 is configured to engage with the housing 202 via a threaded connection. When the end mass 206 is engaged with the housing 202, a second end of the ultrasonic transducer 204 is compressed against an interior surface of the housing 202. The end mass 206 also comprises one or more longitudinal channels 218 to allow for wiring to be connected to the ultrasonic transducer 204. In addition, the end mass 206 may comprise a torqueing feature 207 that allows torque to be applied to the end mass 206. In FIGS. 5-7, the torqueing feature 207 is a hex head. In other aspects, the torqueing feature 207 may be any type of drive that allows for torqueing the end mass 206; for example, the torqueing feature 207 may be any type of screw drive.

The piezoelectric elements 208a-208d may be fabricated from any suitable material, such as, for example, lead zirconate-titanate (PZT), lead meta-niobate, lead titanate, barium titanate or other piezoelectric ceramic material. As shown in FIGS. 5-7, each of the piezoelectric elements 208a-d have a circular or disk shaped configuration and are formed as a solid element with an uninterrupted surface. In other aspects, the piezoelectric elements 208a-208d may have different shapes and/or different surface characteristics, such as apertures for bolting a plurality of elements together. The elements 208a-208d may have an appropriate aspect factor for a particular application. Additionally, the piezoelectric elements 208a-208d may be energized via positive electrodes 209b, 209d and negative electrodes 209a, 209c, 209e respectively positioned between the piezoelectric elements 208a-208d and at the ends of the piezoelectric elements 208a and 208e as shown in FIGS. 5-6. The positive and negative electrodes 209a-209e may be electrically coupled to wires that may be encased within a cable and electrically connectable to an ultrasonic signal generator 102 of an ultrasonic system as described above. The electrodes 209a-209e may be the same as or similar to electrodes 324, 326, and 328 described below in connection with FIGS. 9 and 10. In addition, according to various aspects, the piezoelectric elements 208a-208d may comprise a borehole through each of the elements 208a-208d that allows for assembly of other features of the ultrasonic transducer 204.

Each of positive electrodes 209b, 209d, negative electrodes 209a, 209c, 209e, and the piezoelectric elements 208a-208d that make up the ultrasonic transducer 204 each may be a solid element with an uninterrupted surface. Alternatively, the transducer 204 defines a bore extending therethrough. For example, in one aspect, the bore extends through the center of the piezoelectric elements 208a-208d. The ultrasonic transducer 204 of the transducer assembly 200 is configured to convert an electrical signal from an ultrasonic generator, such as generator 102 described above in connection with FIGS. 1-3, into mechanical energy that results in primarily a standing acoustic wave of longitudinal vibratory motion of the ultrasonic transducer 204 and an end effector (not shown in FIGS. 1-8) at ultrasonic frequencies. In another aspect, the vibratory motion of the ultrasonic transducer 204 may act in a different direction. For example, the vibratory motion may comprise a local longitudinal component of a more complicated motion of the tip of the ultrasonic instrument. When the transducer assembly 200 is energized, a vibratory motion standing wave may be generated through the transducer assembly 200. The transducer assembly 200 may be designed to operate at a resonance such that an acoustic standing wave pattern of a predetermined amplitude is produced. The amplitude of the vibratory motion at any point along the transducer assembly 200 may depend upon the location along the transducer assembly 200 at which the vibratory motion is measured. A minimum or zero crossing in the vibratory motion standing wave is generally referred to as a node (e.g., where motion is usually minimal), and a local absolute value maximum or peak in the standing wave is generally referred to as an anti-node (e.g., where motion is usually maximal). According to aspects, the distance between an anti-node and its nearest node may be one-quarter wavelength ($\lambda/4$).

Furthermore, the plurality of piezoelectric elements 208a-208d and electrodes 209a-209e may be bonded via an adhesive, such as with an epoxy or other glue, a weld, or other suitable bonding mechanism. In one aspect, surfaces of a piezoelectric element may have an adhesive, such as epoxy, placed on it and subsequently an electrode 209a-209e may be placed over the adhesive. The adhesive may be provided in a layer such that it does not interfere with the electrical connections between the electrodes 209a-209e and the piezoelectric elements 208a-208d themselves. Further, according to aspects, only some of the piezoelectric elements 208a-208d may be bonded together, instead of the entire plurality of piezoelectric elements 208a-208d. In addition, the plurality of piezoelectric elements 208a-208d may be assembled dry, with no adhesive or bonding mechanism between each of the layers.

Figure 8:
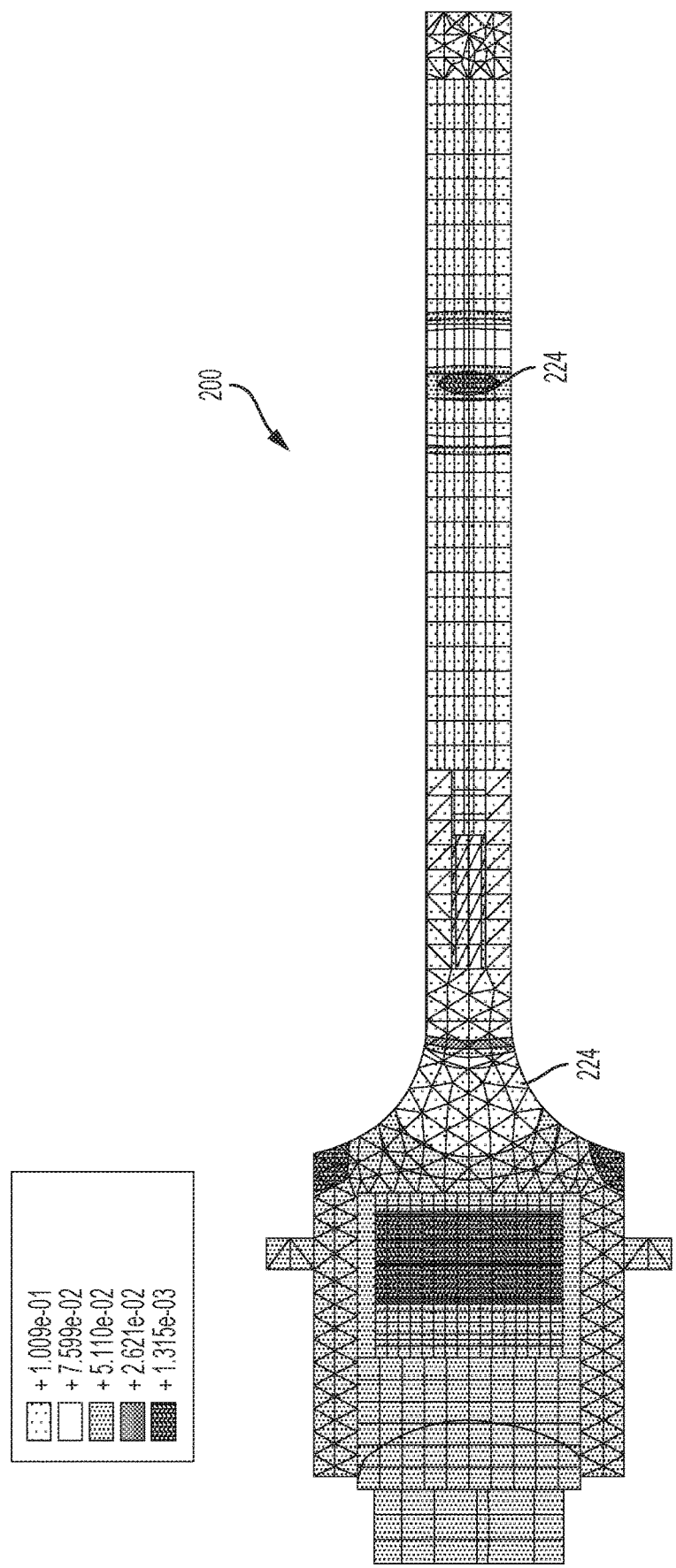
FIG. 8 is a finite element analysis mesh of the stresses on the transducer assembly shown in FIG. 5.

Additionally, FIG. 8 is a finite element analysis mesh contour plot of the stresses at nodes 224 of the transducer assembly 200 that is configured as a half wave resonator at 40 kHz, for example. According to aspects, the design of the transducer assembly 200 can be scaled up or down in frequency and wavelength based on the appropriate application. For example, the transducer assembly 200 may be made to function as a quarter or full wavelength transducer.

Figure 9:
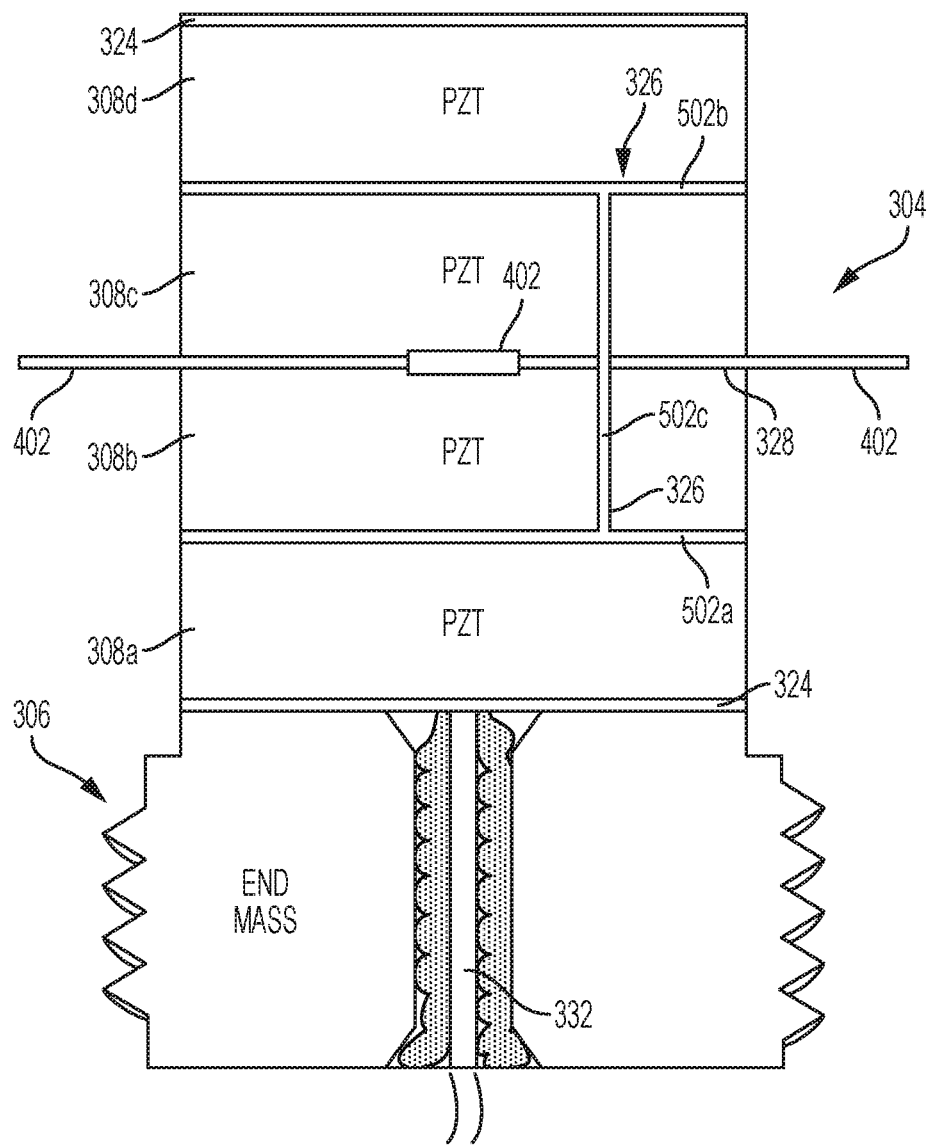
FIG. 9 is a front view of an aspect of a combination end mass and ultrasonic transducer of the present disclosure.
Figure 10:
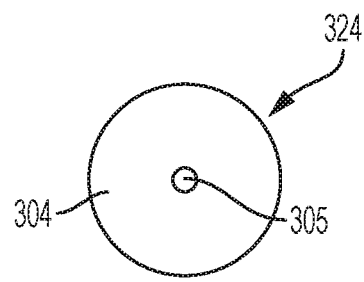
FIG. 10 is a top view of an aspect of a first electrode of the present disclosure.
Figure 11:
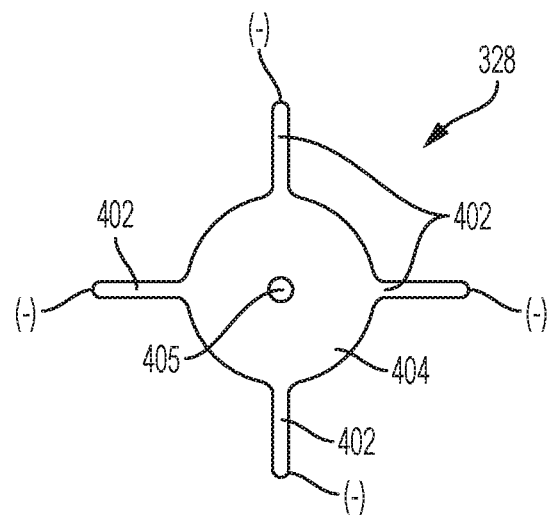
FIG. 11 is a top view of an aspect of a second electrode of the present disclosure.
Figure 12:
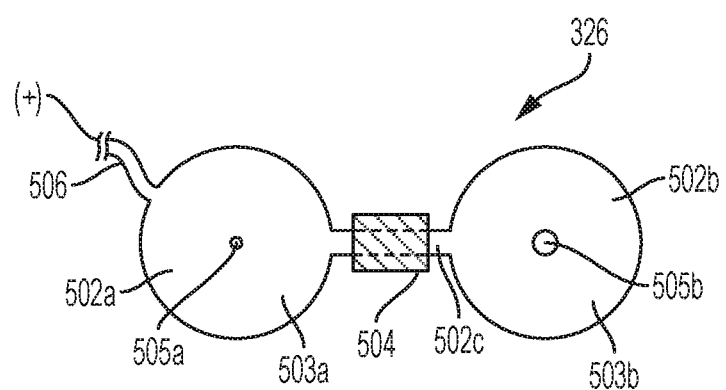
FIG. 12 is a top view of an aspect of a third electrode of the present disclosure.

FIG. 9 shows a combination of an end mass 306 and ultrasonic transducer 304 that may be sized and configured to be located within a housing of an ultrasonic surgical instrument, such as housing 302 also described below. Any aspects of the end mass 306, ultrasonic transducer 304, and housing 302, may have the same or similar attributes as end mass 206, ultrasonic transducer 204, and housing 202, respectively, as appropriate. Electrodes 324, 326, and 328, described in more detail in FIGS. 10-12, are shown in adjacent relationship to the piezoelectric elements 308a-308d that make up the ultrasonic transducer 304. As shown in FIG. 9, the end mass 306 has a channel 332 defined therethrough. The channel 332 may be used for the wiring or cabling that is connected to one or more of the electrodes 324, 326, and 328 to allow for energization of the electrodes 324, 326, and 328 and application of electricity to the piezoelectric elements 308a-308d. The channel 332 may further have sealing product, such as solder, epoxy, glue, rubber, or other insulation material, located therein to prevent the entry of foreign substances into the end mass 306 and ultrasonic transducer 304. Furthermore, the channel 332 may be sized and configured to match a size and shape of the wiring or cabling for the electrodes 324, 326, and 328 such that a sealing product is not necessary. Also, as shown in FIG. 9, the end mass 306 may include threads on an exterior surface of the end mass for engagement with a housing 302 of an ultrasonic transducer assembly and/or other component of a surgical instrument as described herein.

Electrodes 324, 326, and 328 energize the piezoelectric elements 308a-308d according to a drive signal received from a generator 102 based on a predetermined wavelength and frequency of an ultrasonic wave in order for a surgical instrument to apply ultrasonic energy to a target. Electrodes 324, 326, and 328 may have a shape that conforms to the shape of a piezoelectric element 308a-308d to allow for maximum surface area contact between a respective electrode 324, 326, and 328 and piezoelectric elements 308a-308d. Electrodes 324, 326, and 328 are located at the proximal end of the ultrasonic transducer 304, closest to the end mass 306, and the distal end of the ultrasonic transducer 304, respectively. Electrodes 324, 326, and 328 may be made from a conductive material, such as metal, for example, copper, that functions to provide an electrical current to the piezoelectric elements 308a-308d.

As shown in FIG. 10, electrode 324 has a disk shape center 304 with an aperture 305 through the center. As shown in FIGS. 9 and 11, electrode 328 comprises a disk shape center 404 with an aperture 405 and a plurality of arms 402 that extend outward from the center 404. The arms 402 may be sized and configured to contact the inside walls of a conductive housing of a transducer assembly, such as housing 202 described above, to provide an electrical ground for the ultrasonic transducer 304. Accordingly, the arms 402 may be configured to provide a path to ground or return to the generator 102. In addition, the arms 402 provide an alignment feature for the transducer 304 as the transducer 304 is placed into the housing 202. Further, electrodes 324 may provide an electrical ground based on contact with the electrode 324 and the housing 202 and the end mass 306, respectively. As shown in FIG. 12, electrode 326 comprises two contacts or pads 502a-502b, each with a center 503a-503b with an aperture 505a-505b, where the contacts 502a-502b are electrically connected together. The contacts 502a-502b are connected via an electrically conductive connection element 502c. A wire or cable 506 is connected to one of the contacts 502a-502b for energization of the contacts 502a-502b. The cable 506 may be coupled to the positive polarity (+) of the generator 102 output port. An apron 504 is included for insulating the electrode 326 for electrically isolating electrode 326 and preventing potential energization of other electrodes along with a housing of a surgical instrument.

Referring back to FIG. 9, when electrode 326 is energized, electrical current may flow through the two piezoelectric elements 308a-308d in the middle of the ultrasonic transducer stack 304 and follow a path to ground, resulting in the energization of the piezoelectric element 308a-308d at the proximal end of the ultrasonic transducer 304, closest to the end mass 306, and the piezoelectric element 308a-308d at the distal end of the ultrasonic transducer 304, respectively. The electrical current passing through the piezoelectric elements 308a-308d causes the piezoelectric elements 308a-308d to expand and contract, which generates an ultrasonic wave.

Figure 13:
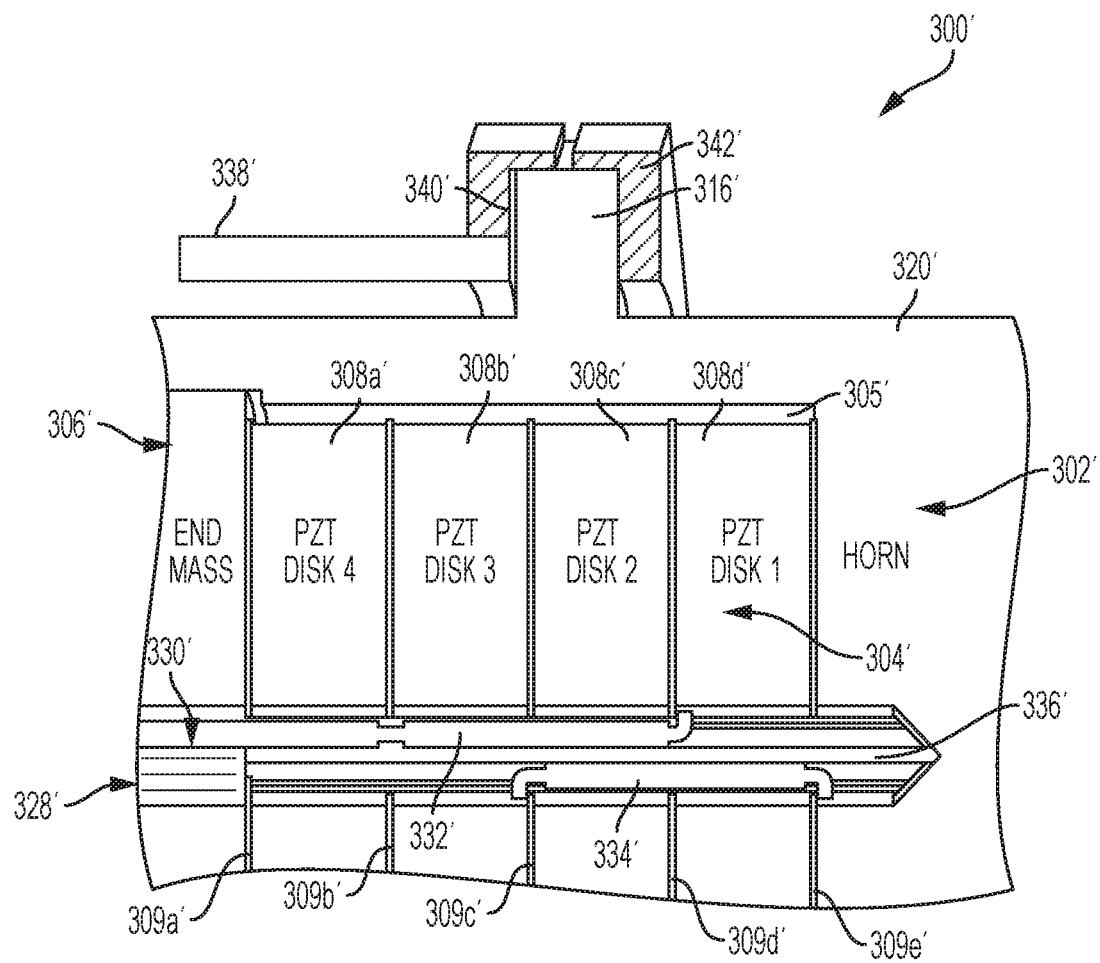
FIG. 13 is a cross sectional view of another aspect of a transducer assembly of the present disclosure.

FIG. 13 displays a cross sectional view of transducer assembly 300' that comprises a housing 302', ultrasonic transducer 304', and end mass 306'. Similar to transducer assembly 200, the end mass 306' compresses the ultrasonic transducer 304' within the horn shaped portion 320' of the housing 302'. Accordingly, the end mass 306' may engage the horn shaped portion 320' of the housing 302' based on a threaded connection. Further, the housing 302' comprises flange 316'. The flange 316' provides a location for attachment of a surgical instrument component 342' such as, for example, a surgical instrument housing that surrounds the transducer assembly 300', where a surgical instrument comprises the transducer assembly 300'. In addition, the instrument component 342' may comprise an isolator that is intended to dampen or isolate the vibrations from the transducer assembly 300'. In one aspect, the isolator comprises an elastomer.

Aspects of the piezoelectric elements 308a'-308d' are the same or similar to the piezoelectric elements 208a-208d of transducer assembly 200 described with regard to FIGS. 5-8 above, as appropriate. Accordingly, the piezoelectric elements 308a'-308d' may be electrically connected in parallel and are paired in opposite directions. A first electrode 309b' is disposed between adjacent piezoelectric elements 308a'-308b', a second electrode 309c' is disposed between adjacent piezoelectric elements 308b'-308c', and a third electrode 309d' is disposed between adjacent piezoelectric elements 308c'-308d'. A fourth electrode 309a' is disposed at the proximal end of the piezoelectric element 308a' and a fifth electrode 309e' is disposed at the end of the piezoelectric element 308d. In one configuration, the electrodes 309a-309e' are formed of an electrically conductive material in thin disk configuration. The electrodes 309a'-309e' are configured to electrically couple to the generator 102 (shown in FIGS. 1-3) to energize the piezoelectric elements 308a'-308d'. In one configuration, the electrodes 309a', 309c', 309e' are configured to electrically couple to the negative polarity or return (−) of the generator 102 output port and the electrodes 309b', 309d' are configured to couple to the positive polarity (+) of the generator 102 output port. In operation, the generator 102 applies an alternating voltage potential to the electrodes 309a'-309e' to energize the piezoelectric elements 308a'-308d' and cause them to mechanically expand and contract in the longitudinal direction in response to the alternating voltage potential. When the alternating voltage potential is in a frequency range of approximately 30-100 kHz, the alternating voltage potential causes the piezoelectric elements 308a'-308d' to vibrate at ultrasonic frequencies. In one example, operational frequency of the alternating voltage potential is approximately 55.5 kHz. In one aspect, each of the electrodes 308a'-308d' is a flat electrode.

In addition, according to the aspect shown in FIG. 13, the piezoelectric elements 308a'-d' and electrodes 309a'-e' comprise a borehole 328' therethrough that allows for insertion of an alignment feature 336' through the borehole 328'. The alignment feature 336' is configured so that the ultrasonic transducer 304', and accordingly the piezoelectric elements 308a'-d' and electrodes 309a'-e', may be held in place within the horn shaped portion 320' of the housing 302'. A gap 305' is maintained to prevent the ultrasonic transducer 304' from shorting out against the housing 302'.

Additionally, the alignment feature 336' comprises a post 336' that provides structural support and allows for an energization of the appropriate electrodes 309a'-309e'. In one aspect, the post 336' comprises a lumen that is used for centering the transducer stack 304' during the torqueing of the end mass 306' to the horn shaped portion 320' of the housing 302'. The lumen may have channels to allow wires connected to the electrodes 309a'-309e' to be inserted in the center of the lumen. The lumen may be removed after torqueing of the end mass 306' to the horn shaped portion 320' is complete. This may improve alignment of the piezoelectric elements 308a'-308b' and allow for very low impedance (e.g. 12 ohms) electrodes/wiring to be used.

As shown in FIG. 13, a source or "hot" lead 332' and a return or "cold" lead 334' are connected to the post 336'. The source lead 332' is coupled to a generator, such as generator 102 described above, and to electrodes 309b', 309d'. The return lead 332' is coupled to a ground connection of or otherwise provides a return path to the generator, and is also coupled to electrodes 309c' and 309e'. In aspects of the present disclosure, the source lead 332' and/or the return lead 334' may comprise a wire that is located within the post 336'. Additionally, the post 336' may be made of a conductive material and may provide a return path for the electrodes 309a', 309c', and 309e'. As shown in FIG. 13, the post 336' of the alignment feature 330' may extend into an indent or aperture in the housing 302', which may allow the post 336' to be held in a secure engagement with the housing 302'. In one aspect, the alignment feature 330' may be formed integrally with the end mass 306' and the end mass 306' may be a solid object without an aperture therethrough. In another aspect, the alignment feature 330' may be a separate component that fits through an aperture, such as borehole 328', through the end mass 306'. In this aspect, a wire may extend through the borehole 328' of the end mass 306'. The borehole 328' and any openings between the end mass 306' and the housing 302' may be covered with a sealing product, such as solder, epoxy, glue, rubber, tape, or other insulation material, located therein to prevent the entry of foreign substances into the interior of the transducer assembly 300'. In addition, the alignment feature 330' may comprise threads such that the ultrasonic transducer 304' or the individual piezoelectric elements 308a'-d' and electrodes 309a'-e' can be threadedly engaged with the alignment feature 330'. In another aspect, the alignment feature 330' may rely on a compression fit between one of the ultrasonic transducer 304' or the individual piezoelectric elements 308a'-d' and the electrodes 309a'-e'.

Also as shown in FIG. 13, a return electrode 340' is connected to the flange 316' and the electrode 340' is connected to a ground lead 338' (i.e. a ground wire) that provides a path to ground or return to the generator 102. The return electrode 340' may have an outer diameter that is shaped to match the geometry of flange 316' and may have an inner diameter that provides sufficient clearance to allow the return electrode 340' to slip over an outer diameter of the horn shaped portion 320' of the housing 302'. In one aspect, inside the horn shaped portion 320', where the ultrasonic transducer stack 304' resides, a return path may be established through the horn shaped portion 320' to one or more of the piezoelectric elements 308a'-d' and through the end mass 306' to one or more of the piezoelectric elements 308a'-d'.

Figure 14:
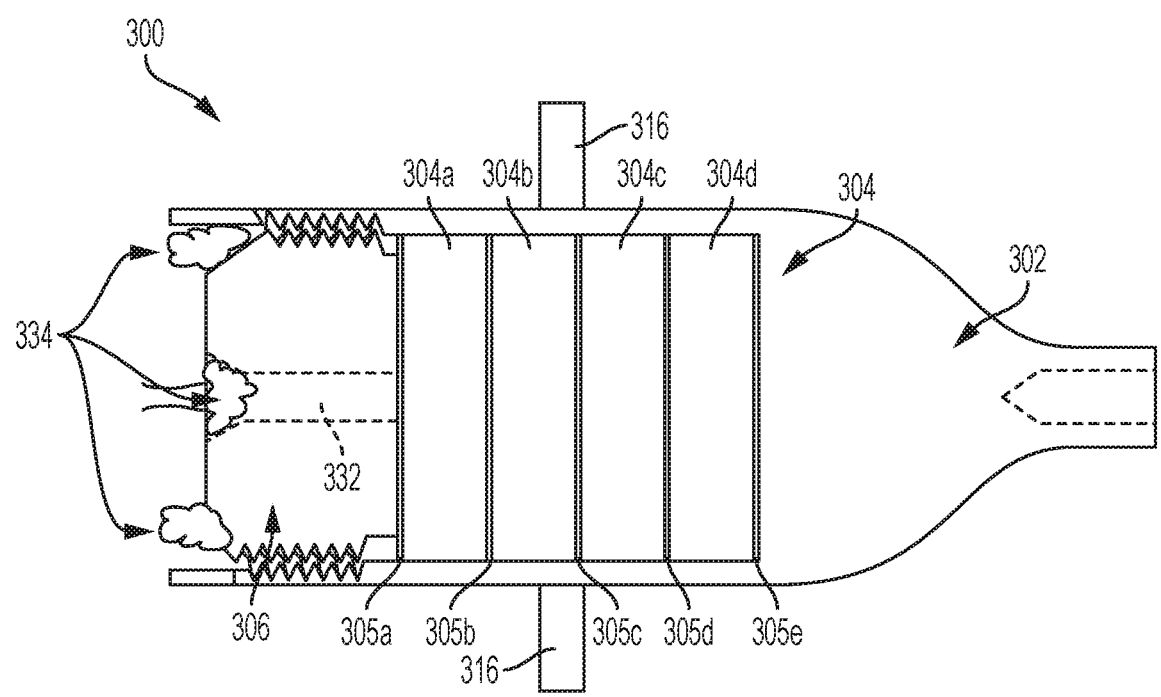
FIG. 14 is a cross sectional view of an aspect of a transducer assembly of the present disclosure.
Figure 15:
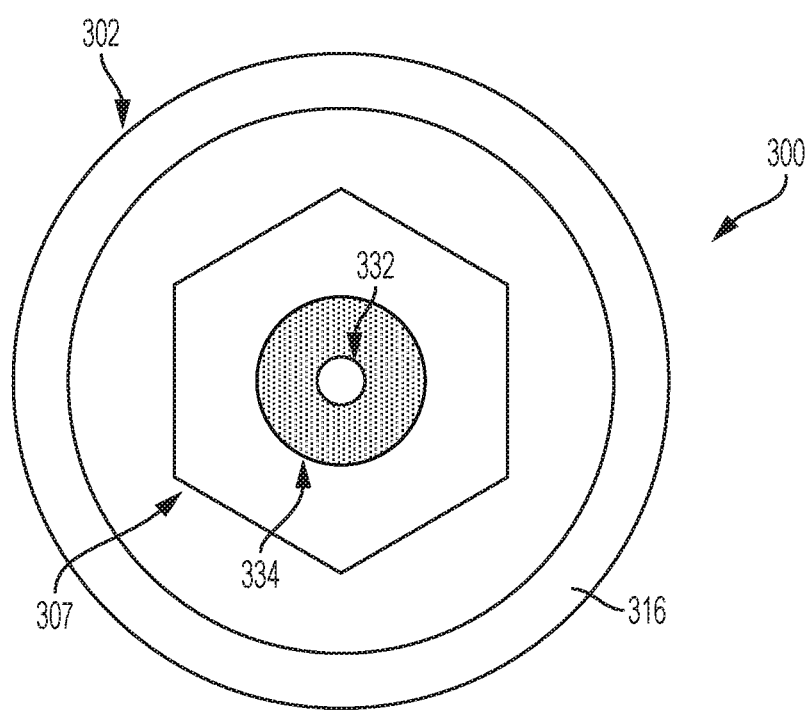
FIG. 15 is a top view of the transducer assembly shown in FIG. 14.

FIGS. 14 and 15 display an aspect of an ultrasonic transducer assembly 300 that includes an end mass 306, ultrasonic transducer stack 304, and housing 302. The housing 302 comprises a flange 316. Similar to flange 216, flange 316 may be annular around an exterior surface of the housing 302 or it may include components at separate locations along the exterior surface of the housing 302. Aspects of the ultrasonic transducer stack 304 may be the same or similar to the ultrasonic transducer 204 described above, as appropriate. The ultrasonic transducer stack 304 comprises a plurality of piezoelectric elements in a stack configuration with a plurality of electrodes located in between to energize the piezoelectric elements. Furthermore, any aspects of the housing 302 may be the same or similar to the housing 202 described above, as appropriate.

As shown in FIG. 14, the end mass 306 has a channel 332 therethrough. The channel 332 may be used for the wiring or cabling that is connected to one or more of the electrodes of the transducer stack 304 to allow for energization of the electrodes 305a-305e and application of electricity to the piezoelectric elements 304a-304d. Aspects of the electrodes 305a-305e and piezoelectric elements 304a-304d are the same or similar to the piezoelectric elements 208a-208d and electrodes 209a-209e of transducer assembly 200 described with regard to FIGS. 5-8 above, as appropriate. The channel 332 may further have sealing product 334, such as solder, epoxy, glue, rubber, tape, or other insulation material, located within the channel or only at a proximal end, furthest from the transducer stack 304, to prevent the entry of foreign substances into the end mass 306 and ultrasonic transducer 304. Furthermore, while the end mass 306 may be threaded into the housing 302, sealing product 334 is also located at a proximal end of the end mass 306 adjacent the location that the end mass 306 engages the housing 302, such that the interior of the housing 302, along with the transducer 304 and portion of the end mass 306 located within the housing 302, is sealed and the end mass 306 is bonded to the housing 302. In one aspect, the seal to the interior of the housing may be a hermetic seal. Further, in one aspect, any sections where the end mass 306 engages the housing 302, along with the channel 332, may be welded so that a seal is formed.

Figure 16:
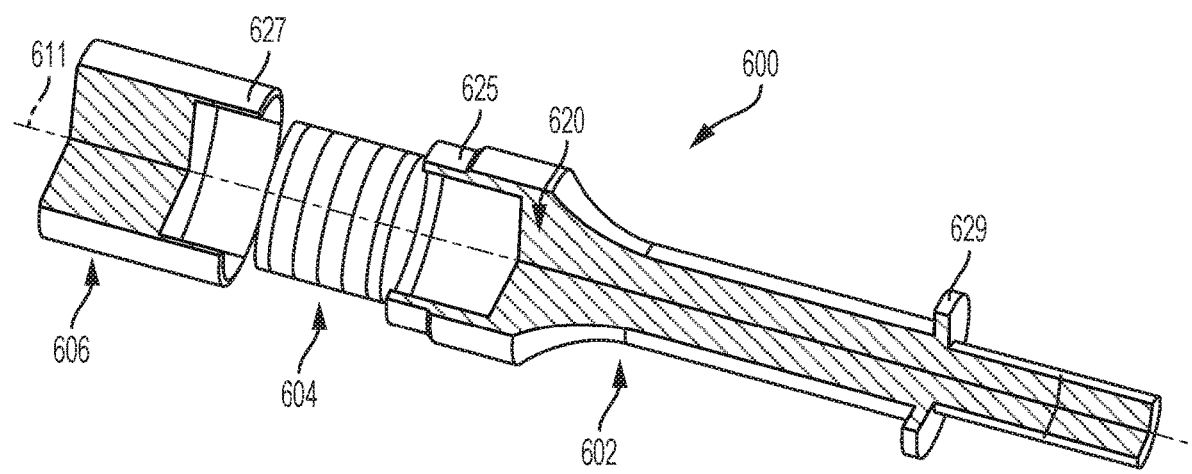
FIG. 16 is an exploded view of an aspect of a transducer assembly of the present disclosure.

FIG. 16 displays a transducer assembly 600 similar to those discussed above. The transducer assembly 600 comprises a housing 602, an ultrasonic transducer stack 604, and an end mass 606. Any aspects of the housing 602, transducer stack 604, and end mass 606 may have the same or similar attributes as any housing, ultrasonic transducer stack, and end mass described above, respectively, as appropriate. The transducer 604 and end mass 606 may be positioned along a longitudinal axis 611. The distal end of the end mass 606 comprises a cap portion 627 that is configured to fit over a proximal rim 625 at the proximal end of the horn shaped portion 620 of the housing 602. The cap portion 627 of the end mass 606 and the horn shaped portion 620 of the housing 602 act to house the transducer 604 and the cap portion 627 is designed to overlap with the proximal rim 625 of the housing 602. In one aspect, there is a gap between the end mass 606 and the housing 602 that provides a gap that may be filled with aluminum wire for a laser welding process. The thickness of the proximal rim 625 may be such that it is thinner than an adjacent portion of the housing 602. Furthermore, the thickness of the proximal rim 625 may be such that when the distal end of the end mass 606 is placed over the proximal rim 625, the circumference of the housing 602 and end mass 606 is uniform along the transducer assembly 600. In one aspect, the transducer assembly 600 comprises a distal rim 629, similar to the proximal rim 625. Additionally, the cap portion 627 of the end mass 606 may be a length such that transducer 604 is held at a predetermined amount of compression when the end mass 606 is engaged with the housing 602. The transducer 604 may be held in compression by a fixed engagement or a bond at the distal end of the end mass 606 and the proximal end of the housing 602. The bond may be accomplished by an appropriate bonding means, such as an adhesive, a strap, a weld, such as a laser weld, around the circumference of the transducer assembly 600 and a hermetic seal may be formed. By bonding the end mass 606 and the housing 602, the ultrasonic transducer 604 may be held in compression and remain under that compression even after the transducer assembly 600 is activated a large number of times.

Figure 17:
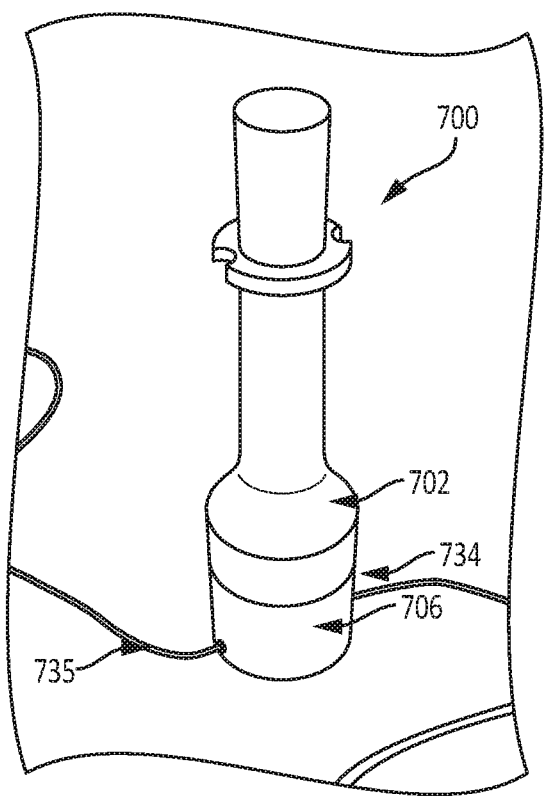
FIG. 17 is a photograph of a transducer assembly of the present disclosure.
Figure 18:
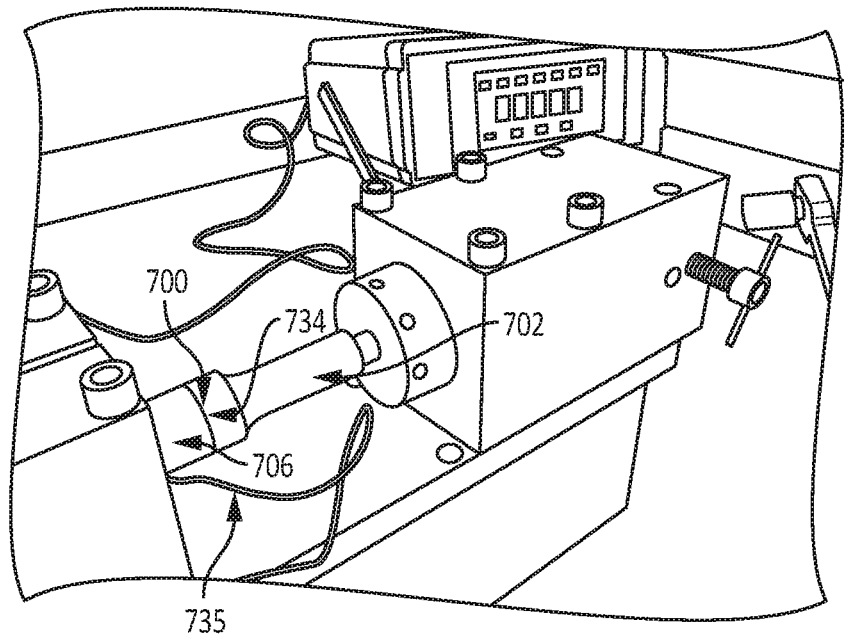
FIG. 18 is a photograph of the transducer assembly shown in FIG. 17.

FIGS. 17 and 18 display photographs of a transducer assembly 700 similar to transducer assembly 600. The transducer assembly 700 comprises a housing 702 and an end mass 706 that are made of aluminum and have been welded together via weld 734. A cable 735 is configured to pass through an opening of the end mass 706 to provide electricity to an ultrasonic transducer (not shown) or to provide a reading of the voltage given off by the piezoelectric elements of the transducer. The transducer assembly 700 may comprise an ultrasonic transducer, of which any aspects are the same or similar to ultrasonic transducers 204 and 304 described above, as appropriate.

Figure 19:
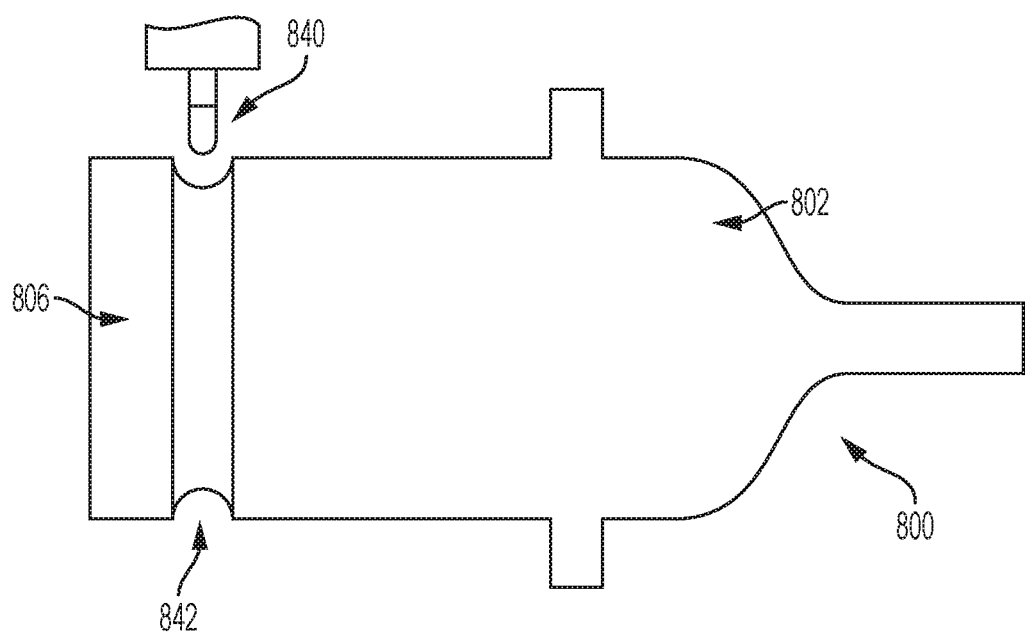
FIG. 19 is a front view of another transducer assembly of the present disclosure.

FIG. 19 displays a transducer assembly 800 that comprises a housing 802 and an end mass 806. An annular groove or channel 842 is located adjacent a proximal end of the transducer assembly 800 on an exterior surface of the transducer assembly 800. An electrical contact 840 is configured to make contact with the groove 842 and provide an electrical coupling between circuitry connected to the electrical contact 840 and the exterior surface of the transducer assembly 800. In one aspect, the electrical contact 840 comprises a pin, for example, such as a pogo pin. According to aspects, the transducer assembly 800 may be placed within a surgical instrument housing. The transducer assembly 800 may be rotatable within the surgical instrument housing based on the relative movement that is allowed between the electrical contact 840 and the transducer assembly 800 based on the electrical connection between the exterior surface of the transducer assembly 800 and the electrical contact 840. Any aspects of the housing 802 and end mass 806 may have the same or similar attributes as a housing and an end mass described above, respectively, as appropriate. Further, any aspects of the ultrasonic transducer that is located within the interior of transducer assembly 800, may be the same or similar to any ultrasonic transducers described above, as appropriate. Accordingly, the electrical contact 840 may provide a ground connection to a transducer stack where an electrode, for example electrode 328, contacts the housing 802 of the transducer assembly 800. In one aspect, the groove or channel 842 may be located at a point where the end mass 806 and the housing 802 are brought together. Therefore, the groove 842 may be formed based on a weld between the end mass 806 and the housing 802, where an electrically conductive material, such as aluminum, is used for the weld. Further, the groove 842 may be formed in an exterior surface of either the end mass 806 or the housing 802.

Figure 20:
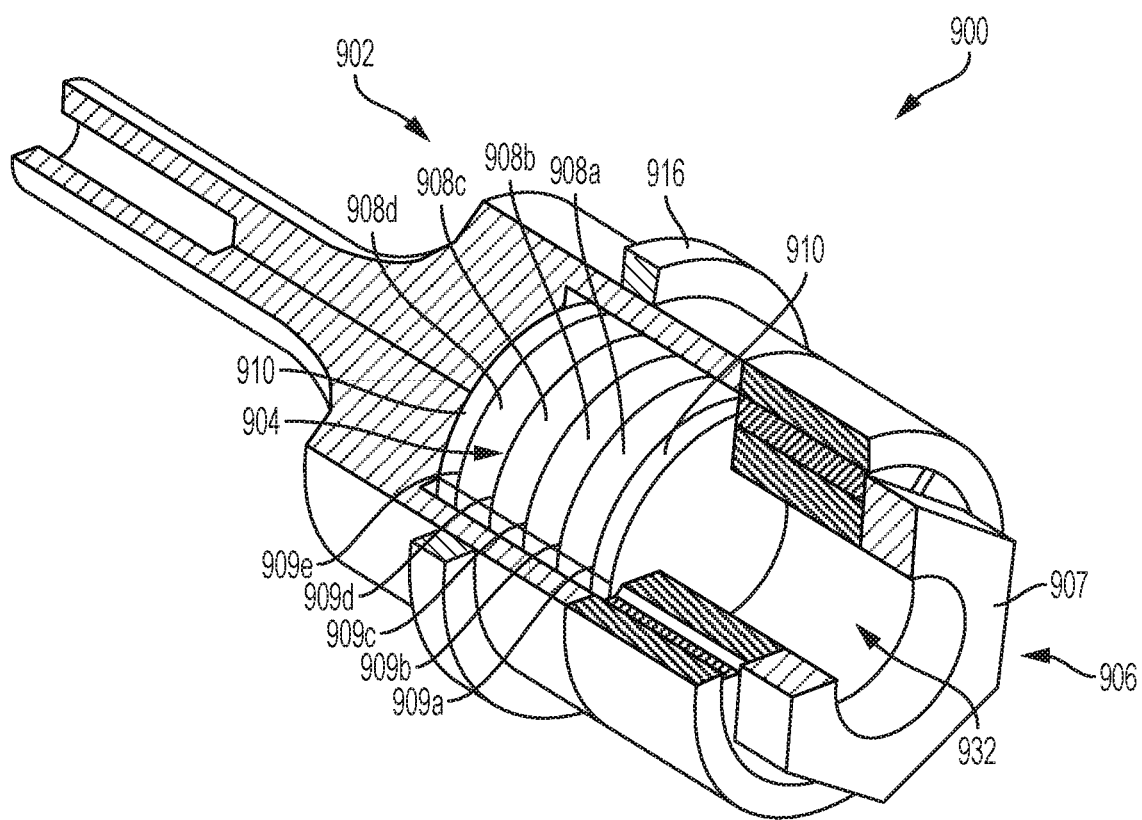
FIG. 20 is a perspective view of another transducer assembly of the present disclosure.

FIG. 20 is a top view of the transducer assembly 900 that comprises a housing 902, an ultrasonic transducer stack 904, and an end mass 906. Any aspects of the housing 902, transducer stack 604, and end mass 906 may have the same or similar attributes as any housing, ultrasonic transducer stack, and end mass described above, respectively, as appropriate. The housing 902 also comprises a flange 916. Similar to flange 216 described above, flange 916 may be annular around an exterior surface of the housing 902 or it may include components at separate locations along the exterior surface of the housing 902. Similar to ultrasonic transducer 204 described above, the stack of piezoelectric elements 908a-90d consists of four solid disks as shown in FIG. 20 and compression elements 910 are located at either end of the stack of piezoelectric elements 908a-90d. The compression element 910 may comprise a metal compression plate or spacer that has a size and form factor that corresponds to the piezoelectric elements 908a-90d. The compression element 910 may help to avoid damage to the stack of piezoelectric elements 908a-90d as the end mass 906 is threaded into and engaged with the housing 902. The piezoelectric elements 908a-908d are electrically connected in parallel and are paired in opposite directions. A first electrode 909b is disposed between adjacent piezoelectric elements 908a-908b, a second electrode 909c is disposed between adjacent piezoelectric elements 908b-908c, and a third electrode 909d is disposed between adjacent piezoelectric elements 908c-908d. A fourth electrode 909a is disposed and at the proximal end of the piezoelectric element 908a and a fifth electrode 909e is disposed at the end of the piezoelectric element 908d.

Figure 21:
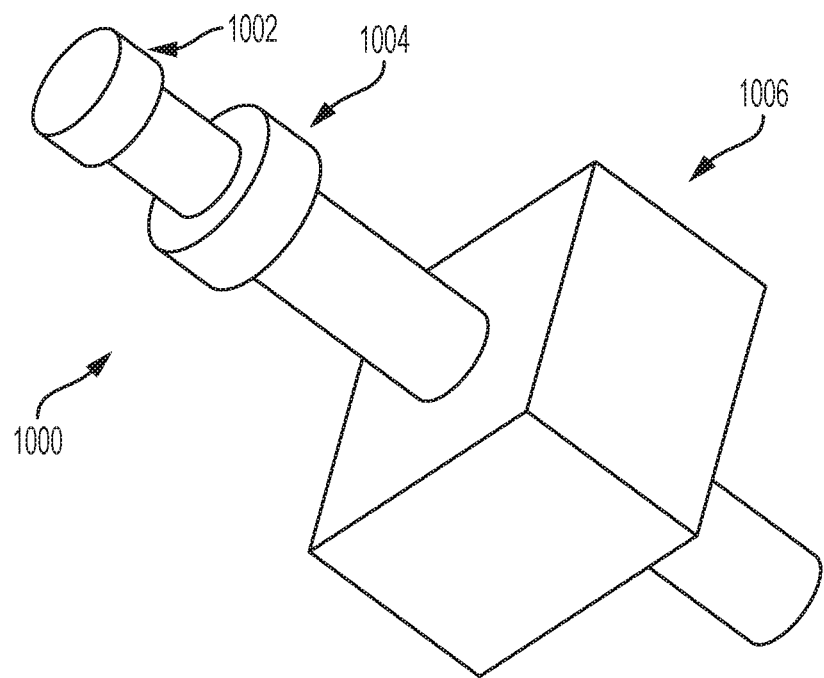
FIG. 21 is a perspective view of a piston device of the present disclosure.
Figure 22:
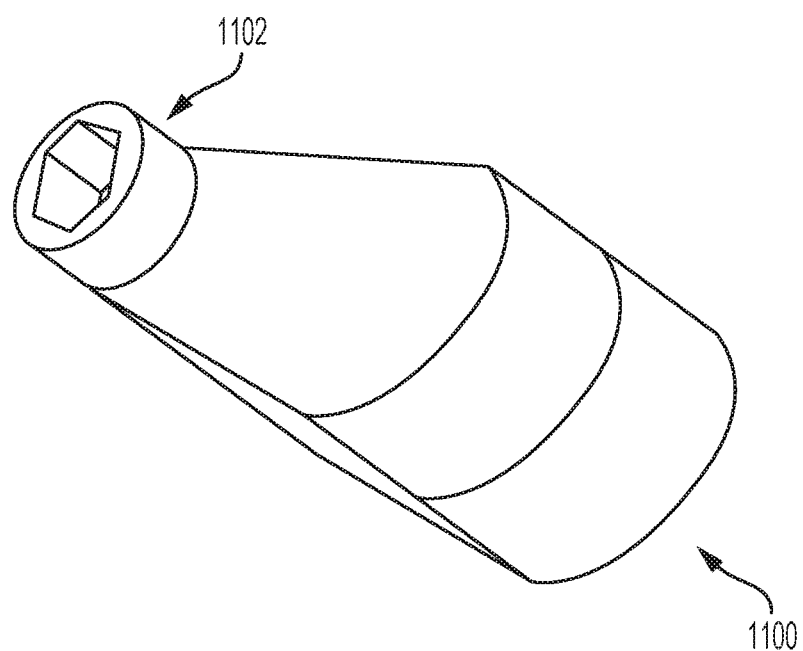
FIG. 22 is a perspective view of a socket head device of the present disclosure.

Further, the end mass 906 comprises torqueing feature 907 (e.g. hex head 907) and an aperture 932 defined through the end mass 906. Additionally, the piston device 1000 shown in FIG. 21 and socket device 1100 shown in FIG. 22 may allow for pre-compression of the ultrasonic transducer 904 and torqued engagement of the end mass 906 with the housing 902. The piston device 1000 feeds through the hollow socket head 1102 of the socket device 1100. The hollow socket head 1102 contacts the hex head 907 on the end mass 906 and torques the end mass 906. Aperture 932 allows for the insertion of the piston head 1002 of piston device 1000. Piston device 1000 also comprises a load cell 1004 and actuator 1006. The actuator 1006 may be a linear actuator or a hydraulic actuator. The piston head 1002 is configured to apply a force against the ultrasonic transducer 904 within the housing 902. The piston head 1002 pushes against spacer 910, which is a non-piezoelectric component, to prevent localized stress on the piezoelectric elements 908a-90d. When the piston head 1002 applies sufficient pressure against the transducer stack 904, force is lower at the point of contact between the end mass 906 and the transducer stack 904. With a lower force between the end mass 906 and the transducer 904, there is less friction and therefore less torque applied to the transducer 904. As the end mass 906 is torqued into place within the housing 902, the force on the piston head 1002 can be monitored. As the force on the piston head 1002 is reduced (e.g. caused by load sharing via the end mass 906), an operator may be signaled that the transducer 904 is at the correct pressure and the assembly step is finished.

Figure 23:
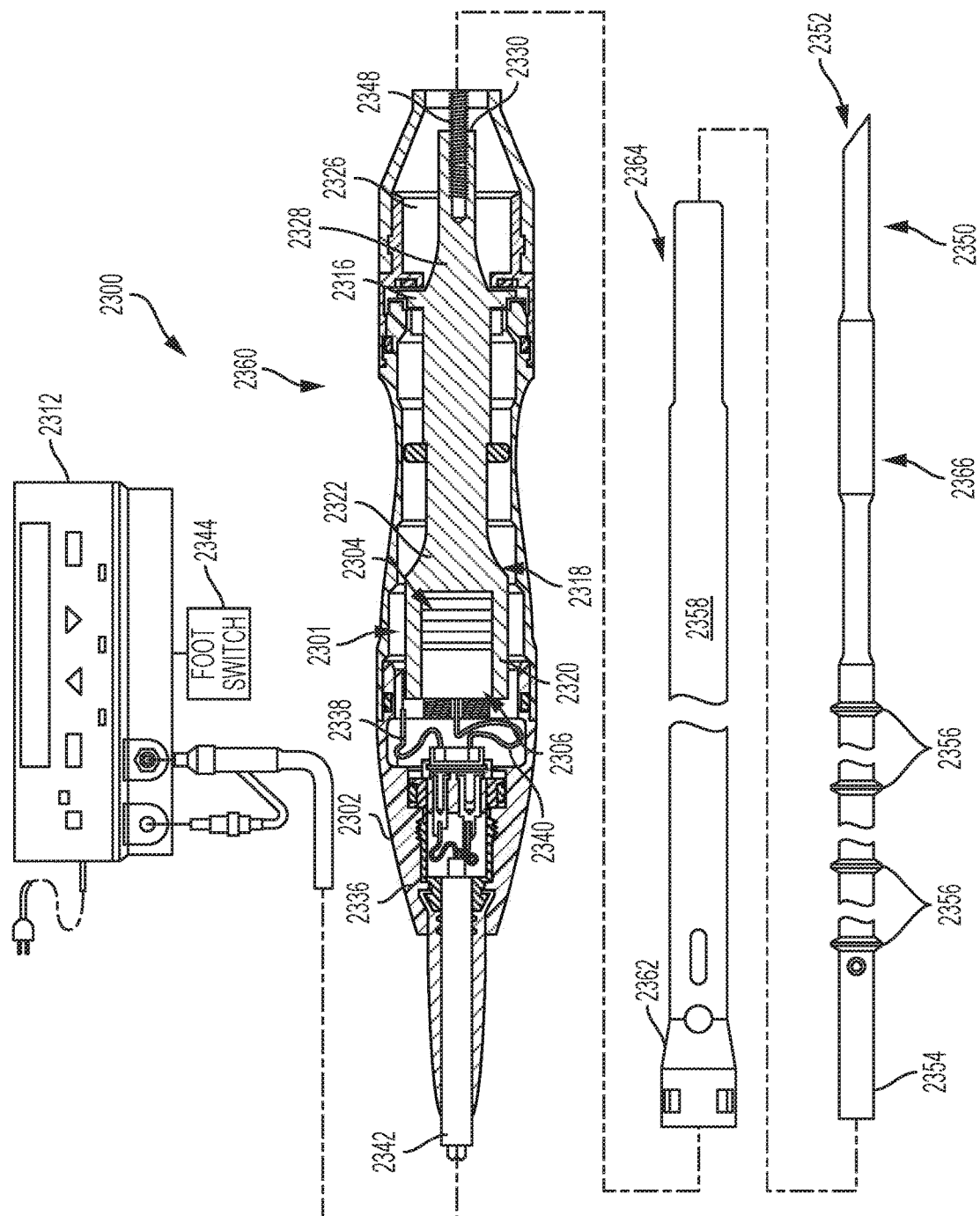
FIG. 23 is a diagram of one aspect of a surgical system including an ultrasonic surgical instrument.

FIG. 23 illustrates one aspect of an ultrasonic system 2300. The ultrasonic system 2300 may comprise an ultrasonic signal generator 2312 coupled to an ultrasonic transducer assembly 2301 of a surgical instrument, referred to as a hand piece assembly 2360. The hand piece assembly 2360 comprises a hand piece housing 2336, and an ultrasonically actuatable single element end effector or ultrasonically actuatable blade 2352. A housing 2302 of the ultrasonic transducer assembly 2301 generally includes a transduction portion 2318, a first resonator portion or end-bell 2320, and a second resonator portion or fore-bell 2322, and ancillary components, such as flange 2316. The total construction of these portions comprises a resonator. The ultrasonic transducer assembly 2301 is preferably an integral number of one-half system wavelengths (n*λ/2: wherein "n" is any positive integer; e.g., n=1, 2, 3 . . . ) in length. Further, the ultrasonic transducer assembly 2301 comprises the ultrasonic transducer 2304, end mass 2306, and housing 2302, where the housing 2302 comprises a nose cone 2326, a velocity transformer 2328, and a surface 2330. Aspects of the ultrasonic transducer assembly 2301 may be the same or similar as those described above with regard to transducer assemblies 200, 300, 600, 700, 800, and 900, including the components thereto, as appropriate.

Further, the terms "proximal" and "distal" are used with reference to a clinician gripping the hand piece assembly 2360. Thus, the end effector 2350 is distal with respect to the more proximal hand piece assembly 2360. It will be further appreciated that, for convenience and clarity, spatial terms such as "top" and "bottom" also are used herein with respect to the clinician gripping the hand piece assembly 2360. However, surgical instruments are used in many orientations and positions, and these terms are not intended to be limiting and absolute.

The distal end of the end-bell 2320 is connected to the proximal end of the transduction portion 2318, and the proximal end of the fore-bell 2322 is connected to the distal end of the transduction portion 2318. The fore-bell 2322 and the end-bell 2320 have a length determined by a number of variables, including the thickness of the transduction portion 2318, the density and modulus of elasticity of the material used to manufacture the end-bell 2320 and the fore-bell 2322, and the resonant frequency of the ultrasonic transducer assembly 2301. The fore-bell 2322 may be tapered inwardly from its proximal end to its distal end to amplify the ultrasonic vibration amplitude as the velocity transformer 2328, or alternately may have no amplification. A suitable vibrational frequency range may be about 20 Hz to 120 kHz. A well-suited vibrational frequency range may be about 30-100 kHz. One example operational vibrational frequency may be approximately 55.5 kHz.

The ultrasonic transducer comprises an ultrasonic transducer stack 2304, aspects of which are the same or similar to any other ultrasonic transducer stack described herein. Positive and negative electrodes of the transducer stack 2304 are electrically coupled to wires 2338 and 2340, respectively. The wires 2338 and 2340 are encased within a cable 2342 and electrically connectable to the ultrasonic signal generator 2312 of the ultrasonic system 2300. The ultrasonic transducer 2304 of the transducer assembly 2301 converts the electrical signal from the ultrasonic signal generator 2312 into mechanical energy that results in primarily a standing acoustic wave of longitudinal vibratory motion of the ultrasonic transducer 2304 and the end effector 2350 at ultrasonic frequencies. In another aspect, the vibratory motion of the ultrasonic transducer may act in a different direction. For example, the vibratory motion may comprise a local longitudinal component of a more complicated motion of the tip of the ultrasonic system 2300. When the transducer assembly 2301 is energized, a vibratory motion standing wave is generated through the transducer assembly 2301. The ultrasonic system 2300 may be designed to operate at a resonance such that an acoustic standing wave pattern of a predetermined amplitude is produced. The amplitude of the vibratory motion at any point along the transducer assembly 2301 may depend upon the location along the transducer assembly 2301 at which the vibratory motion is measured. A minimum or zero crossing in the vibratory motion standing wave is generally referred to as a node (e.g., where motion is usually minimal), and a local absolute value maximum or peak in the standing wave is generally referred to as an anti-node (e.g., where motion is usually maximal). According to aspects, the distance between an anti-node and its nearest node may be one-quarter wavelength ($\lambda/4$).

The wires 2338 and 2340 transmit an electrical signal from the ultrasonic signal generator 2312 to the positive electrodes and the negative electrodes of the ultrasonic transducer stack 2304. The piezoelectric elements 2308 are energized by the electrical signal supplied from the ultrasonic signal generator 2312 in response to a switch 2344 to produce an acoustic standing wave in the transducer assembly 2301. The switch 2344 may be configured to be actuated by a clinician's foot. The electrical signal causes the piezoelectric elements 2308 to expand and contract in a continuous manner along the axis of the voltage gradient, producing longitudinal waves of ultrasonic energy. The straining of the elements causes large alternating compressional and tensile forces within the material. These forces in the piezoelectric elements 2308 manifest as repeated small displacements resulting in large alternating compression and tension forces within the material. The repeated small displacements cause the piezoelectric elements 2308 to expand and contract in a continuous manner along the axis of the voltage gradient, producing longitudinal waves of ultrasonic energy. The ultrasonic energy is transmitted through the transducer assembly 2301 to the end effector 2350 via a transmission component or ultrasonic transmission waveguide 2366.

According to various aspects, the waveguide 2366, end effector 2350 and blade 2352 may all be referred to generally as the end effector 2350.

In order for the transducer assembly 2301 to deliver energy to the end effector 2350, all components of the transducer assembly 2301 must be acoustically coupled to the end effector 2350. The distal end of the ultrasonic transducer 2304 may be acoustically coupled at the surface 2330 to the proximal end of the ultrasonic transmission waveguide 2366 by a threaded connection such as a stud 2348. The components of the transducer assembly 2301 are preferably acoustically tuned such that the length of any assembly is an integral number of one-half wavelengths ($n*\lambda/2$), where the wavelength $\lambda$ is the wavelength of a pre-selected or operating longitudinal vibration drive frequency $f_d$ of the transducer assembly 2301, and where n is any positive integer. It is also contemplated that the transducer assembly 2301 may incorporate any suitable arrangement of acoustic elements.

The ultrasonic end effector 2350 may have a length substantially equal to an integral multiple of one-half system wavelengths ($\lambda/2$). A distal end or blade 2352 of the ultrasonic end effector 2350 may be disposed near an antinode in order to provide the maximum longitudinal excursion of the distal end. When the transducer assembly is energized, the distal end 2352 of the ultrasonic end effector 2350 may be configured to move in the range of, for example, approximately 10 to 500 microns peak-to-peak, and preferably in the range of about 30 to 150 microns at a predetermined vibrational frequency.

The ultrasonic end effector 2350 may be coupled to the ultrasonic transmission waveguide 2366. The ultrasonic end effector 2350 and the ultrasonic transmission guide 2364 as illustrated are formed as a single unit construction from a material suitable for transmission of ultrasonic energy such as, for example, Ti6Al4V (an alloy of Titanium including Aluminum and Vanadium), Aluminum, Stainless Steel, or other suitable materials. Alternately, the ultrasonic end effector 2350 may be separable (and of differing composition) from the ultrasonic transmission waveguide 2366, and coupled by, for example, a stud, weld, glue, quick connect, or other suitable known methods. The ultrasonic transmission waveguide 2366 may have a length substantially equal to an integral number of one-half system wavelengths ($\lambda/2$), for example. The ultrasonic transmission waveguide 2366 may be preferably fabricated from a solid core shaft constructed out of material suitable to propagate ultrasonic energy efficiently, such as the titanium alloy discussed above, (e.g., Ti-6Al-4V) or any suitable aluminum alloy, or other alloys, for example.

The ultrasonic transmission waveguide 2366 comprises a longitudinally projecting attachment post 2354 at a proximal end to couple to the surface 2330 of the ultrasonic transmission waveguide 2366 by a threaded connection such as the stud 2348. In the aspect illustrated in FIG. 23, the ultrasonic transmission waveguide 2366 comprises a plurality of stabilizing silicone rings or compliant supports 2356 positioned at a plurality of nodes. The silicone rings 2356 dampen undesirable vibration and isolate the ultrasonic energy from an outer sheath 2358 for assuring the flow of ultrasonic energy in a longitudinal direction to the distal end 2352 of the end effector 2350 with maximum efficiency.

Also shown in FIG. 23, the outer sheath 2358 protects a user of the ultrasonic instrument 2360 and a patient from the ultrasonic vibrations of the ultrasonic transmission waveguide 2366. The sheath 2358 generally includes a hub 2362 and an elongated tubular member 2364. The tubular member 2364 is attached to the hub 2362 and has an opening extending longitudinally therethrough. The sheath 2358 may be threaded or snapped onto the distal end of the hand piece housing 2336. The ultrasonic transmission waveguide 2366 extends through the opening of the tubular member 2364 and the silicone rings 2356 isolate the ultrasonic transmission waveguide 2366 from the outer sheath 2358. The outer sheath 2358 may be attached to the waveguide 2366 with an isolator pin (not shown). The hole in the waveguide 2366 may occur nominally at a displacement. The waveguide 2366 may screw or snap onto the hand piece assembly 2360 by the stud 2348. The flat portions of the hub 2362 may allow the assembly to be torqued to a required level.

The hub 2362 of the sheath 2358 is preferably constructed from ULTEM®, and the tubular member 2364 is fabricated from stainless steel. Alternatively, the ultrasonic transmission waveguide 2366 may have polymeric material surrounding it to isolate it from outside contact. The distal end of the ultrasonic transmission waveguide 2366 may be coupled to the proximal end of the end effector 2350 by an internal threaded connection, preferably at or near an antinode. It is contemplated that the end effector 2350 may be attached to the ultrasonic transmission waveguide 2366 by any suitable means, such as a welded joint or the like. Although the end effector 2350 may be detachable from the ultrasonic transmission waveguide 2366, it is also contemplated that the end effector 2350 and the ultrasonic transmission waveguide 2366 may be formed as a single unitary piece.

Figure 24:
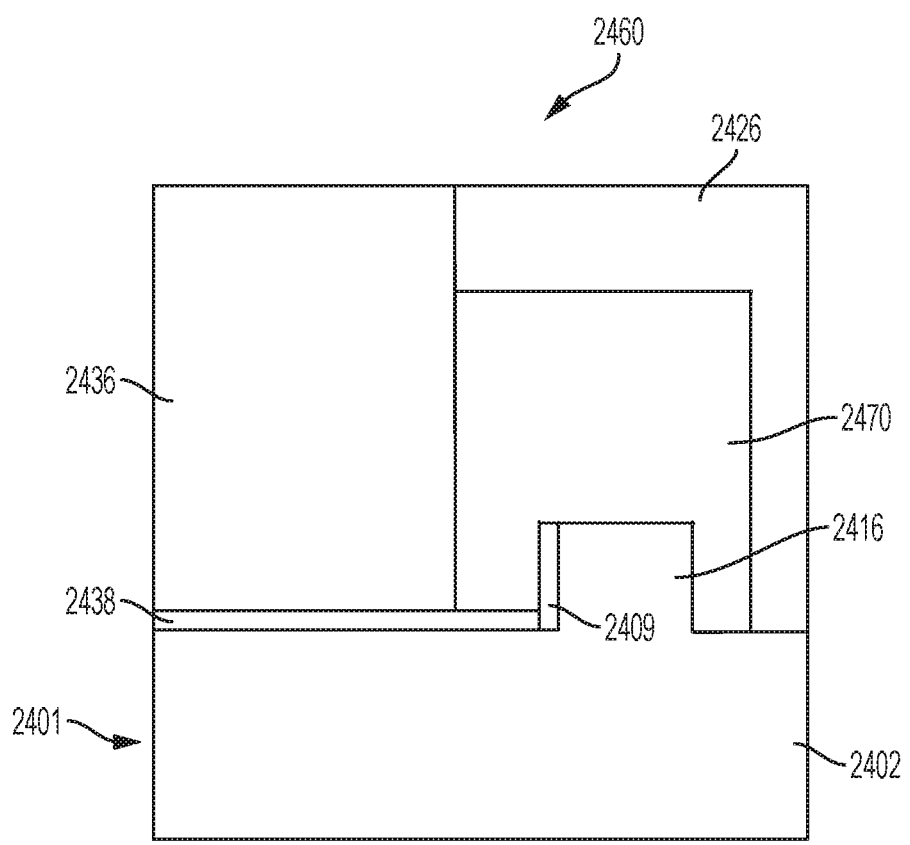
FIG. 24 is a cross section of an aspect of an ultrasonic surgical instrument.

FIG. 24 illustrates one aspect of a hand piece assembly 2460, aspects of which are the same or similar to hand piece assembly 2360, as appropriate. FIG. 24 shows a close in view of a portion of transducer assembly 2401, which includes housing 2402 and flange 2416, and a hand piece housing 2436 and nose cone 2426 of the hand piece assembly 2460. An electrode 2409 is located between the flange 2416 of the housing 2402 and an isolator 2470. The isolator 2470 is used to dampen or isolate the vibrations from the transducer assembly 2401 to the hand piece assembly 2460. In one aspect, the isolator 2470 comprises an elastomer.

The electrode 2409 is adjacent the flange 2416 and the electrode 2409 is connected to a ground lead 2438 that provide a path to ground or return to a generator that supplies power to the hand piece assembly 2460. The electrode 2409 may have an outer diameter that is shaped to match the geometry of flange 2416 and may have an inner diameter that provides sufficient clearance to allow the electrode 2409 to be placed over an outer surface the housing 2402. The electrical connection for the return path to the generator is intended to be through the outer surface of the transducer. In one aspect, the electrode 2409 is a flat electrode that is placed in contact with the flange 2416 and held in place by the isolator 2470.

Figure 25:
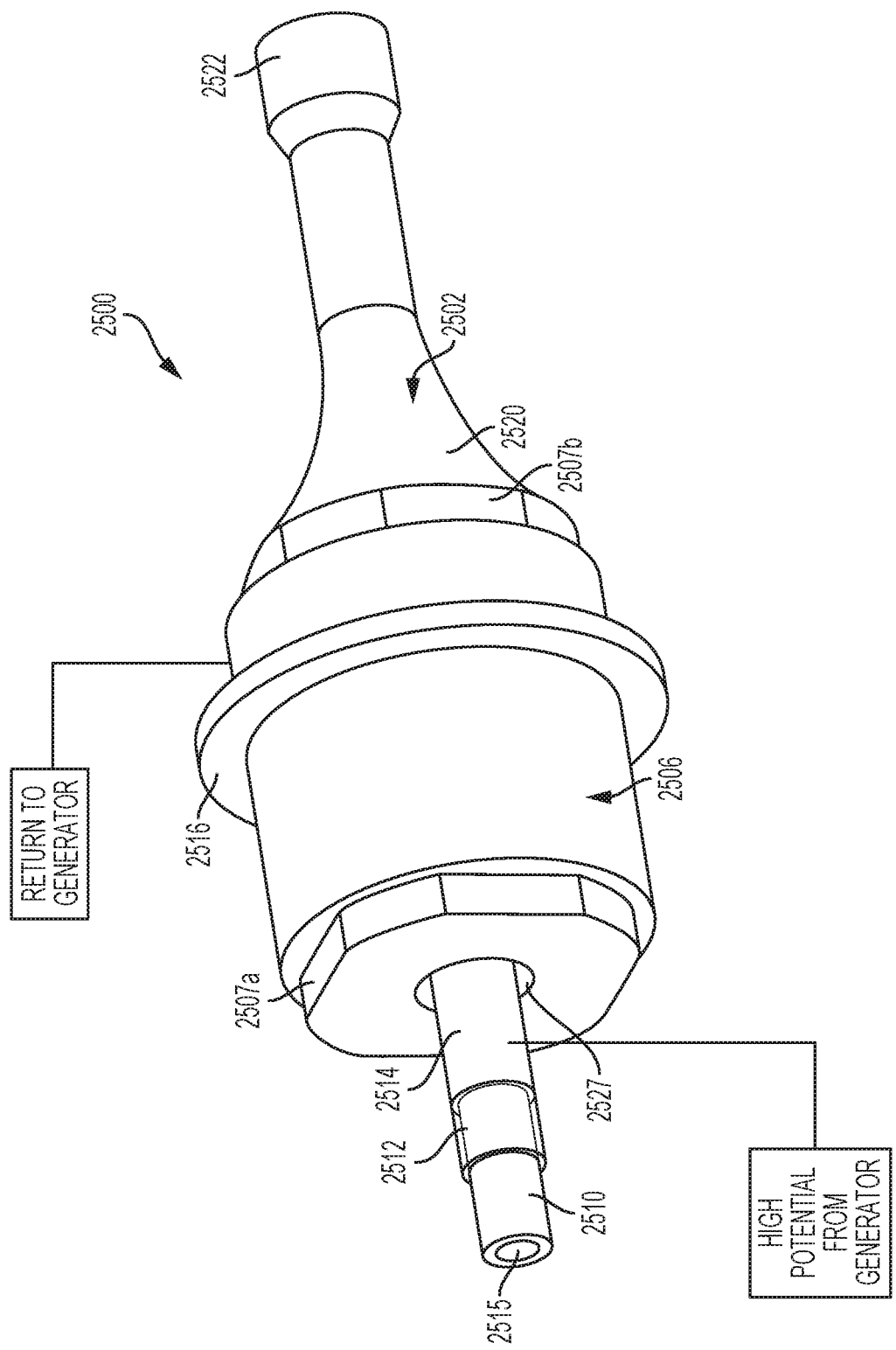
FIG. 25 is a perspective view of one aspect of an ultrasonic transducer assembly.
Figure 26:
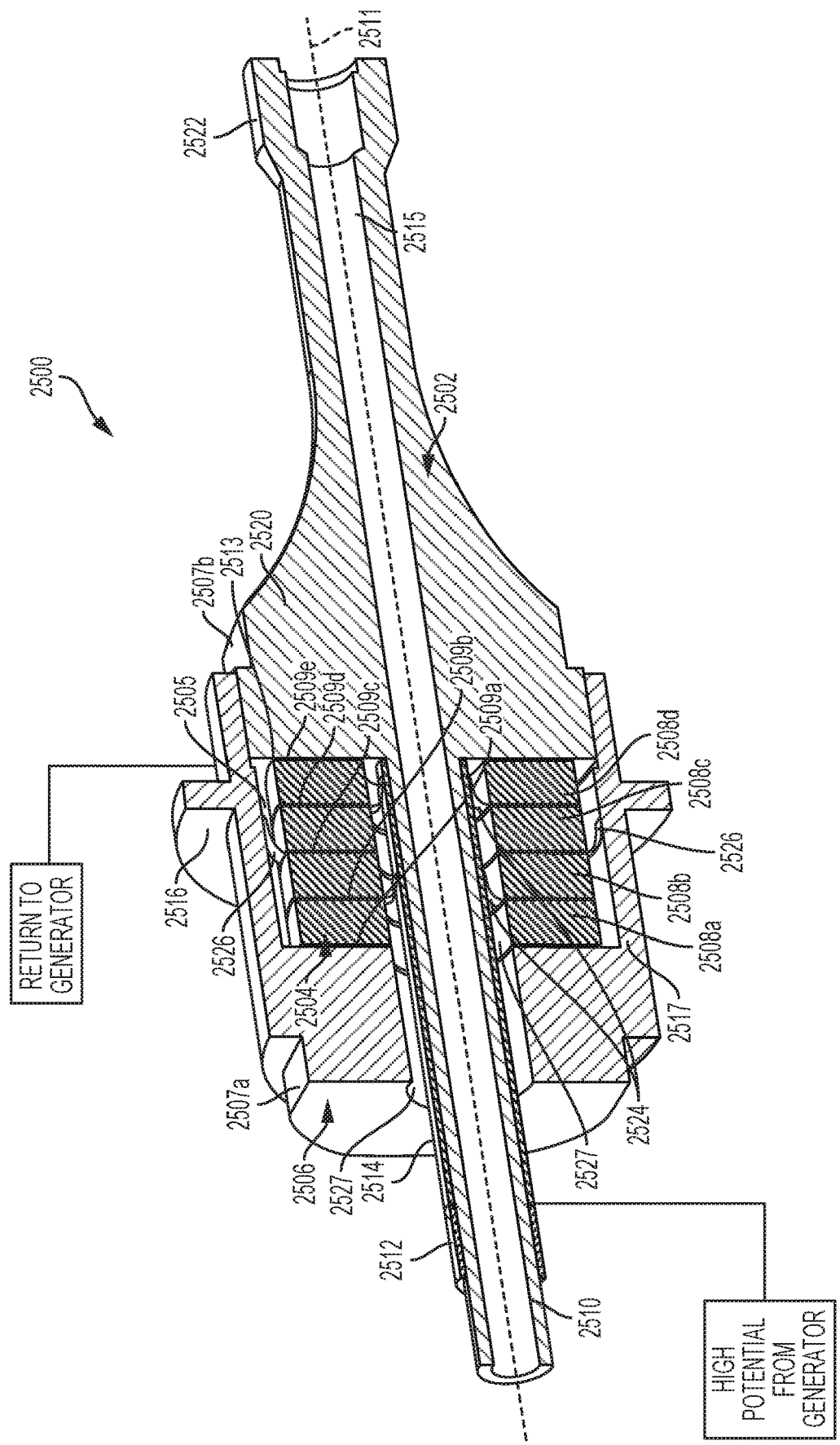
FIG. 26 is a cross section of the ultrasonic transducer assembly shown in FIG. 25.
Figure 27:
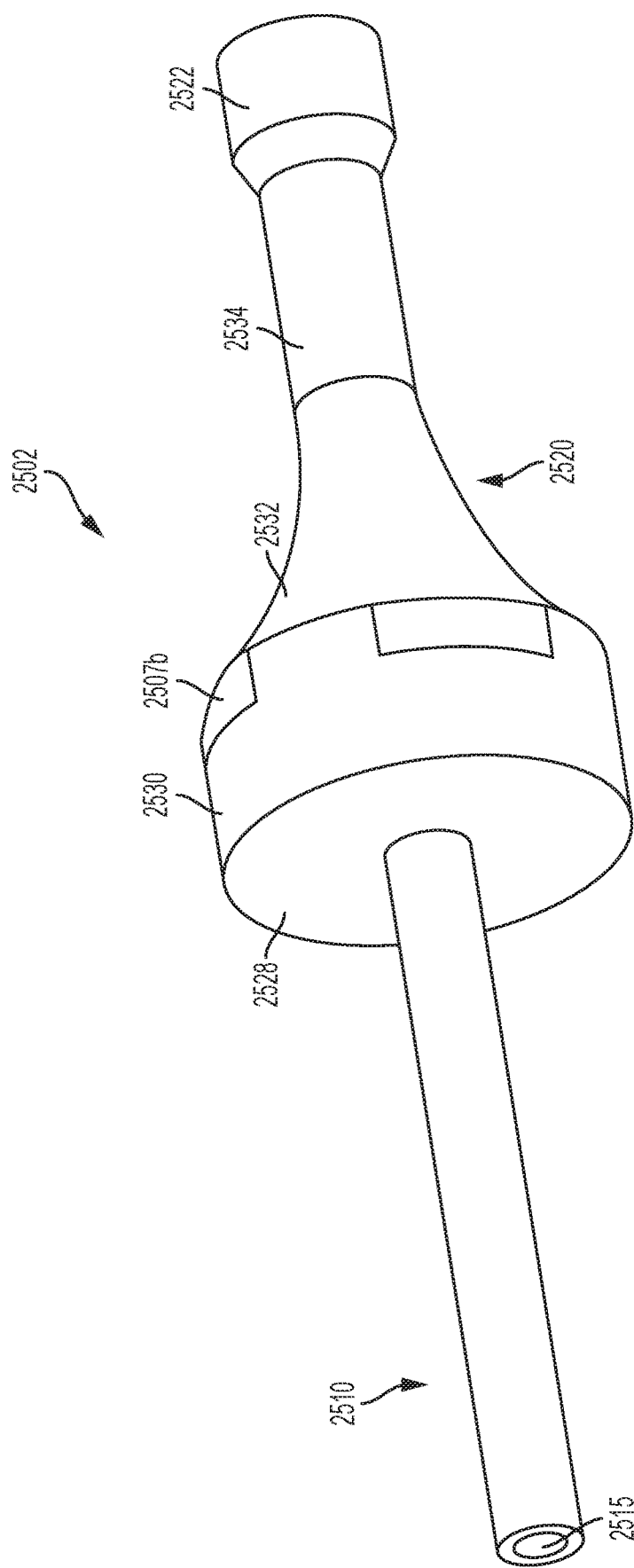
FIG. 27 is a perspective view of an aspect of a housing of the ultrasonic transducer assembly shown in FIG. 25.

FIGS. 25-26 illustrate one aspect of a transducer assembly 2500 and FIG. 27 is an illustration of the housing 2502 of transducer assembly 2500 shown in FIGS. 25-26. The transducer assembly comprises a housing 2502, an ultrasonic transducer 2504, and an end mass 2506. The housing 2502 comprises a conduit section 2510 and a base portion 2520, wherein a lumen or fluid passageway 2515 is defined through the conduit section 2510 and the base portion 2520. The base portion 2520 is shown in FIGS. 25-27 as having a horn shape, and may be referred to as a horn-shaped portion 2520. The transducer assembly 2500 may also include a conductive element 2514, insulator 2512, and the conduit section 2510 of the housing 2502. An inner isolator region may be present based on insulator 2512 that provides a nonconductive path between the conduit section 2510 of the housing 2502 and the conductive element 2514. The housing 2502 may be at ground or low potential and provide a return path to the generator 102. The conductive element 2514 may be connected to a high potential from the generator 102.

Figure 28:
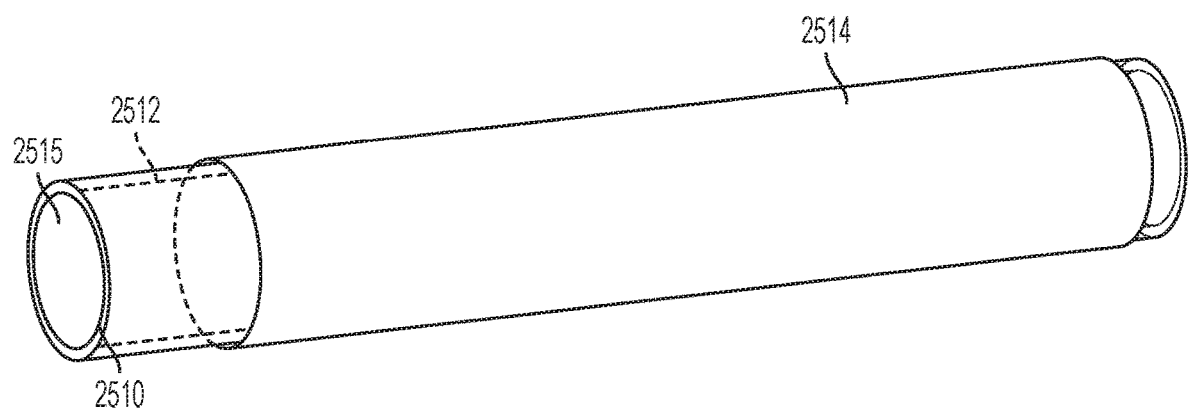
FIG. 28 is a perspective view of components of an aspect of an ultrasonic transducer assembly shown in FIG. 25.
Figure 29:
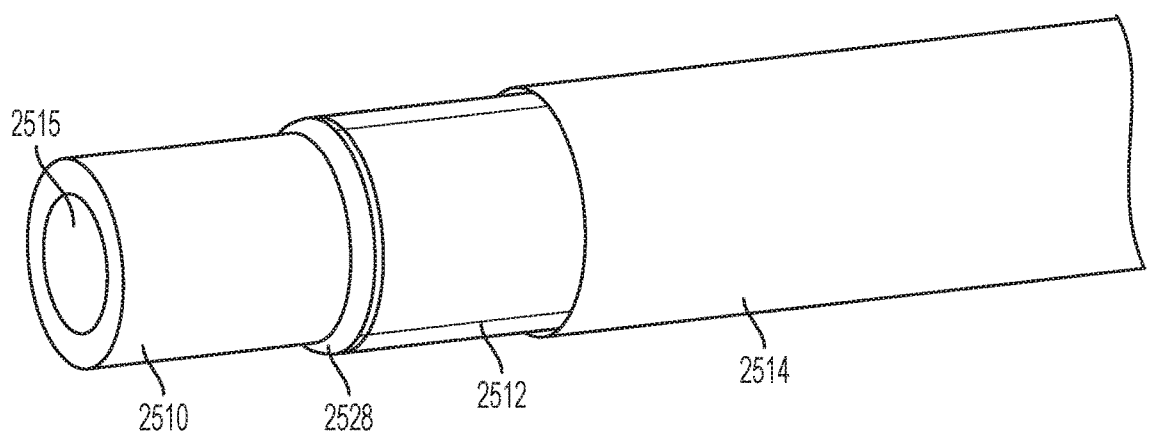
FIG. 29 is another perspective view of components of an aspect of the ultrasonic transducer assembly shown in FIG. 25.

As shown in more detail in FIGS. 28-29, conductive element 2514 may be positioned so that it surrounds the conduit section 2510 of the housing 2502 and is electrically isolated from the conduit section 2510. According to aspects, the conductive element 2514 may completely or at least partially surround the conduit section 2510. Further, insulator 2512 may be positioned and held in place between the conductive element 2514 and the conduit section 2510. As shown in FIG. 29, a feature such as an external annular ring 2528, such as for example, an o-ring made of rubber or plastic or a raised edge of material, may be present to hold the conductive element 2514 in a desired location and to provide a seal between the insulator 2512 and the conductive element 2514. The conductive element 2514 may be formed as a tube that is sized and configured to fit around the insulator 2512 and conduit section 2510 of the housing 2502. The conductive element 2514 may be made of a conductive material, such as copper, aluminum, steel, or other material as appropriate. The conductive element 2514 provides both isolation and a conductive path for high potential to the appropriate electrodes 2509a-2509e. In one aspect, each of the electrodes 2509a-2509e is a flat electrode. Accordingly, in the aspect shown in FIG. 26, the conductive element 2514 allows for energization of piezoelectric elements 2508a-2508d via the electrodes 2509b and 2509d as described in more detail below. The insulator 2512 may also be formed as a tube that is sized and configured to fit around the conduit section 2510 of the housing 2502. The insulator 2512 may be made of an insulating material, such as fiberglass, plastic, rubber, or other material as appropriate.

The ultrasonic transducer 2504 comprises a plurality of piezoelectric elements 2508a, 2508b, 2508c, 2508d arranged in a stack configuration, which may be referred to as a "Langevin stack". A longitudinal axis 2511 forms a centerline of the piezoelectric elements 2508a-2508d. A borehole 2527 is defined through the ultrasonic transducer 2504 and the end mass 2506 is positioned along the longitudinal axis 2511 adjacent a first end of the ultrasonic transducer 2504. The end mass 2506 also comprises a borehole 2527. The conduit section 2510 of the housing 2502, along with the insulator 2512 and conductive element 2514, is configured to pass through the boreholes 2527 in the ultrasonic transducer 2504 and end mass 2506. This provides an alignment feature for the ultrasonic transducer 2504 as the end mass 2506 is placed over the ultrasonic transducer 2504 and engaged with the housing 2502. The ultrasonic transducer 2504 may then be held in position in the interior compartment formed by the end mass 2506 and housing 2502 and spaced properly from the others components of the assembly 2500 so that arcing and/or shorting out of the electrode and conductive element does not occur. Furthermore, the end mass 2506 is configured to compress an end of the ultrasonic transducer 2504 against the interior surface 2528 of the housing 2502 when the end mass 2506 is engaged with the housing 2502.

In one aspect, the stack of piezoelectric elements 2508a-2508d comprises four disks made of a lead zirconate titanate (PZT) material contained in a compression housing. In other aspects, the ultrasonic transducer 2504 piezoelectric stack may comprise an even multiple (n×2) of piezoelectric elements. The piezoelectric stack may be assembled wet (glue bonded) directly onto the threaded end mass 2506 and equipped with electrically conducive elements such as wires or cables, for example, to connect the piezoelectric stack to an active energy source and ground at the generator 102 (FIGS. 1-3). Accordingly, the end mass 2506 and ultrasonic transducer 2504 may be separate components that are then bonded together to allow for assembly of the transducer assembly 2500. The piezoelectric elements 2508a-2508d are electrically connected in parallel and are paired in opposite directions. A first electrode 2509b is disposed between adjacent piezoelectric elements 2508a-2508b, a second electrode 2509c is disposed between adjacent piezoelectric elements 2508b-2508c, and a third electrode 2509d is disposed between adjacent piezoelectric elements 2508c-2508d. A fourth electrode 2509a is disposed and at the proximal end of the piezoelectric element 2508a and a fifth electrode 2509e is disposed at the end of the piezoelectric element 2508d. In one configuration, the electrodes 2509a-2509e are formed of an electrically conductive material in thin disk configuration. The electrodes 2509a-2509e are configured to electrically couple to the generator 102 (shown in FIGS. 1-3) to energize the piezoelectric elements 2508a-2508d.

In one configuration, the electrodes 2509a, 2509c, 2509e are configured to electrically couple to the negative polarity or return (−) of the generator 102 output port and the electrodes 2509b, 2509d are configured to electrically couple to the positive polarity (+) of the generator 102 output port. Electrodes 2509a, 2509c, 2509e form a return path to the generator based on contact with the end mass 2506 and the housing 2502. As shown in FIG. 26, electrodes 2509a and 2509e are in contact with an interior surface of the end mass 2506 and an interior surface of the housing 2502, respectively, when the ultrasonic transducer 2504 is held in compression by the engagement of the end mass 2506 and housing 2502. Further, electrode 2509c is in contact with the wall 2517 of the end mass 2506 based on the tabs 2526 on electrode 2509c. Electrodes 2509b and 2509d form a path to the positive polarity of the generator 102 output port based on contact between the tabs 2524 of each electrode 2509b, 2509d and the conductive element 2514. The tabs 2524 and 2526 of the electrodes 2509b, 2509d, 2509c may be sized and configured so that they hold the ultrasonic transducer 2504 at a specific distance from the surfaces with the end mass 2506 and housing 2502 and provide for a secure fit. According to aspects, the tabs 2524 and 2526 may be held in contact with the conductive element or other surface as appropriate based on the tension of material of the tabs.

In operation, the generator 102 applies an alternating voltage potential to the electrodes 2509a-2509e to energize the piezoelectric elements 2508a-2508d and cause them to mechanically expand and contract in the longitudinal direction in response to the alternating voltage potential. When the alternating voltage potential is in a frequency range of approximately 30-100 kHz, the alternating voltage potential causes the piezoelectric elements 2508a-2508d to vibrate at ultrasonic frequencies. In one example, operational frequency of alternating voltage potential is approximately 55.5 kHz. Further, in one aspect, the transducer assembly is configured to resonate at 40 kHz. Additionally, in one aspect, the ultrasonic transducer 2504 may comprise compression elements, similar to or the same as compression elements 210 discussed above, located at the ends of the piezoelectric elements 2508a and 2508d.

As shown in FIG. 26, the end mass 2506 has a distal portion having an opening 2513 defined therein for receiving the ultrasonic transducer 2504 and a wall 2517 that surrounds and houses the ultrasonic transducer 2504 when it is inserted into the opening 2513 defined by the distal portion of the end mass 2506. The end mass 2506 may include internal threads on an inner wall surface allowing for the end mass 2506 to be torqued into place with respect to the housing 2502. The horn shaped portion 2520 of the housing 2520 may serve the function of amplifying the displacement of the ultrasonic transducer 2504, and the piezoelectric elements 2508a-2508d of the ultrasonic transducer 2504 are configured to be compressed against the interior surface 2528 of the horn shaped portion 2520 of the housing 2502. According to various aspects, the diameter of the ultrasonic transducer 2504 may be smaller that the inner diameter of the end mass 2506. Accordingly, a gap 2505 may be defined between the ultrasonic transducer 2504 and the interior of the end mass 2506. This allows for insertion of the ultrasonic transducer 2504 and prevents the piezoelectric elements 2508a-2508d from coming into unwanted contact with an interior surface of the wall 2517 of the end mass 2506.

Moreover, the end mass 2506 comprises a flange 2516. The flange 2516 is shown as an annular ring around the perimeter of the end mass 2506. However, the flange 2516 may be positioned in sections located about the perimeter instead of arranged as a continuous ring. In other aspects, there may be additional flanges similar to and in addition to the flange 2516 located at predetermined locations on the end mass 2506 and/or the housing 2502. Further, the flange 2516 may be located at other locations along the end mass 2506 or the housing 2502. For example, the flange 2516 may be located along the housing 2502 closer to a distal end of the housing 2502. According to various aspects, the flange 2516 may include an O-ring or other elastomeric material member (not shown) that may provide sealing as well as damping of vibrations within the flange 2516 and the end mass 2506 overall. An o-ring may be mounted within a groove or other feature (not shown) of the flange 2516. Also, according to various aspects, the flange 2516 may be replaced with a mass having radial dimensions similar to those of the ultrasonic transducer 2504 and the end mass 2506. A hand piece housing, or other frame member, of a surgical instrument may include corresponding shapes for receiving the flange 2516.

The corresponding engagement of the end mass 2506 and horn shaped portion 2520 of the housing 2502 allows for easier assembly of the transducer assembly 2500 and provides advantages in heat dissipation and potential sealing of the ultrasonic transducer 2504 and the stack of piezoelectric elements 2508a-2508d. In other aspects, the end mass 2506 may be threaded on an outside surface in a manner that matches the threads on the horn shaped portion 2520. This enables the horn shaped portion 2520 to fit over the end mass 2506 while compressing the ultrasonic transducer 2504 within the interior of the end mass 2506. The end mass 2506 may engage with the housing 2502 based on any appropriate connection. For example, in one aspect, the end mass 2506 has an attachment surface and the housing 2502 has an attachment surface with corresponding threads for engaging the end mass 2506 and the horn shaped portion 2520. In another aspect, the end mass 2506 may be adhered to the housing 2502 using a glue or epoxy of appropriate strength. In still another aspect, the end mass 2506 and housing may be welded together. Furthermore, the engagement between the end mass 2506 and the housing 2502 may comprise a seal to prevent foreign materials from entering the area in which the ultrasonic transducer is located.

In addition, the housing 2502 may comprise an attachment end 2522 for attaching a waveguide section or other instrument section. The attachment end 2522 may be threaded or may include a quick connect and/or a locking feature for attachment of other components thereto. In various aspects, the housing 2502 and/or the end mass 2506 each may be constructed as a unitary piece or in sections. Further, the housing 2502 and the end mass 2506 each may be made from a type of metal that is appropriate for the application of the transducer assembly, for example, such as aluminum, stainless steel, titanium, and/or alloys thereof. In other aspects, the housing 2502 may be constructed from other materials, such as carbon fiber, fiberglass, plastic, etc. as appropriate.

As shown in FIG. 27, the housing 2502 comprises a conduit section 2510 and a base portion 2520. The base portion 2520 may comprise a first section 2530 having a first diameter, a second section 2532 that tapers from the first diameter to a second diameter, and a third section 2534 having the second diameter. The attachment end 2522 may have a third diameter that allows for attaching a waveguide section or other instrument section. The first section 2530 may also comprise threads (not shown) that correspond to threads on the end mass 2506 that allow for threaded engagement between the housing 2502 and end mass 2506. Additionally, the interior surface 2528 corresponds to the first diameter of the first section 2530 of the base portion 2520. The interior surface 2528 is sized and configured to correspond to the size and shape of an electrode of the ultrasonic transducer 2504. The interior surface 2528 may match the surface area of the electrode to provide a contact surface and electrical coupling between the electrode and the housing 2502. The lumen or fluid passageway 2515 is defined through the conduit section 2510 and the base portion 2520, so that fluid can pass through the entire housing 2502. According to aspects, the housing 2502 may be constructed as a single component with no gaps, seams, etc., enabling ease of cleaning, sanitizing, etc. of the housing 2502. While the base portion 2520 of the housing 2502 has a horn shape shown in FIGS. 25-27, according to other aspects, the housing 2502 may have other shapes and configurations. For example, in one aspect, the housing 2502 may not have a tapered second section 2532. Instead, a transition in the base portion 2520 may comprise an abrupt change between two different diameters of first section 2530 and third section 2534, respectively, while still having the fluid passageway 2515 defined therethrough.

Referring back to FIG. 26, the end mass 2506 may be coupled to the ultrasonic transducer 2504 and the end mass 2506 may be fixedly or removably attached with the housing 2502. In one aspect, the ultrasonic transducer 2504 is coupled or bonded to the end mass 2506. The ultrasonic transducer 2504 and the end mass 2506 or the ultrasonic transducer 2504 and the housing 2502 may be bonded together via an adhesive, a weld, or other suitable bonding mechanism. In the aspect shown in FIGS. 25-27, the end mass 2506 is configured to compress an end of the plurality of piezoelectric elements 208a-208d against an interior, distal surface of the end mass 2506 and to compress another end of the plurality of piezoelectric elements 208a-208d against the interior, proximal surface 2528 of the housing 2502 when the end mass 2506 is engaged with the housing 2502. The end mass 2506 may be configured to engage with the housing 2502 via a threaded connection. When the end mass 2506 is engaged with the housing 2502, a second end of the ultrasonic transducer 204 is compressed against an interior surface of the end mass 2506. According to aspects, the end mass 2506 may also include one or more channels to allow for wiring to be connected to the ultrasonic transducer 2504. These channels may allow for ultrasonic transducer 2504 to be energized without the use of conductive element 2514. In addition, as shown in FIGS. 25-26, the end mass 2506 may comprise a proximal torqueing feature 2507a that allows torque to be applied to the end mass 2506. The torqueing feature 2507a includes four smooth surfaces. In other aspects, the torqueing feature 2507a may be any type of drive that allows for torqueing the end, for example any type of screw drive. Furthermore, according to the aspect shown in FIGS. 25-27, the housing 2502 may also comprise a distal torqueing feature 2507b, similar to the proximal torqueing feature 2507a, which also may include four smooth surfaces.

Similar to the piezoelectric elements 208a-208d described above, the piezoelectric elements 2508a-2508d may be fabricated from any suitable material, such as, for example, lead zirconate-titanate (PZT), lead meta-niobate, lead titanate, barium titanate or other piezoelectric ceramic material. As shown in FIG. 26, each of the piezoelectric elements 2508a-2508d have a annular or ring-shaped configuration and are formed as an element with an aperture defined therethrough. In addition, the piezoelectric elements 2508a-2508d comprise a borehole 2527 through each element that allows for assembly of other features of the ultrasonic transducer 2504. In other aspects, the piezoelectric elements 2508a-2508d may have a different shape, different surface characteristics, such as additional apertures for bonding a plurality of elements together, and the elements may have an appropriate aspect factor for a particular application. Additionally, the piezoelectric elements 2508a-2508d may be energized via positive electrodes 2509b, 2509d and negative electrodes 2509a, 2509c, 2509e positioned between the piezoelectric elements 2508a-2508d and at the ends of the piezoelectric elements 2508a and 2508e as shown in FIG. 26. The positive and negative electrodes 2509a-2509e may be electrically coupled to wires via conductive element 2514 and the wires may be encased within a cable and electrically connectable to an ultrasonic signal generator of an ultrasonic system as described above. Some or all of the electrodes 2509a-2509e may be the same as or similar to electrodes 209a-209e described previously.

As shown in FIG. 26, each of positive electrodes 2509b, 2509d, negative electrodes 2509a, 2509c, 2509e, and the piezoelectric elements 2508a-2508d that make up the ultrasonic transducer 2504, each have a borehole 2527 extending therethrough. The ultrasonic transducer 204 of the transducer assembly 2500 is configured to convert an electrical signal from an ultrasonic generator, such as generator 102 described above in connection with FIGS. 1-3, into mechanical energy that results in primarily a standing acoustic wave of longitudinal vibratory motion of the ultrasonic transducer 2504 and an end effector (not shown in FIGS. 25-26) at ultrasonic frequencies. In another aspect, the vibratory motion of the ultrasonic transducer 2504 may act in a different direction. For example, the vibratory motion may comprise a local longitudinal component of a more complicated motion of the tip of the ultrasonic instrument. When the transducer assembly 2500 is energized, a vibratory motion standing wave may be generated through the transducer assembly 2500. The transducer assembly 2500 may be designed to operate at a resonance such that an acoustic standing wave pattern of a predetermined amplitude is produced. The amplitude of the vibratory motion at any point along the transducer assembly 2500 may depend upon the location along the transducer assembly 200 at which the vibratory motion is measured. A minimum or zero crossing in the vibratory motion standing wave is generally referred to as a node (e.g., where motion is usually minimal), and a local absolute value maximum or peak in the standing wave is generally referred to as an anti-node (e.g., where motion is usually maximal). According to aspects, the distance between an anti-node and its nearest node may be one-quarter wavelength ($\lambda/4$).

Furthermore, the plurality of piezoelectric elements 2508a-2508d and electrodes 2509a-e may be bonded via an adhesive, such as with an epoxy or other glue, a weld, or other suitable bonding mechanism. In one aspect, surfaces of a piezoelectric element 2508a-2508d may have an adhesive, such as epoxy, placed on it and then an electrode may be placed over the adhesive. The adhesive may be provided in a layer such that it does not interfere with the electrical connections between the electrodes 2509a-2509e and the piezoelectric elements 2508a-2508d and the piezoelectric elements 2508a-2508d themselves. Further, according to aspects, only some of the piezoelectric elements 2508a-2508d may be bonded together, instead of the entire number of piezoelectric elements 2508a-2508d. In addition, the plurality of piezoelectric elements 2508a-2508d may be assembled dry, with no adhesive or bonding mechanism between each of the layers. Additionally, any openings or spacing between the conductive element 2514 and the borehole 2527 through the end mass 2506 may have sealing product, such as solder, epoxy, glue, rubber, or other insulation material, located therein to prevent the entry of foreign substances into the interior compartment formed by the engagement of end mass 2506 and housing 2502.

FIGS. 30 and 31 illustrate aspects of electrodes 3002 and 3008, respectively. As shown in FIG. 30, electrode 3002 comprises an annular shaped surface 3001 with an outer edge 3005 and an aperture that defines an inner edge 3007 of the electrode 3002. Electrode 3002 further comprises a plurality of tabs 3003 that extend inward towards the center of the electrode 3002. As shown in FIG. 31, similar to electrode 3002, electrode 3008 comprises an annular shaped surface 3001 with an outer edge 3005 and an aperture that defines an inner edge 3007 of the electrode 3008. Electrode 3008 further comprises a plurality of tabs 3009 that extend outward, away from the center of the electrode 3008. The electrode tabs 3003 and 3009 serve to provide both an electrical conductivity path as well as a centering function during the process of constructing the transducer assembly 2500. Accordingly, the tabs 3003 may be sized and configured to contact the conductive element 2514 to provide for electrical energization of the piezoelectric elements 2508a-2508d of the ultrasonic transducer 2504. Additionally, tabs 3009 may be sized and configured to contact the inside surface of the wall of the end mass 2506, to provide an electrical ground for the ultrasonic transducer 2504. In one aspect, each of tabs 3003, 3009, can be twisted during construction of the transducer assembly 2500, such that the contacting edge/region of a tab aligns more favorably with the motion of the contacting surface of the mating part during assembly of the transducer assembly 2500.

FIG. 32 provides an illustration of the contact made between the tabs 3003 of electrode 3002 and conductive element 2514 during assembly of the components. One or more of tabs 3003 may have solder 3010 present thereon, to establish an electrical connection between the electrode 3002 and the conductive element 2514. In one aspect, the solder 3010 may be placed on the tab 3003 after the electrode 3002 has been put into place, for example, by twisting the electrode 3002 over the conductive element 2514, at a location along the conductive element 2514. In another aspect, the tab 3003 may be pre-soldered, such that the solder 3010 is placed on the tab 3003 prior to assembly of the electrode 3002 and conductive element 2514. The solder 3010 may be heated, for example, during a reflow soldering process or by direct heating applied to the solder, to complete a connection. According to aspects, tabs 3009 of electrode 3008 may be pre-soldered and connected to a surface in the same or similar fashion. In one aspect, solder may be used where the contact pressure between the conductive element or other surface and the electrode tabs 3003, 3009 becomes insufficient, and the tabs 3003, 3009 could be pre-soldered, installed, and necessary heat applied to the conductive element or other surface to melt the solder and make a gas-tight connection.

While various details have been set forth in the foregoing description, it will be appreciated that the various aspects of the surgical system with user adaptable techniques employing simultaneous energy modalities based on tissue parameters may be practiced without these specific details. For example, for conciseness and clarity, selected aspects have been shown in block diagram form rather than in detail. Some portions of the detailed descriptions provided herein may be presented in terms of instructions that operate on data that is stored in a computer memory. Such descriptions and representations are used by those skilled in the art to describe and convey the substance of their work to others skilled in the art. In general, a technique refers to a self-consistent sequence of steps leading to a desired result, where a "step" refers to a manipulation of physical quantities which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities.

Unless specifically stated otherwise as apparent from the foregoing discussion, it is appreciated that, throughout the foregoing description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

It is worthy to note that any reference to "one aspect," "an aspect," "one aspect," or "an aspect" means that a particular feature, structure, or characteristic described in connection with the aspect is included in at least one aspect. Thus, appearances of the phrases "in one aspect," "in an aspect," "in one aspect," or "in an aspect" in various places throughout the specification are not necessarily all referring to the same aspect. Furthermore, the particular features, structures or characteristics may be combined in any suitable manner in one or more aspects.

Some aspects may be described utilizing the expression "coupled" and "connected" along with their derivatives. It should be understood that these terms are not intended as synonyms for each other. For example, some aspects may be described utilizing the term "connected" to indicate that two or more elements are in direct physical or electrical contact with each other. In another example, some aspects may be described utilizing the term "coupled" to indicate that two or more elements are in direct physical or electrical contact.

The term "coupled," however, also may mean that two or more elements are not in direct contact with each other, but yet still co-operate or interact with each other.

Although various aspects have been described herein, many modifications, variations, substitutions, changes, and equivalents to those aspects may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed aspects. The following claims are intended to cover all such modification and variations.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., aspects of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various aspects of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one aspect, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some forms of the aspects disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of aspects, and that an illustrative aspect of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

All of the above-mentioned U.S. patents, U.S. patent application publications, U.S. patent applications, foreign patents, foreign patent applications, non-patent publications referred to in this specification and/or listed in any Application Data Sheet, or any other disclosure material are incorporated herein by reference, to the extent not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely examples and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated also can be viewed as being "operably connected," or "operably coupled," to each other to achieve the desired functionality, and any two components capable of being so associated also can be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Although various aspects have been described herein, many modifications, variations, substitutions, changes, and equivalents to those aspects may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed aspects. The following claims are intended to cover all such modification and variations.

In summary, numerous benefits have been described which result from employing the concepts described herein. The foregoing description of the one or more aspects has been presented for purposes of illustration and description. It is not intended to be exhaustive or limiting to the precise aspect disclosed. Modifications or variations are possible in light of the above teachings. The one or more aspects were chosen and described in order to illustrate principles and practical application to thereby enable one of ordinary skill in the art to utilize the various aspects and with various modifications as are suited to the particular use contemplated. It is intended that the claims submitted herewith define the overall scope.

Various aspects of the subject matter described herein are set out in the following numbered examples:

EXAMPLE 1

A surgical instrument for coagulating and dissecting tissue, the surgical instrument comprising: a transducer assembly comprising:

a housing;

an ultrasonic transducer comprising a plurality of piezoelectric elements and a plurality of electrodes arranged in a stack configuration, wherein an electrode is located between each pair of solid piezoelectric elements;

an end mass positioned adjacent a first end of the ultrasonic transducer, wherein the end mass is configured to engage with the housing; and wherein the end mass is configured to compress the ultrasonic transducer against an interior surface of the housing when the end mass is engaged with the housing.

EXAMPLE 2

The surgical instrument of Example 1, wherein the plurality of piezoelectric elements have a longitudinal axis and the end mass has a longitudinal axis that is aligned with the longitudinal axis of the plurality of piezoelectric elements.

EXAMPLE 3

The surgical instrument of Example 1 or 2, wherein the housing comprises a portion having an opening defined therein, wherein the ultrasonic transducer is configured to fit within the portion of the housing and the end mass is configured to engage with the housing via a threaded connection between the end mass and the portion of the housing.

EXAMPLE 4

The surgical instrument of any one or more of Example 1 through Example 3, wherein at least one of the plurality of piezoelectric elements is a solid piezoelectric element.

EXAMPLE 5

The surgical instrument of any one or more of Example 1 through Example 4, wherein the stack configuration further comprises:
  a first electrode located at a first end of the stack configuration and in contact with one surface of a first piezoelectric element; and
  a second electrode located at a second end of the stack configuration and in contact with one surface of a second piezoelectric element.

EXAMPLE 6

The surgical instrument of any one or more of Example 1 through Example 5, further comprising an alignment feature configured to provide a gap between the plurality of piezoelectric elements and a side wall of the interior surface of the housing.

EXAMPLE 7

The surgical instrument of any one or more of Example 1 through Example 6, wherein the end mass comprises a torqueing feature that allows torque to be applied to the end mass.

EXAMPLE 8

The surgical instrument of any one or more of Example 1 through Example 7, wherein the transducer assembly is configured to resonate at 40 kHz.

EXAMPLE 9

The surgical instrument of any one or more of Example 1 through Example 8, wherein the end mass is configured to engage with the housing via a threaded connection.

EXAMPLE 10

The surgical instrument of any one or more of Example 1 through Example 9, wherein a first piezoelectric element of the plurality of piezoelectric elements and a second piezoelectric element of the plurality of piezoelectric elements are electrically connected in parallel.

EXAMPLE 11

The surgical instrument of any one or more of Example 1 through Example 10, wherein the ultrasonic transducer is sealed within the housing.

EXAMPLE 12

The surgical instrument of any one or more of Example 1 through Example 11, wherein the end mass is bonded to the housing to create a seal around the interior surface of the housing.

EXAMPLE 13

The surgical instrument of any one or more of Example 1 through Example 12, further comprising an electrical contact that is configured to electrically couple to an exterior surface of the housing.

EXAMPLE 14

The surgical instrument of any one or more of Example 1 through Example 13, further comprising a surgical instrument housing, wherein the transducer assembly is located with the surgical instrument housing and is configured to be rotatable within the surgical instrument housing.

EXAMPLE 15

The surgical instrument of any one or more of Example 1 through Example 14, further comprising a spacer element, wherein the spacer element is located at a first end of the stack configuration and wherein a first end of the end mass contacts the spacer element when the end mass compresses the ultrasonic transducer.

EXAMPLE 16

The surgical instrument of any one or more of Example 1 through Example 15, wherein, when the end mass compresses the ultrasonic transducer against the interior surface of the housing, the first end of the ultrasonic transducer contacts a first end of the end mass and a second end of the ultrasonic transducer is compressed against the interior surface of the housing.

EXAMPLE 17

The surgical instrument of any one or more of Example 1 through Example 16, wherein at least one of the plurality of piezoelectric elements is a solid piezoelectric element having a disk shape.

EXAMPLE 18

A surgical instrument for coagulating and dissecting tissue, the surgical instrument comprising:
  a transducer assembly comprising:
    a housing;
    an ultrasonic transducer comprising a plurality of solid piezoelectric elements and a plurality of electrodes arranged in a stack configuration having a longitudinal axis, a first end, and a second end, wherein an electrode is located between each pair of solid piezoelectric elements, an electrode is located at the first end of the stack configuration, and an electrode is located at the second end of the stack configuration;
an end mass positioned along the longitudinal axis adjacent a first end of the ultrasonic transducer and coupled to the ultrasonic transducer, wherein the end mass is configured to engage with the housing; and
wherein the end mass is configured to compress the ultrasonic transducer against an interior surface of the housing when the end mass is engaged with the housing; and
wherein a first solid piezoelectric element of the plurality of solid piezoelectric elements and a second solid piezoelectric element of the plurality of solid piezoelectric elements are electrically connected in parallel.

EXAMPLE 19

A surgical instrument for coagulating and dissecting tissue, the surgical instrument comprising:
a transducer assembly comprising:
a housing;
an ultrasonic transducer comprising:
  a plurality of piezoelectric elements and a plurality of electrodes arranged in a stack configuration having a first end and a second end, wherein a first electrode is located between a first pair of piezoelectric elements, a second electrode is located between a second pair of piezoelectric elements, a third electrode is located at the first end of the stack configuration, and a fourth electrode is located at the second end of the stack configuration;
  a first spacer element in contact with the third electrode;
  a second spacer element in contact with the fourth electrode;
an end mass having a first end, a second end, and an aperture therethrough, the end mass being positioned adjacent a first end of the ultrasonic transducer, wherein the end mass is configured to engage with the housing;
wherein the end mass is configured to compress the ultrasonic transducer against an interior surface of the housing when the end mass is engaged with the housing; and
wherein the first end of the end mass contacts the first spacer element when the end mass compresses the ultrasonic transducer; and
wherein the second spacer element contacts the interior surface of the housing when the end mass compresses the ultrasonic transducer.

EXAMPLE 20

A surgical instrument for coagulating and dissecting tissue, the surgical instrument comprising:
a transducer assembly comprising:
a housing;
an ultrasonic transducer comprising:
  a plurality of piezoelectric elements and a plurality of electrodes arranged in a stack configuration having a first end and a second end, wherein a first electrode is located between a first pair of piezoelectric elements, a second electrode is located between a second pair of piezoelectric elements, a third electrode is located at the first end of the stack configuration, and a fourth electrode is located at the second end of the stack configuration;
  a first spacer element in contact with the third electrode;
  a second spacer element in contact with the fourth electrode;
an end mass having a first end, a second end, and an aperture therethrough, the end mass being positioned adjacent a first end of the ultrasonic transducer, wherein the end mass is configured to engage with the housing;
wherein the end mass is configured to compress the ultrasonic transducer against an interior surface of the housing when the end mass is engaged with the housing; and
wherein the first end of the end mass contacts the first spacer element when the end mass compresses the ultrasonic transducer; and
wherein the second spacer element contacts the interior surface of the housing when the end mass compresses the ultrasonic transducer.

EXAMPLE 21

The surgical instrument of Example 20, wherein the plurality of piezoelectric elements have a longitudinal axis and the end mass has a longitudinal axis that is aligned with the longitudinal axis of the plurality of piezoelectric elements.

EXAMPLE 22

The surgical instrument of Example 20 or 21, wherein the end mass comprises a distal portion having an opening defined therein, wherein the ultrasonic transducer is configured to fit within the distal portion of the end mass and the housing is configured to engage with the end mass via a threaded connection between the housing and the distal portion of the end mass.

EXAMPLE 23

The surgical instrument of any one or more of Example 20 through 22, wherein the end mass comprises a wall that at least partially surrounds and houses the ultrasonic transducer.

EXAMPLE 24

The surgical instrument of any one or more of Example 20 through 23, wherein the electrode is a first electrode and wherein the ultrasonic transducer further comprises: a second electrode located at the first end of the ultrasonic transducer and in contact with one surface of a first piezoelectric element of the plurality of piezoelectric elements; and a third electrode located at a second end of the ultrasonic transducer and in contact with one surface of a second piezoelectric element of the plurality of piezoelectric elements.

EXAMPLE 25

The surgical instrument of any one or more of Example 20 through 24, wherein the end mass comprises a torqueing feature that allows torque to be applied to the end mass.

EXAMPLE 26

The surgical instrument of any one or more of Example 20 through 25, wherein the end mass is configured to engage with the housing via a threaded connection.

EXAMPLE 27

The surgical instrument of any one or more of Example 20 through 26, further comprising a conductive element adjacent the conduit section of the housing.

EXAMPLE 28

The surgical instrument of Example 27, wherein the conductive element at least partially surrounds the conduit section of the housing and is electrically isolated from the conduit section.

EXAMPLE 29

The surgical instrument of Example 27, further comprising an insulator between the conductive element and the conduit section.

EXAMPLE 30

The surgical instrument of Example 27, wherein the electrode is electrically coupled to the conductive element.

EXAMPLE 31

The surgical instrument of Example 27, wherein the electrode is electrically coupled to the conductive element via at least one tab of the electrode.

EXAMPLE 32

The surgical instrument of any one or more of Example 20 through 31, wherein the end mass is bonded to the housing to create a seal around an interior compartment defined when the housing and the end mass are engaged.

EXAMPLE 33

The surgical instrument of any one or more of Example 20 through 32, further comprising a surgical instrument housing, wherein the transducer assembly is located with the surgical instrument housing.

EXAMPLE 34

The surgical instrument of any one or more of Example 20 through 33, wherein, when the end mass compresses the ultrasonic transducer against the interior surface of the housing, the first end of the ultrasonic transducer contacts an interior surface of the end mass and a second end of the ultrasonic transducer is compressed against the interior surface of the housing.

EXAMPLE 35

The surgical instrument of any one or more of Example 20 through 34, wherein the electrode comprises an outer edge and an aperture that defines an inner edge of the electrode.

EXAMPLE 36

The surgical instrument of Example 35, wherein the inner edge comprises at least one tab extending towards a center of the aperture.

EXAMPLE 37

The surgical instrument of Example 35, wherein the outer edge comprises at least one tab extending outwards from a center of the aperture.

EXAMPLE 38

A surgical instrument for coagulating and dissecting tissue, the surgical instrument comprising:
a transducer assembly comprising:
a housing comprising a conduit section and a base portion, wherein a fluid passageway is defined through the conduit section and the base portion;
an ultrasonic transducer comprising a plurality of piezoelectric elements and a plurality of electrodes arranged in a stack configuration, the ultrasonic transducer having a longitudinal axis, a first end, and a second end, wherein a first borehole is defined through the ultrasonic transducer, wherein a first electrode is located between each pair of piezoelectric elements, a second electrode is located at the first end of the ultrasonic transducer, and a third electrode is located at the second end of the ultrasonic transducer;
an end mass comprising a second borehole defined therethrough, the end mass positioned along the longitudinal axis and adjacent a first end of the ultrasonic transducer, wherein the end mass is configured to engage with the housing; and
wherein the conduit section of the housing is configured to pass through the first borehole of the ultrasonic transducer and the second borehole of the end mass; and
wherein the end mass is configured to compress the ultrasonic transducer against a surface of the housing when the end mass is engaged with the housing; and
wherein a first piezoelectric element of the plurality of piezoelectric elements and a second piezoelectric element of the plurality of piezoelectric elements are electrically connected in parallel.

EXAMPLE 39

A transducer assembly comprising:
a housing comprising a conduit section and a base portion, wherein a fluid passageway is defined through the conduit section and the base portion;
a conductive element at least partially surrounding the conduit section of the housing; and
a insulator positioned between the conductive element and the conduit section, wherein the insulator electrically isolates the conductive element from the conduit section;
an ultrasonic transducer comprising a plurality of piezoelectric elements and a plurality of electrodes arranged in a stack configuration, the ultrasonic transducer having a longitudinal axis, a first end, and a second end, wherein a first borehole is defined through the ultrasonic transducer, wherein a first electrode is located between each pair of piezoelectric elements, a second electrode is located at the first end of the ultrasonic transducer, and a third electrode is located at the second end of the ultrasonic transducer, wherein the first electrode is electrically coupled to the conductive element; and an end mass comprising a second borehole defined therethrough, the end mass positioned along the longitudinal axis and adjacent a first end of the ultrasonic transducer, wherein the end mass is configured to engage with the housing; and wherein the conduit section of the housing is configured to pass through the first borehole of the ultrasonic transducer and the second borehole of the end mass; and wherein the end mass is configured to compress the ultrasonic transducer against a surface of the housing when the end mass is engaged with the housing; and wherein a first piezoelectric element of the plurality of piezoelectric elements and a second piezoelectric element of the plurality of piezoelectric elements are electrically connected in parallel.

The invention claimed is:

1. A surgical instrument for coagulating and dissecting tissue, the surgical instrument comprising:
   a transducer assembly comprising:
      a housing comprising a conduit section and a base portion, wherein the conduit section and the base portion define a fluid passageway;
      an ultrasonic transducer comprising a plurality of piezoelectric elements and a plurality of electrodes arranged in a stack configuration, wherein at least one of the plurality of electrodes is located between at least one pair of the plurality of piezoelectric elements, and wherein a first borehole is defined through the ultrasonic transducer; and
      an end mass comprising a second borehole defined therethrough, wherein a surface of the end mass is positioned adjacent a first end of the ultrasonic transducer, wherein the end mass is configured to engage with the housing, and wherein the end mass comprises a wall that at least partially surrounds and houses the ultrasonic transducer; and
      wherein:
         the conduit section of the housing is configured to pass through the first borehole of the ultrasonic transducer and the second borehole of the end mass; and
         the end mass is configured to compress the ultrasonic transducer against an interior surface of the housing when the end mass is engaged with the housing.

2. The surgical instrument of claim 1, wherein the stack configuration comprises:
   a first electrode of the plurality of electrodes located at a first end of the ultrasonic transducer, wherein the first electrode is in contact with a surface of a first piezoelectric element of the plurality of piezoelectric elements; and
   a second electrode of the plurality of electrodes located at a second end of the ultrasonic transducer, wherein the second electrode is in contact with a surface of a second piezoelectric element of the plurality of piezoelectric elements.

3. The surgical instrument of claim 1, further comprising:
   a conductive element positioned adjacent the conduit section of the housing, wherein the conductive element at least partially surrounds the conduit section of the housing; and
   an insulator positioned between the conductive element and the conduit section, wherein the insulator is configured to electrically isolate the conductive element from the conduit section.

4. The surgical instrument of claim 3, wherein each of the plurality of electrodes is electrically coupled to the conductive element via at least one tab of each electrode.

5. The surgical instrument of claim 1, wherein each of the plurality of electrodes comprises an outer edge and an aperture that defines an inner edge of each electrode.

6. The surgical instrument of claim 5, wherein:
   the inner edge comprises at least one tab extending towards a center of the aperture; and
   the outer edge comprises at least one tab extending outwards from the center of the aperture.

7. The surgical instrument of claim 1, wherein:
   the end mass is configured to engage with the housing via a threaded connection;
   a first piezoelectric element of the plurality of piezoelectric elements; and
   a second piezoelectric element of the plurality of piezoelectric elements are electrically connected in parallel.

8. A surgical instrument for coagulating and dissecting tissue, the surgical instrument comprising:
   a transducer assembly comprising:
      a housing comprising a conduit section and a base portion, wherein the conduit section and the base portion define a fluid passageway;
      an ultrasonic transducer comprising a plurality of piezoelectric elements and a plurality of electrodes arranged in a stack configuration, wherein at least one of the plurality of electrodes is located between at least one pair of the plurality of piezoelectric elements, and wherein a first borehole is defined through the ultrasonic transducer; and
      an end mass comprising a second borehole defined therethrough, wherein a surface of the end mass is positioned adjacent a first end of the ultrasonic transducer, wherein the end mass is configured to engage with the housing, and wherein the end mass comprises a torqueing feature that allows torque to be applied to the end mass; and
      wherein:
         the conduit section of the housing is configured to pass through the first borehole of the ultrasonic transducer and the second borehole of the end mass; and
         the end mass is configured to compress the ultrasonic transducer against an interior surface of the housing when the end mass is engaged with the housing.

9. The surgical instrument of claim 8, further comprising:
   a conductive element positioned adjacent the conduit section of the housing, wherein the conductive element at least partially surrounds the conduit section of the housing; and
   an insulator positioned between the conductive element and the conduit section, wherein the insulator is configured to electrically isolate the conductive element from the conduit section.

10. The surgical instrument of claim 9, wherein each of the plurality of electrodes is electrically coupled to the conductive element via at least one tab of each electrode.

11. The surgical instrument of claim 8, wherein the end mass is configured to compress the ultrasonic transducer against an interior surface of the housing when the end mass is engaged with the housing.

12. The surgical instrument of claim 8, wherein each of the plurality of electrodes comprises an outer edge and an aperture that defines an inner edge of each electrode.

13. The surgical instrument of claim 12, wherein:
the inner edge comprises at least one tab extending towards a center of the aperture; and
the outer edge comprises at least one tab extending outwards from the center of the aperture.

14. A surgical instrument for coagulating and dissecting tissue, the surgical instrument comprising:
a transducer assembly comprising:
a housing comprising a conduit section and a base portion, wherein the conduit section and the base portion define a fluid passageway;
an ultrasonic transducer comprising a plurality of piezoelectric elements and a plurality of electrodes arranged in a stack configuration, wherein at least one of the plurality of electrodes is located between at least one pair of the plurality of piezoelectric elements, and wherein a first borehole is defined through the ultrasonic transducer; and
an end mass comprising a second borehole defined therethrough, wherein a surface of the end mass is positioned adjacent a first end of the ultrasonic transducer, wherein the end mass is configured to engage with the housing, and wherein the end mass is bonded to the housing to create a seal around an interior compartment defined when the housing and the end mass are engaged; and
wherein:
the conduit section of the housing is configured to pass through the first borehole of the ultrasonic transducer and the second borehole of the end mass; and
the end mass is configured to compress the ultrasonic transducer against an interior surface of the housing when the end mass is engaged with the housing.

15. The surgical instrument of claim 14, further comprising:
a conductive element positioned adjacent the conduit section of the housing, wherein the conductive element at least partially surrounds the conduit section of the housing; and
an insulator positioned between the conductive element and the conduit section, wherein the insulator is configured to electrically isolate the conductive element from the conduit section.

16. The surgical instrument of claim 15, wherein each of the plurality of electrodes is electrically coupled to the conductive element via at least one tab of each electrode.

17. The surgical instrument of claim 14, wherein the end mass is configured to compress the ultrasonic transducer against an interior surface of the housing when the end mass is engaged with the housing.

18. The surgical instrument of claim 14, wherein each of the plurality of electrodes comprises an outer edge and an aperture that defines an inner edge of each electrode.

19. The surgical instrument of claim 18, wherein:
the inner edge comprises at least one tab extending towards a center of the aperture; and
the outer edge comprises at least one tab extending outwards from the center of the aperture.

* * * * *